(12) United States Patent
Chen et al.

(10) Patent No.: US 9,273,098 B2
(45) Date of Patent: *Mar. 1, 2016

(54) LACTAM-BRIDGED MELANOCORTIN RECEPTOR-SPECIFIC PEPTIDES

(75) Inventors: Xin Chen, Furlong, PA (US); Wei Yang, Edison, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 1120 days.

This patent is subject to a terminal disclaimer.

(21) Appl. No.: 13/311,817

(22) Filed: Dec. 6, 2011

(65) Prior Publication Data

US 2012/0077957 A1 Mar. 29, 2012

Related U.S. Application Data

(63) Continuation of application No. PCT/US2010/037584, filed on Jun. 7, 2010.

(60) Provisional application No. 61/184,940, filed on Jun. 8, 2009.

(51) Int. Cl.
- *C07K 7/50* (2006.01)
- *C07K 7/56* (2006.01)
- *C07K 5/117* (2006.01)
- *C07K 14/685* (2006.01)
- *A61K 38/00* (2006.01)

(52) U.S. Cl.
CPC .............. *C07K 7/56* (2013.01); *C07K 5/1024* (2013.01); *C07K 14/685* (2013.01); *A61K 38/00* (2013.01)

(58) Field of Classification Search
CPC .................................. C07K 7/50; C07K 7/52
USPC ........................................................ 530/317
See application file for complete search history.

(56) References Cited

U.S. PATENT DOCUMENTS

| | | | |
|---|---|---|---|
| 5,576,290 | A | 11/1996 | Hadley |
| 5,674,839 | A | 10/1997 | Hruby et al. |
| 5,731,408 | A | 3/1998 | Hadley et al. |
| 6,054,556 | A | 4/2000 | Huby et al. |
| 6,350,430 | B1 | 2/2002 | Dooley et al. |
| 6,476,187 | B1 | 11/2002 | Cone et al. |
| 6,579,968 | B1 | 6/2003 | Blood et al. |
| 6,600,015 | B2 | 7/2003 | Chen et al. |
| 6,613,874 | B1 | 9/2003 | Mazur et al. |
| 6,699,873 | B1 | 3/2004 | Maguire et al. |
| 6,794,489 | B2 | 9/2004 | Blood et al. |
| 6,887,846 | B2 | 5/2005 | Catania et al. |
| 6,951,916 | B2 | 10/2005 | Mazur et al. |
| 7,008,925 | B1 | 3/2006 | Szardenings et al. |
| 7,176,279 | B2 | 2/2007 | Sharma et al. |
| 7,517,854 | B2 | 4/2009 | Conde-Frieboes et al. |
| 7,541,430 | B2 | 6/2009 | Sensfuss et al. |
| 2001/0056179 | A1 | 12/2001 | Chen et al. |
| 2002/0143141 | A1 | 10/2002 | Chen et al. |
| 2003/0064921 | A1 | 4/2003 | Millhauser et al. |
| 2003/0105024 | A1 | 6/2003 | Cone et al. |
| 2003/0212002 | A1 | 11/2003 | Haskell-Luevano et al. |
| 2004/0023859 | A1 | 2/2004 | Mazur et al. |
| 2004/0138136 | A1 | 7/2004 | Sharma et al. |
| 2005/0130901 | A1 | 6/2005 | Lipton et al. |
| 2005/0164914 | A1 | 7/2005 | Sharma et al. |
| 2005/0187164 | A1 | 8/2005 | Pinel |
| 2005/0222014 | A1 | 10/2005 | Diamond et al. |

(Continued)

FOREIGN PATENT DOCUMENTS

| WO | WO-98/27113 | 6/1998 |
|---|---|---|
| WO | WO-99/021571 | 5/1999 |

(Continued)

OTHER PUBLICATIONS

Adan, Rah et al., "The MC4 Receptor and Control of Appetite", *British Journal of Pharmacology*, (Oct. 16, 2006), 149:815-827.

Balbani, Aracy P., et al., "Recent developments for smoking cessation and treatment of nicotine dependence", *Informa healthcare / Expert Opinion*, (2007),17:287-297.

Bednarek, Maria A., et al., "Analogs of MTII, Lactam Derivatives of alpha-Melanotropin, Modified at the n-Terminus, and their selectivity at human melanocortin receptors 3, 4 and 5", *Biochemical and Biophysical Research Communications*, (1999),261:209-213.

(Continued)

*Primary Examiner* — David Lukton
(74) *Attorney, Agent, or Firm* — Stephen A. Slusher

(57) ABSTRACT

Lactam-bridged melanocortin receptor-specific cyclic peptides of the formula

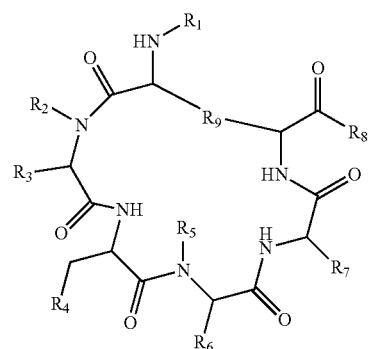

where $R_1$, $R_2$, $R_3$, $R_4$, $R_5$, $R_6$, $R_7$, $R_8$ and $R_9$ are as defined in the specification, compositions and formulations including the peptides of the foregoing formula, and methods of preventing, ameliorating or treating melanocortin receptor-mediated diseases, indications, conditions and syndromes, including obesity, modulation of feeding behavior, related metabolic syndrome, sexual dysfunction, male erectile dysfunction and female sexual dysfunction.

20 Claims, 5 Drawing Sheets

(56) References Cited

U.S. PATENT DOCUMENTS

| | | |
|---|---|---|
| 2005/0239711 A1 | 10/2005 | Chen et al. |
| 2006/0014194 A1 | 1/2006 | Sharma et al. |
| 2006/0105951 A1 | 5/2006 | Cunningham et al. |
| 2006/0111281 A1 | 5/2006 | Sharma et al. |
| 2006/0135436 A1 | 6/2006 | Haskell-Luevano et al. |
| 2006/0258590 A1 | 11/2006 | Haskell-Luevano |
| 2006/0293223 A1 | 12/2006 | Gadski et al. |
| 2007/0027091 A1 | 2/2007 | Conde-Frieboes et al. |
| 2007/0105759 A1 | 5/2007 | Flora et al. |
| 2007/0123453 A1 | 5/2007 | Heiman et al. |
| 2007/0244054 A1 | 10/2007 | Sensfuss et al. |
| 2007/0293423 A1 | 12/2007 | Jungheim et al. |
| 2008/0004213 A1 | 1/2008 | Humphrey |
| 2008/0039387 A1 | 2/2008 | Sensfuss et al. |
| 2008/0305152 A1 | 12/2008 | Kleinig et al. |
| 2010/0311648 A1 | 12/2010 | Dodd et al. |

FOREIGN PATENT DOCUMENTS

| | | |
|---|---|---|
| WO | WO-99/54358 | 10/1999 |
| WO | WO-00/05263 | 2/2000 |
| WO | WO-00/35952 | 6/2000 |
| WO | WO-00/58361 | 10/2000 |
| WO | WO-01/30808 | 5/2001 |
| WO | WO-01/52880 | 7/2001 |
| WO | WO-01/74844 | 10/2001 |
| WO | WO-01/85930 | 11/2001 |
| WO | WO-01/90140 | 11/2001 |
| WO | WO-02/18437 | 3/2002 |
| WO | WO-02/026774 | 4/2002 |
| WO | WO-03/006604 | 1/2003 |
| WO | WO-03/006620 | 1/2003 |
| WO | WO-2004/005324 | 1/2004 |
| WO | WO-2004/046166 | 6/2004 |
| WO | WO-2004/099246 | 11/2004 |
| WO | WO-2005/000338 | 1/2005 |
| WO | WO-2005/000339 | 1/2005 |
| WO | WO-2005/000877 | 1/2005 |
| WO | WO-2005/014617 | 2/2005 |
| WO | WO-2005/030797 | 4/2005 |
| WO | WO-2005/048967 | 6/2005 |
| WO | WO-2005/060985 | 7/2005 |
| WO | WO-2006/012667 | 2/2006 |
| WO | WO-2006/014552 | 2/2006 |
| WO | WO-2006/048449 | 5/2006 |
| WO | WO-2006/048450 | 5/2006 |
| WO | WO-2006/048451 | 5/2006 |
| WO | WO-2006/048452 | 5/2006 |
| WO | WO-2006/097526 | 9/2006 |
| WO | WO-2007/008684 | 1/2007 |
| WO | WO-2007/008704 | 1/2007 |
| WO | WO-2007/009894 | 1/2007 |
| WO | WO-2007/027574 | 3/2007 |
| WO | WO-2008/025094 | 3/2008 |
| WO | WO-2008/087186 | 7/2008 |
| WO | WO-2008/087187 | 7/2008 |
| WO | WO 2008/087188 | 7/2008 |
| WO | WO-2008/087189 | 7/2008 |
| WO | WO-2008/087190 | 7/2008 |
| WO | WO-2008/156677 | 12/2008 |
| WO | WO-2009/061411 | 5/2009 |
| WO | WO-2009/151383 | 12/2009 |
| WO | WO 2009/152079 | 12/2009 |

OTHER PUBLICATIONS

Communication, "Supplementary European Search Report", EP Application 10786617, (Oct. 15, 2012).

Gautron, Laurent et al., "Melanocortin-4 Receptor Expression in a Vago-vagal Circuitry Involved in Postprandial Functions", *The Journal of Comparative Neurology*, (2010),518:6-24.

Giuliani, D. et al., "Selective melanocortin MC4 receptor agonists reverse haemorrhagic shock and prevent multiple organ damage", *British Journal of Pharmacology*, (2007), 150:595-603.

Hadley, Mac E., et al., "The Proopiomelanocortin System", *Annals New York Academy of Science*, (1995),1-21.

Maaser, Christian et al., "Role of the Melanocortin System in Inflammation", *Ann. N. Y. Acad. Science*, (2006), 1072:123-134.

Navarro, Montserrat et at., "Effects of Melanocortin Receptor Activation and Blockade on Ethanol Intake: A Possible Role for the Melanocortin-4 Receptor", *Alcohol Clin. Exp. Res.*, (2005),29(6):949-957.

Nogueiras, Ruben et al., "The central melanocortin system directly controls peripheral lipid metabolism", *The Journal of Clinical Investigation*, (2007), 117(11): 3475.

Wikberg, Jarl E., et al., "Targeting melanocortin receptors: an approach to treat weight disorders and sexual dysfunction", *Nature Reviews Drug Discovery*, (2008),7:307-323.

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Synthetic melanocortin binding peptide derived
      from human alpha-MSH

<400> SEQUENCE: 1

His Phe Arg Trp
1
```

```
<210> SEQ ID NO 2
<211> LENGTH: 13
<212> TYPE: PRT
<213> ORGANISM: Artificial Sequence
<220> FEATURE:
<223> OTHER INFORMATION: Synthetic melanocortin binding peptide derived
      from human alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION

<400> SEQUENCE: 2

Ser Tyr Ser Met Glu His Phe Arg Trp Gly Lys Pro Val
1               5                   10
```

LACTAM-BRIDGED MELANOCORTIN RECEPTOR-SPECIFIC PEPTIDES

CROSS REFERENCE TO RELATED APPLICATION

This application is a continuation application of International Application No. PCT/US2010/037584, published as International Publication No. WO 2010/144341, entitled "Lactam-Bridged Melanocortin Receptor-Specific Peptides", filed on Jun. 7, 2010, which in turn claimed priority to and the benefit of the filing of U.S. Provisional Patent Application Ser. No. 61/184,940, entitled "Lactam-Bridged Melanocortin Receptor-Specific Peptides", filed Jun. 8, 2009. The specification and claims of each of the foregoing applications are incorporated herein by reference.

BACKGROUND OF THE INVENTION

1. Field of the Invention (Technical Field)

The present invention relates to lactam-bridged melanocortin receptor-specific cyclic peptides which may be used in the treatment of melanocortin receptor-mediated diseases, indications, conditions and syndromes.

2. Description of Related Art

The following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, midbrain and brainstem, and melanocortin-5 receptors (MC5-R), expressed in a wide distribution of peripheral tissues. MC1-R has been suggested to be associated with hair and skin pigmentation and inflammation, MC2-R is believed to mediate steroidogenesis, MC3-R has been suggested to be associated with energy homeostasis, food intake, and inflammation, MC4-R is believed to control feeding behavior, energy homeostasis, and sexual function (e.g. erectile function), and MC5-R has been suggested to be involved in the exocrine gland system.

Significant work has been done in determining the structure of melanocortin receptors, including both the nucleic acid sequences encoding for the receptors and the amino acid sequences constituting the receptors. MC4-R is a G protein-coupled, 7-transmembrane receptor that is believed to be expressed primarily in the brain.

MC4-R inactivation has been shown to result in obesity (Hadley, 1999, *Ann N Y Acad Sci*, 885:1-21). Agouti-related protein (AgRP) is an endogenous compound that has been suggested to be a MC antagonist or an inverse agonist on MC4-R. The α-melanocyte stimulating hormone (α-MSH) is believed to be the principle endogenous MC4-R agonist.

Also peripherally located MC4-R receptors have been suggested to be involved in the control of energy homeostasis, and the role of MC4-R signalling in the vagus nerve and its relevance for treatment of obesity and diabetes is discussed by Gautron et al, *The Journal of Comparative Neurology*, 518:6-24 (2010).

Peptides specific for MC4-R, and secondarily peptides specific for MC3-R, are believed to be useful in regulation of mammalian energy homeostasis, including use as agents for attenuating food intake and body weight gain. MC4-R agonist peptides are believed to be useful for treating sexual dysfunction, including male erectile dysfunction, and for decreasing food intake and body weight gain, such as for treatment of obesity. Such peptides may also be employed for decreasing voluntary ethanol consumption, treatment of drug addictions, and the like. MC4-R agonist peptides, as well as MC3-R agonist peptides, may further be employed for treatment of circulatory shock, ischemia, hemorrhagic shock, inflammatory diseases and related diseases, indications, conditions and syndromes. MC4-R antagonist peptides, by contrast, are believed to be useful for weight gain aid, such as for use in treatment of cachexia, sarcopenia, wasting syndrome or disease, and anorexia. Such peptides may also be employed for treatment of depression and related disorders. (Wikberg et al, *Nature Reviews, Drug Discovery*, 7, 307, (2008); Adan et al, *British J. Pharm.*, 149, 815-827 (2006); Nogueiras et al, *J. Clin., Invest.*, 117(11): 3475-3488 (2007); Maaser et al, *Ann. N.Y. Acad. Sci.*, 1072, 123-134 (2006); Giuliani et al, *British J. Pharm.*, 150, 595-603 (2007); Balbani, *Expert Opin. Ther. Patents*, 17(3), 287-297 (2007); and Navarro et al, *Alcohol. Clin. Exp. Res.*, 29(6), 949-957 (2005)).

Melanocortin receptor-specific cyclic peptides include cyclic α-melanocyte-stimulating hormone ("α-MSH") analog peptides such as Ac-Nle-cyclo(-Asp-His-D-Phe-Arg-Trp-Lys)-NH$_2$ (See U.S. Pat. Nos. 5,674,839 and 5,576,290) and Ac-Nle-cyclo(-Asp-His-D-Phe-Arg-Trp-Lys)-OH (See U.S. Pat. Nos. 6,579,968 and 6,794,489). These and other melanocortin receptor-specific peptides generally contain the central tetrapeptide sequence of native α-MSH, His$^6$-Phe$^7$-Arg$^8$-Trp$^9$ (SEQ ID NO:1), or a mimetic or variation thereof, such as the substitution of D-Phe for Phe'. Other peptides or peptide-like compounds asserted to be specific for one or more melanocortin receptors are disclosed in U.S. Pat. Nos. 5,731,408, 6,054,556, 6,350,430, 6,476,187, 6,600,015, 6,613,874, 6,693,165, 6,699,873, 6,887,846, 6,951,916, 7,008,925, 7,176,279 and 7,517,854; in U.S. published patent application Publication Nos. 2001/0056179, 2002/0143141, 2003/0064921, 2003/0105024, 2003/0212002, 2004/0023859, 2005/0130901, 2005/0187164, 2005/0239711, 2006/0105951, 2006/0111281, 2006/0293223, 2007/0027091, 2007/0105759, 2007/0123453, 2007/0244054, 2008/0004213, 2008/0039387, and 2008/0305152; and in international patent applications nos. WO 98/27113, WO 99/21571, WO 00/05263, WO 99/54358, WO 00/35952, WO 00/58361, WO 01/30808, WO 01/52880, WO 01/74844, WO 01/85930, WO 01/90140, WO 02/18437, WO 02/26774, WO 03/006604, WO 2004/046166, WO 2004/099246, WO 2005/000338, WO 2005/000339, WO 2005/000877, WO 2005/030797, WO 2005/060985, WO 2006/012667, WO 2006/048449, WO 2006/048450, WO 2006/048451, WO 2006/048452, WO 2006/097526, WO 2007/008684, WO 2007/008704, WO 2007/009894, WO 2008/025094, and WO 2009/061411. Melanocortin receptor-specific cyclic peptides disclosed in the foregoing are typically cyclized through a lactam bridge formed by the side chains of Asp (aspartic acid) and Lys (lysine), or alternatively through a disulfide bridge formed by the side chains of two Cys (cysteine) or other reactive thiol-containing residues.

Melanocortin receptor-specific linear peptides are known which contain Glu (glutamic acid) and Orn (ornithine), including certain linear peptides disclosed in WO2008/025094 and U.S. Pat. No. 5,674,839. Cyclic peptides asserted to be specific for one or more melanocortin receptors and containing a Glu and Orn are known, but are peptides in which the cyclic portion thereof consists of seven amino acids, such as those disclosed in U.S. Pat. Nos. 6,951,916 and 6,613,874. In such peptides, there are five amino acids between the Glu and Orn residues, and thus the cyclic peptide ring contains 26 ring atoms.

Melanocortin receptor-specific peptides may be evaluated by a number of parameters, including binding affinities (typically Ki values reported in nM) and various functional measures, such as $EC_{50}$ and $E_{max}$ values. While melanocortin receptor-specific cyclic peptides are reported with nanomolar or subnanomolar Ki values, for pharmaceutical development for many indications it is desired and necessary to optimize functionality, such as $EC_{50}$ and $E_{max}$ values, such that the peptides are agonists, preferably full agonists, more preferably potent full agonists, with nanomolar or subnanomolar $EC_{50}$ values and $E_{max}$ values as high as feasible, such as over about 80%, about 90% or at or over 100%. It is against this background that the present invention was made.

BRIEF SUMMARY OF THE INVENTION

In one aspect, the present invention relates to a cyclic peptide of formula (I):

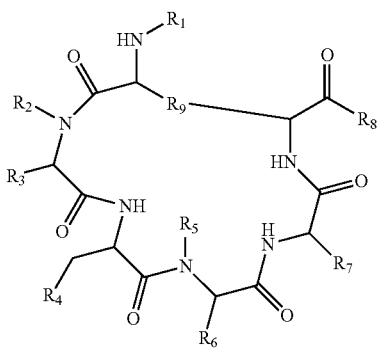
(I)

including all enantiomers, stereoisomers or diastereoisomers thereof, or a pharmaceutically acceptable salt of any of the foregoing,
wherein:
$R_1$ is —$R_{10}$-$R_{11}$;
$R_2$ is —H, —$CH_3$ or —$CH_2$—, and if it is —$CH_2$— forms with $R_3$ a ring of the general structure

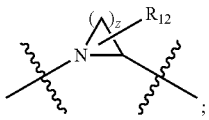
;

$R_3$ is —H, —$(CH_2)_z$— if $R_2$ is —$CH_2$—, and if it is —$(CH_2)_z$— forms the ring with $R_2$, or $R_3$ is —$(CH_2)_w$—$R_{13}$—$(CH_2)_w$—$R_{14}$, wherein any H in either $(CH_2)_w$ is optionally substituted with —$(CH_2)_w$—$CH_3$,
$R_4$ is substituted or unsubstituted phenyl, but excluding substituted phenyl where —$R_{10}$-$R_{11}$ is Ac-Arg-;
$R_5$ is —H, —$CH_3$ or —$CH_2$—, and if it is —$CH_2$— forms with $R_6$ a ring of the general structure

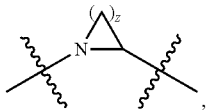
, wherein the ring is optionally substituted;
$R_6$ is —$(CH_2)_z$— if $R_5$ is —$CH_2$—, and if it is —$(CH_2)_z$— forms the ring with $R_5$, or $R_6$ is —$(CH_2)_w$—$R_{15}$;
$R_7$ is —$(CH_2)_z$—$R_{16}$;
$R_8$ is —$R_{17}$-$R_{18}$;
$R_9$ is —$(CH_2)_2$—C(=O)—NH—$(CH_2)_3$— or —$(CH_2)_3$—NH—C(=O)—$(CH_2)_2$—;
$R_{10}$ is optionally present, and if present, is from one to three L- or D-isomer amino acids, or a combination thereof;
$R_{11}$ is H or a $C_1$ to $C_7$ acyl group comprising a linear or branched alkyl, cycloalkyl, alkyl cycloalkyl, aryl or aralkyl;
$R_{12}$ is —H or —$R_{13}$—$(CH_2)_w$—$R_{14}$;
$R_{13}$ is optionally present, and if present is
—O—,
—S—,
—NH—,
—S(=O)$_2$—,
—S(=O)—,
—S(=O)$_2$—NH—,
—NH—S(=O)$_2$—,
—C(=O)—,
—C(=O)—O—,
—O—C(=O)—,
—NH—C(=O)—O—,
—O—C(=O)—NH—,
—NH—C(=O)—, or
—C(=O)—NH—;
$R_{14}$ is
—H,
—$CH_3$,
—N($R_{19a}$)($R_{19b}$),
—NH—$(CH_2)_z$—N($R_{19a}$)($R_{19b}$),
—NH—CH(=NH)—N($R_{19a}$)($R_{19b}$),
—NH—CH(=O)—N($R_{19a}$)($R_{19b}$),
—O($R_{19a}$),
—($R_{19a}$)($R_{19b}$),
—S(=O)$_2$($R_{19a}$),
—C(=O)—O($R_{19a}$), wherein any ring in $R_{14}$ is optionally substituted with one or more ring substituents, and when one or more are present, are the same or different and independently hydroxyl, halogen, sulfonamide, alkyl, —O-alkyl, aryl, —O-aryl, C(=O)—OH, or C(=O)—N($R_{19a}$)($R_{19b}$);

$R_{15}$ is
—H,
—N($R_{19a}$)($R_{19b}$),
—NH—($CH_2$)$_z$—N($R_{19a}$)($R_{19b}$),
—NH—CH(=NH)—N($R_{19a}$)($R_{19b}$),
—NH—CH(=O)—N($R_{19a}$)($R_{19b}$),
—O($R_{19a}$),
—$C_1$ to $C_{17}$ linear, branched or cyclic alkyl chain,
—C(=O)—N($R_{19a}$)($R_{19b}$),
—S(=O)$_2$($R_{19a}$),

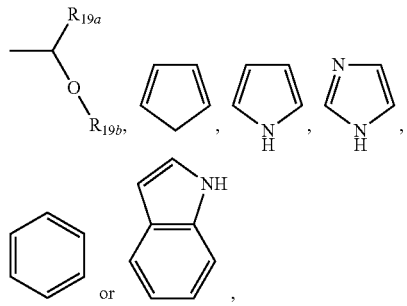

wherein any ring is optionally substituted with one or more optional ring substituents, and when one or more are present, are the same or different and independently hydroxyl, halogen, sulfonamide, alkyl, —O-alkyl, aryl, aralkyl, O-aralkyl, or —O-aryl;

$R_{16}$ is

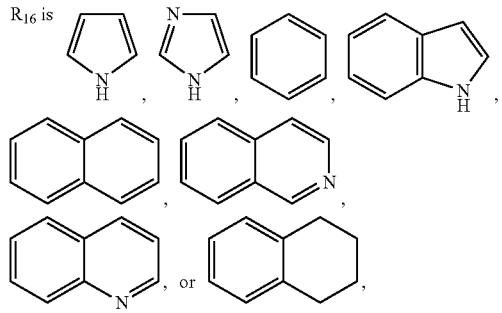

optionally substituted with one or more ring substituents, and when one or more are present, are the same or different and independently hydroxyl, halogen, sulfonamide, alkyl, —O-alkyl, aryl, or —O-aryl;

$R_{17}$ is optionally present, and if present, is from one to three L- or D-isomer amino acids, or a combination thereof;
$R_{18}$ is —OH, —N($R_{19a}$)($R_{19b}$) or —($CH_2$)$_w$-cycloalkyl;
$R_{19a}$ and $R_{19b}$ are each independently H or a $C_1$ to $C_4$ linear, branched or cyclic alkyl chain;
w is in each instance independent 0 to 5; and
z is in each instance independently 1 to 5;
but excluding cyclic peptides wherein $R_{10}$ is L- or D-Arg, $R_{11}$ is Ac, $R_2$ and $R_3$ together form unsubstituted pyrrolidine or $R_3$ is —($CH_2$)$_2$—$NH_2$ or —$CH_2$—O—$CH_2$-phenyl, $R_4$ is unsubstituted phenyl, $R_5$ is H, $R_6$ is —($CH_2$)$_3$—NH—C(=NH)—$NH_2$, $R_7$ is —$CH_2$-indole, $R_{17}$ is not present and $R_{18}$ is —OH or $NH_2$.

In one aspect of the cyclic peptide of formula (I), $R_4$ is unsubstituted phenyl. In another aspect of the cyclic peptide of formula (I), $R_4$ is substituted phenyl. When $R_4$ is substituted phenyl, it may be substituted with between one and three ring substituents wherein the substituents are the same or different, and are each independently halo, ($C_1$-$C_{10}$)alkyl-halo, ($C_1$-$C_{10}$)alkyl, ($C_1$-$C_{10}$)alkoxy, ($C_1$-$C_{10}$)alkylthio, aryl, ($C_1$-$C_{10}$)alkylaryl, aryloxy, nitro, nitrile, sulfonamide, amino, monosubstituted amino, disubstituted amino, hydroxy, carbamoyl, carboxy, carbamoyl, aryloxy-carbonyl, alkoxy-carbonyl, or aryloxy-carbonyl.

In another aspect of the cyclic peptide of formula (I), at least one of $R_{10}$ and $R_{17}$ comprise at least one L- or D-isomer amino acid. In one aspect thereof, $R_{10}$ is a single L- or D-isomer amino acid with an aliphatic side chain and $R_{17}$ is not present. In such aspect, the aliphatic side chain may be —($CH_2$)$_3$—$CH_3$.

In another aspect of the cyclic peptide of formula (I), $R_{10}$ is a single L- or D-isomer amino acid with a side chain comprising at least one nitrogen atom. In such aspect, $R_{10}$ may be an L- or D-isomer of Arg, Lys, Orn, Dab, Dap or Cit.

In another aspect of the cyclic peptide of formula (I), $R_{10}$ and $R_{17}$ each comprise at least one L- or D-isomer amino acid.

In one aspect of the cyclic peptide of formula (I), $R_9$ is —($CH_2$)$_2$—C(=O)—NH—($CH_2$)$_3$—. In another aspect of the cyclic peptide of formula (I), $R_9$ is —($CH_2$)$_3$—NH—C(=O)—($CH_2$)$_2$—.

In another aspect, the invention relates to a cyclic peptide of formula (II):

(II)

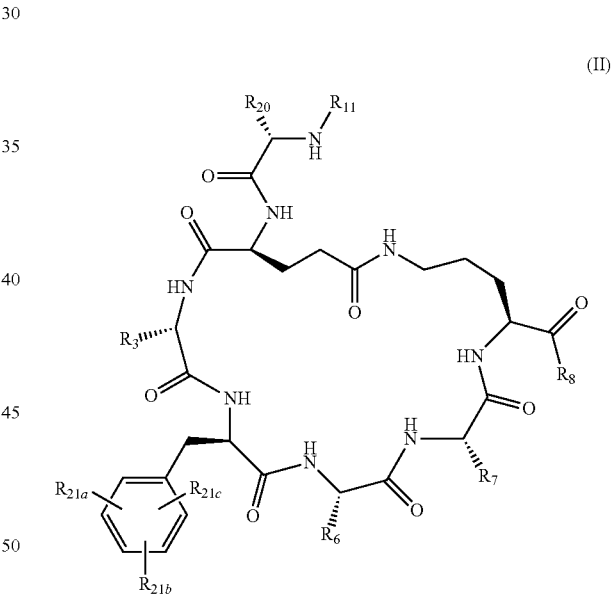

or a pharmaceutically acceptable salt thereof, wherein
$R_{20}$ is linear or branched ($C_1$-$C_{10}$)alkyl, ($C_1$-$C_{10}$)alkyl-N($R_{19a}$)($R_{19b}$), ($C_1$-$C_{10}$)alkyl-NH—($CH_2$)$_z$—N($R_{19a}$)($R_{19b}$), ($C_1$-$C_{10}$)alkyl-NH—C(=NH)—N($R_{19a}$)($R_{19b}$) or ($C_1$-$C_{10}$)alkyl-NH—C(=O)—N($R_{19a}$)($R_{19b}$), wherein any ($C_1$-$C_{10}$)alkyl carbon atom may be optionally substituted with oxo or replaced by oxygen;
$R_{21a}$, $R_{21b}$ and $R_{21c}$ are the same or different, and are each independently hydrogen, halo, ($C_1$-$C_{10}$)alkyl-halo, ($C_1$-$C_{10}$)alkyl, ($C_1$-$C_{10}$)alkoxy, ($C_1$-$C_{10}$)alkylthio, aryl, ($C_1$-$C_{10}$)alkylaryl, aryloxy, nitro, nitrile, sulfonamide, amino, monosubstituted amino, disubstituted amino, hydroxy, carboxy, or alkoxy-carbonyl; and
other variables are as defined for formula (I).

In another aspect, the invention relates to a cyclic peptide of formula (III) or (IV):

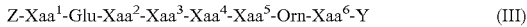

or

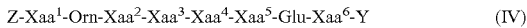

or a pharmaceutically acceptable salt thereof, wherein

Z is H or an N-terminal group;

$Xaa^1$ is optionally present, and if present is from one to three amino acids;

$Xaa^2$ is Pro, optionally substituted with hydroxyl, halogen, sulfonamide, alkyl, —O-alkyl, aryl, alkyl-aryl, alkyl-O-aryl, alkyl-O-alkyl-aryl, or —O-aryl, or $Xaa^3$ is an amino acid with a side chain comprising at least one primary amine, secondary amine, alkyl, cycloalkyl, cycloheteroalkyl, aryl, heteroaryl, ether, sulfide, or carboxyl;

$Xaa^3$ is an amino acid with a side chain comprising substituted or unsubstituted aryl, but excluding L- or D-isomers of substituted Phe wherein Z is Ac and $Xaa^1$ is Arg;

$Xaa^4$ is Pro or $Xaa^4$ is an amino acid with a side chain comprising at least one primary amine, secondary amine, guanidine, urea, alkyl, cycloalkyl, cycloheteroalkyl, aryl, heteroaryl, or ether;

$Xaa^5$ is an amino acid with a side chain comprising at least one aryl or heteroaryl, optionally substituted with one or more ring substituents, and when one or more are present, are the same or different and independently hydroxyl, halogen, sulfonamide, alkyl, —O-alkyl, aryl, or —O-aryl, but excluding substituted D-Phe where $Z-Xaa^1$- is Ac-Arg, $Xaa^6$ is not present and Y is hydroxyl or amide;

$Xaa^6$ is optionally present, and if present is from one to three amino acids; and Y is a C-terminal group;

but excluding cyclic peptides of formula (III) wherein Z is Ac, $Xaa^1$ is Arg, $Xaa^2$ is Pro or Ser(Bzl), $Xaa^3$ is unsubstituted D-Phe, $Xaa^4$ is Arg, $Xaa^5$ is Trp, $Xaa^6$ is not present and Y is —OH or —$NH_2$.

In the cyclic peptide of formula (III) or (IV), $Xaa^1$ may be a single amino acid with a side chain including at least one primary amine, guanidine or urea group, including an L- or D-isomer of Arg, Lys, Orn, Dab, Dap or Cit.

In another aspect of the cyclic peptide of formula (III) or (IV), $Xaa^3$ is D-Phe, optionally substituted with from one to three ring substituents. When substituted, the ring substituents are the same or different, and are each independently halo, $(C_1-C_{10})$alkyl-halo, $(C_1-C_{10})$alkyl, $(C_1-C_{10})$alkoxy, $(C_1-C_{10})$alkylthio, aryl, $(C_1-C_{10})$alkylaryl, aryloxy, nitro, nitrile, sulfonamide, amino, monosubstituted amino, disubstituted amino, hydroxy, carboxy, or alkoxy-carbonyl.

In another aspect there is provided the cyclic peptide of formula (III) or (IV) wherein $Xaa^1$ is Gly or Nle.

In another aspect there is provided the cyclic peptide of formula (III) or (IV) wherein $Xaa^6$ comprises at least one amino acid.

In another aspect there is provided the cyclic peptide of formula (III) or (IV) wherein the N-terminal group is a $C_1$ to $C_7$ acyl group, a linear or branched $C_1$ to $C_{17}$ alkyl, aryl, heteroaryl, alkene, alkenyl, or aralkyl chain or an N-acylated linear or branched $C_1$ to $C_{17}$ alkyl, aryl, heteroaryl, alkene, alkenyl, or aralkyl chain.

In another aspect there is provided the cyclic peptide of formula (III) or (IV) wherein Y is a hydroxyl, an amide, or an amide substituted with one or two linear or branched $C_1$ to $C_{17}$ alkyl, cycloalkyl, aryl, aryl cycloalkyl, aralkyl, heteroaryl, alkene, alkenyl, or aralkyl chains.

In another aspect, the present invention provides peptides with increased functionality compared to peptides with conventional Asp . . . Lys lactam bridges or peptides cyclized through a disulfide bridge, such increased functionality including $EC_{50}$ and $E_{max}$ values.

In another aspect, the present invention provides a melanocortin receptor-specific peptide-based pharmaceutical composition for use in treatment of melanocortin receptor-mediated diseases, indications, conditions and syndromes.

In another aspect, the present invention provides a peptide-based melanocortin receptor-specific pharmaceutical, wherein the peptide is selective for MC4-R, for use in treatment of sexual dysfunction and other MC4-R associated disorders.

In another aspect, the present invention provides peptides which are specific for MC4-R and which are agonists.

In another aspect, the present invention provides a specific MC4-R cyclic peptide that is effective over a significant dose range.

Other aspects and novel features, and the further scope of applicability of the present invention will be set forth in part in the detailed description to follow, and in part will become apparent to those skilled in the art upon examination of the following, or may be learned by practice of the invention. The aspects of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serves to explain the principles of the invention. The drawings are only for the purpose of illustrating one or more preferred embodiments of the invention and are not to be construed as limiting the invention.

Figure 1:
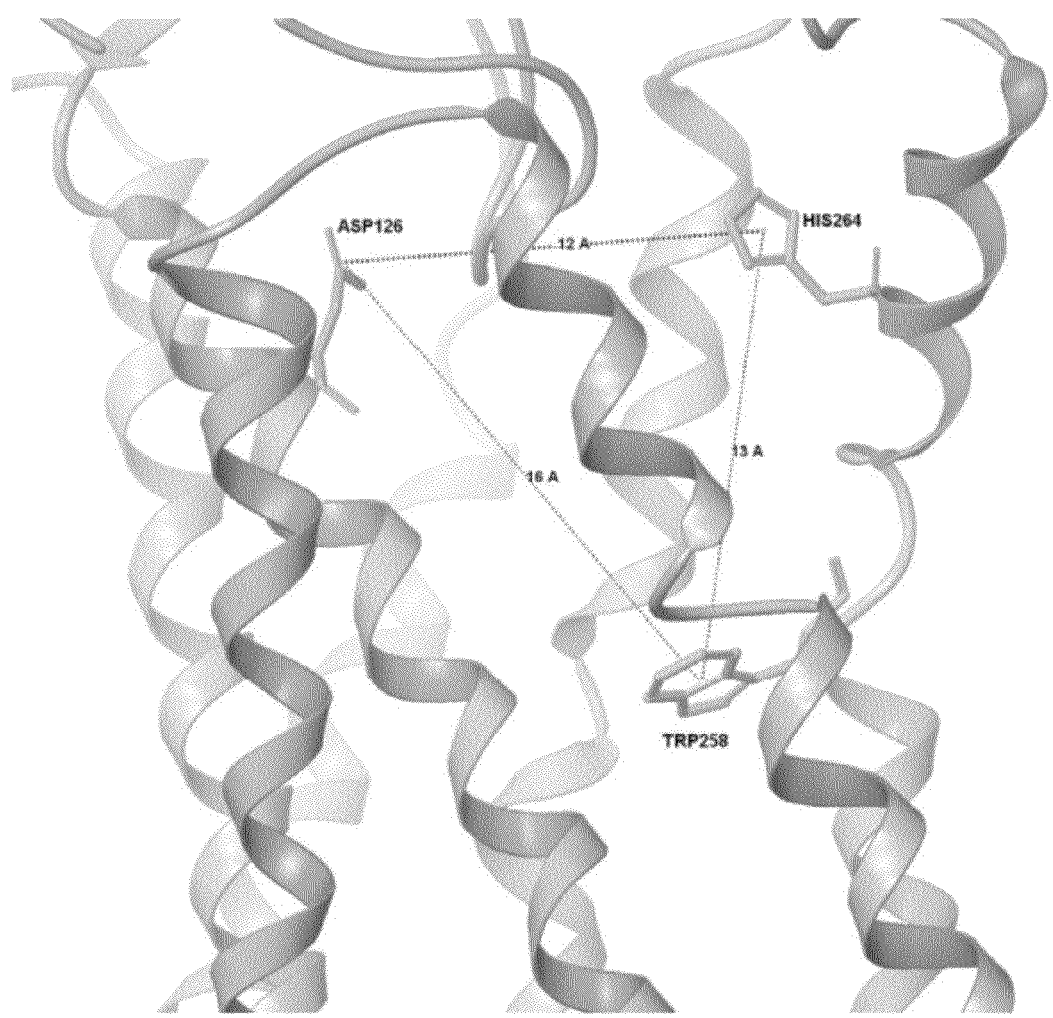
FIG. 1 is a cartoon model illustration of a pharmacophore model for MC4-R agonists, with three key receptor residues, $Asp^{126}$, $Trp^{258}$ and $His^{264}$, shown on their respective tube models.

DETAILED DESCRIPTION OF THE INVENTION 1.0 Definitions

Before proceeding with the description of the invention, certain terms are defined as set forth herein.

In the sequences given for the peptides according to the present invention, the amino acid residues have their conventional meaning as given in Chapter 2400 of the *Manual of Patent Examining Procedure*, 8$^{th}$ Ed. Thus, "Ala" is alanine, "Asn" is asparagine, "Asp" is aspartic acid, "Arg" is arginine, "Cys" is cysteine, "Gly" is glycine, "Gln" is glutamine, "Glu" is glutamic acid, "His" is histidine, "Ile" is isoleucine, "Leu" is leucine, "Lys" is lysine, "Met" is methionine, "Phe" is phenylalanine, "Pro" is proline, "Ser" is serine, "Thr" is Threonine, "Trp" is tryptophan, "Tyr" is tyrosine, and "Val" is valine, and so on. It is to be understood that "D" isomers are designated by a "D-" before the three letter code or amino acid name, such that for example D-Phe is D-phenylalanine. Amino acid residues not encompassed by the foregoing have the following definitions:

| Abbreviation | Common Name | Side Chain or Amino Acid Structure |
|---|---|---|
| Cit | citrulline | |
| Dab | diaminobutyric acid | |
| Dab(Acetyl) | 2-amino, 4-acetylamino-butyric acid | |
| Dap | diamino-proprionic acid | |
| Hyp | hydroxyproline | |
| Met($O_2$) | methionine sulfone | |
| Nal 1 | 3-(1-naphthyl) alanine | |
| Nal 2 | 3-(2-naphthyl) alanine | |
| Nle | norleucine | |
| Orn | ornithine | |
| Phe(2-$CF_3$) | 2-trifluoromethyl phenylalanine | |
| Phe(2-C(=O)-$NH_2$) | 2-carbamoyl-phenylalanine | |
| Phe(2-Me) | 2-methyl phenylalanine | |
| Phe(2-CN) | 2-cyano phenylalanine | |
| Phe(2-Cl) | 2-chloro phenylalanine | |
| Phe(2,4-diCl) | 2,4-dichloro phenylalanine | |
| Phe(2,4-diMe) | 2,4-dimethyl phenylalanine | |

| Abbreviation | Common Name | Side Chain or Amino Acid Structure |
|---|---|---|
| Phe(2-F) | 2-fluoro phenylalanine | 2-fluorobenzyl |
| Phe(2-NO₂) | 2-nitro phenylalanine | 2-nitrobenzyl |
| Phe(3-CF₃) | 3-trifluoromethyl phenylalanine | 3-(trifluoromethyl)benzyl |
| Phe(3-C(=O)—NH₂) | 3-carbamoyl-phenylalanine | 3-carbamoylbenzyl |
| Phe(3-CN) | 3-cyano phenylalanine | 3-cyanobenzyl |
| Phe(3-Cl) | 3-chloro phenylalanine | 3-chlorobenzyl |
| Phe(3,4-diCl) | 3,4-dichloro phenylalanine | 3,4-dichlorobenzyl |
| Phe(3-F) | 3-fluoro phenylalanine | 3-fluorobenzyl |
| Phe(3,4,5-triF) | 3,4,5-trifluoro phenylalanine | 3,4,5-trifluorobenzyl |
| Phe(3,4-diF) | 3,4-difluoro phenylalanine | 3,4-difluorobenzyl |
| Phe(3,5-diF) | 3,5-difluoro phenylalanine | 3,5-difluorobenzyl |
| Phe(3-Me) | 3-methyl phenylalanine | 3-methylbenzyl |
| Phe(3-NO₂) | 3-nitro phenylalanine | 3-nitrobenzyl |
| Phe(3,4-diOMe) | 3,4-dimethoxy phenylalanine | 3,4-dimethoxybenzyl |
| Phe(4-C(=O)—NH₂) | 4-carbamoyl-phenylalanine | 4-carbamoylbenzyl |
| Phe(4-Me) | 4-methyl phenylalanine | 4-methylbenzyl |
| Phe(4-CF₃) | 4-trifluoromethyl phenylalanine | 4-(trifluoromethyl)benzyl |
| Phe(4-CN) | 4-cyano phenylalanine | 4-cyanobenzyl |
| Phe(4-Cl) | 4-chloro phenylalanine | 4-chlorobenzyl |
| Phe(4-F) | 4-fluoro phenylalanine | 4-fluorobenzyl |
| Phe(4-NH₂) | 4-amino phenylalanine | 4-aminobenzyl |
| Phe(4-NO₂) | 4-nitro phenylalanine | 4-nitrobenzyl |
| Phe(4-Ph) | 4-phenyl phenylalanine | 4-phenylbenzyl |

| Abbreviation | Common Name | Side Chain or Amino Acid Structure |
|---|---|---|
| Phe(4-OMe) | 4-methoxy phenylalanine | |
| Phe(4-tBu) | 4-tert butyl phenylalanine | |
| Ser(Bzl) | O-benzyl-serine | |
| Thr(OBzl) | O-benzyl-threonine | |

The term "acyl" includes a group R(C=O)—, where R is an organic group, such as an alkyl, aryl, heteroaryl, carbocyclyl or heterocyclyl. Thus, when reference is made herein to a substituted acyl group, it means that said organic group (R) is substituted. The acetyl group $CH_3$—C(=O)—, referred to herein as "Ac", is non-limiting example of an acyl.

A peptide or aliphatic moiety is "acylated" when an alkyl or substituted alkyl group as defined above is bonded through one or more carbonyl {—(C=O)—} groups. A peptide is most usually acylated at the N-terminus.

The term "alkane" includes linear or branched saturated hydrocarbons. Examples of linear alkane groups include methane, ethane, propane, and the like. Examples of branched or substituted alkane groups include methylbutane or dimethylbutane, methylpentane, dimethylpentane or trimethylpentane, and the like. In general, any alkyl group may be a substituent of an alkane.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length which are either straight or branched chain saturated aliphatic hydrocarbon groups. $C_{1-10}$ alkyl means an alkyl having from 1 to 10 carbon atoms. Non-limiting examples of such alkyl radicals include methyl, ethyl, propyl, isopropyl, butyl, sec-butyl, tertiary butyl, pentyl, isopentyl, hexyl, isohexyl, and the like.

The term "alkyne" includes a linear monovalent hydrocarbon radical of two to six carbon atoms or a branched monovalent hydrocarbon radical of three to six carbon atoms containing at least one triple bond; examples thereof include ethyne, propyne, butyne, and the like.

The term "aryl" includes a monocyclic or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical —$R^aR^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

As used herein, the term "amide" includes compounds that have a trivalent nitrogen attached to a carbonyl group, i.e. —C(=O)—$NH_2$ (i.e. primary amide), —C(=O)—$NHR_c$ and —C(=O)—$NR_cR_d$, wherein each of $R_c$ and $R_d$ independently represents an organic group. When reference is made herein to a substituted amide group, it means that at least one of said organic groups ($R_c$ and $R_d$) is substituted. Examples of amides include methylamide, ethylamide, propylamide, and the like.

An "amine" includes an amino group (—$NH_2$), —$NHR_a$ and —$NR_aR_b$, wherein each of $R_a$ and $R_b$ independently represents an organic group. When reference is made herein to a substituted amine group, it means that at least one of the organic groups ($R_a$ and $R_b$) is substituted.

The abbreviation "cycProp" refers to the group cyclic propyl.

A "nitrile" includes compounds that are carboxylic acid derivatives and contain a (—CN) group bound to an organic group.

The term "halogen" is intended to include the halogen atoms fluorine, chlorine, bromine and iodine, and groups including one or more halogen atoms, such as —$CF_3$ and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions utilized in the present invention encompass any composition made by admixing an active ingredient and one or more pharmaceutically acceptable carriers.

By a melanocortin receptor "agonist" is meant an endogenous substance, drug substance or compound, including a compound such as the peptides of the present invention, which can interact with a melanocortin receptor and initiate a pharmacological response, including but not limited to adenyl cyclase activation, characteristic of the melanocortin receptor. A melanocortin receptor agonist may be an agonist at one or more of melanocortin-4 receptor (MC4-R), melanocortin-1 receptor (MC1-R), melanocortin-3 receptor (MC3-R) and melanocortin-5 receptor (MC5-R).

By "α-MSH" is meant the peptide Ac-Ser-Tyr-Ser-Met-Glu-His-Phe-Arg-Trp-Gly-Lys-Pro-Val-$NH_2$ (SEQ ID NO:2) and analogs and homologs thereof, including without limitation NDP-α-MSH.

By "NDP-α-MSH" is meant the peptide Ac-Ser-Tyr-Ser-Nle-Glu-His-D-Phe-Arg-Trp-Gly-Lys-Pro-Val-$NH_2$ and analogs and homologs thereof.

By "EC$_{50}$" is meant the molar concentration of an agonist, including a partial agonist, which produced 50% of the maximum possible response for that agonist. By way of example, a test compound which, at a concentration of 72 nM, produces 50% of the maximum possible response for that compound as determined in a cAMP assay in an MC4-R cell expression system has an EC$_{50}$ of 72 nM. Unless otherwise specified, the molar concentration associated with an EC$_{50}$ determination is in nanomoles per liter (nM).

By "Ki (nM)" is meant the equilibrium inhibitor dissociation constant representing the molar concentration of a competing compound that binds to half the binding sites of a receptor at equilibrium in the absence of radioligand or other competitors. In general, the numeric value of the Ki is inversely correlated to the affinity of the compound for the receptor, such that if the Ki is low, the affinity is high. Ki may be determined using the equation of Cheng and Prusoff (Cheng Y., Prusoff W. H., *Biochem. Pharmacol.* 22: 3099-3108, 1973):

$$Ki = \frac{EC_{50}}{1 + \frac{[\text{ligand}]}{K_D}}$$

where "ligand" is the concentration of radioligand and K$_D$ is an inverse measure of receptor affinity for the radioligand which produces 50% receptor occupancy by the radioligand. Unless otherwise specified, the molar concentration associated with a Ki determination is in nM. Ki may be expressed in terms of specific receptors (e.g., MC1-R, MC3-R, MC4-R or MC5-R) and specific ligands (e.g., α-MSH or NDP-α-MSH).

By "inhibition" is meant the percent attenuation, or decrease in receptor binding, in a competitive inhibition assay compared to a known standard. Thus, by "inhibition at 1 μM (NDP-α-MSH)" is meant the percent decrease in binding of NDP-α-MSH by addition of a determined amount of the compound to be tested, such as 1 μM of a test compound, such as under the assay conditions hereafter described. By way of example, a test compound that does not inhibit binding of NDP-α-MSH has a 0% inhibition, and a test compound that completely inhibits binding of NDP-α-MSH has a 100% inhibition. Typically, as described hereafter, a radio assay is used for competitive inhibition testing, such as with I$^{125}$-labeled NDP-α-MSH, or a lanthanide chelate fluorescent assay, such as with Eu-NDP-α-MSH. However, other methods of testing competitive inhibition are known, including use of label or tag systems other than radioisotopes, and in general any method known in the art for testing competitive inhibition may be employed in this invention. It may thus be seen that "inhibition" is one measure to determine whether a test compound attenuates binding of α-MSH to melanocortin receptors.

By "binding affinity" is meant the ability of a compound or drug to bind to its biological target, expressed herein as Ki (nM).

By "E$_{max}$" is meant the maximal functional activity achievable by a compound in a specified melanocortin receptor expressing cell system, such as the maximal stimulation of adenylyl cyclase. The maximal stimulation achieved by NDP-α-MSH is designated as an E$_{max}$ of 100% and a compound capable of stimulating half the maximal activity of NDP-α-MSH is designated as having an E$_{max}$ of 50%. A compound of this invention that under assay conditions described herein has an E$_{max}$ of 70% or higher is classified as an agonist, a compound with an E$_{max}$ between 10% and 70% is classified as a partial agonist, and a compound with an E$_{max}$ below 10% is classified as inactive.

In general, "functional activity" is a measure of the signaling of a receptor, or measure of a change in receptor-associated signaling, such as a melanocortin receptor, and in particular MC4-R or hMC4-R, upon activation by a compound. Melanocortin receptors initiate signal transduction through activation of heterotrimeric G proteins. In one aspect, melanocortin receptors signal through Gα$_S$, which catalyzes production of cAMP by adenylyl cyclase. Thus determination of stimulation of adenylyl cyclase, such as determination of maximal stimulation of adenylyl cyclase, is one measure of functional activity, and is the primary measure exemplified herein. However, it is to be understood that alternative measures of functional activity may be employed in the practice of this invention, and are specifically contemplated and included within the scope of this invention. Thus, in one example intracellular free calcium may be measured, such as reported by and using the methods disclosed in Mountjoy K. G. et al., Melanocortin receptor-medicated mobilization of intracellular free calcium in HEK293 cells. *Physiol Genomics* 5:11-19, 2001, or Kassack M. U. et al., Functional screening of G protein-coupled receptors by measuring intracellular calcium with a fluorescence microplate reader. *Biomol Screening* 7:233-246, 2002. It is also possible to measure activation by measurement of the production of inositol triphosphate or diacylglycerol from phosphatidylinositol 4,5-biphosphate, such as by use of radioassays. Yet another measure of functional activity is receptor internalization, resulting from activation of regulatory pathways, such as using the methods disclosed in Nickolls S. A. et al., Functional selectivity of melanocortin 4 receptor peptide and nonpeptide agonists: evidence for ligand specific conformational states. *J Pharm Exper Therapeutics* 313:1281-1288, 2005. Yet another measure of functional activity is the exchange, and exchange rate, of nucleotides associated with activation of a G protein receptor, such as the exchange of GDP (guanosine diphosphate) for GTP (guanosine triphosphase) on the G protein α subunit, which may be measured by any number of means, including a radioassay using guanosine 5'-(γ-[$^{35}$S]thio)-triphosphate, as disclosed in Manning D. R., Measures of efficacy using G proteins as endpoints: differential engagement of G proteins through single receptors. *Mol Pharmacol* 62:451-452, 2002. Various gene-based assays have been developed for measuring activation of G-coupled proteins, such as those disclosed in Chen W. et al., A colorimetric assay from measuring activation of Gs- and Gq-coupled signaling pathways. *Anal Biochem* 226:349-354, 1995; Kent T. C. et al., Development of a generic dual-reporter gene assay for screening G-protein-coupled receptors. *Biomol Screening,* 5:437-446, 2005; or Kotarsky K. et al., Improved receptor gene assays used to identify ligands acting on orphan seven-transmembrane receptors. *Pharmacology & Toxicology* 93:249-258, 2003. The colorimetric assay of Chen et al. has been adapted for use in measuring melanocortin receptor activation, as disclosed in Hruby V. J. et al., Cyclic lactam α-melanocortin analogues of Ac-Nle$^4$-cyclo[Asp$^5$,D-Phe$^7$, Lys$^{10}$]α-melanocyte-stimulating hormone-(4-10)-NH$_2$ with bulky aromatic amino acids at position 7 shows high antagonist potency and selectivity at specific melanocortin receptors. *J Med Chem* 38:3454-3461, 1995. In general, functional activity may be measured by any method, including methods of determining activation and/or signaling of a G-coupled receptor, and further including methods which may be here-after developed or reported. Each of the foregoing articles, and the methods disclosed therein, is incorporated here by reference as if set forth in full.

The terms "treat," "treating" and "treatment," as used herein, contemplate an action that occurs while a patient is suffering from the specified disease or disorder, which reduces the severity of the disease or disorder.

As used herein, the term "pharmacologically effective amount" (including "therapeutically effective amount") means an amount of a peptide according to the invention that is sufficient to induce a desired therapeutic or biological effect.

As used herein, the term "therapeutically effective amount" means the amount of a compound including a peptide of the invention that will elicit a biological or medical response in the mammal that is being treated by a medical doctor or other clinician.

As used herein, the term "prophylactically effective" or "preventive" means the amount of a compound including a peptide of the invention that will prevent or inhibit affliction or mitigate affliction of a mammal with a medical condition that a medical doctor or other clinician is trying to prevent, inhibit, or mitigate before a patient begins to suffer from the specified disease or disorder.

The term "obesity" means the condition of excess body fat (adipose tissue), including by way of example in accordance with the National Institutes of Health Federal Obesity Clinical Guidelines for adults, whereby body mass index calculated by dividing body mass in kilograms by height in meters squared is equal to or greater than twenty-five (25), and further including an overweight condition and comparable obesity and overweight condition in children.

The term "diabetes" includes type 1 diabetes, which is insulin-dependent diabetes mellitus as diagnosed according to criteria published in the Report of the Expert Committee on the Diagnosis and Classification of Diabetes Mellitus (*Diabetes Care*, Vol. 24, Supp. 1, January 2001) whereby fasting plasma glucose level is greater than or equal to 126 milligrams per deciliter and for which the primary cause is pancreatic beta cell destruction, type 2 diabetes, which is non-insulin-dependent diabetes mellitus as diagnosed according to criteria published in the Report of the Expert Committee on the Diagnosis and Classification of Diabetes Mellitus whereby fasting plasma glucose level is greater than or equal to 126 milligrams per deciliter, and latent autoimmune diabetes mellitus of adults.

The term "metabolic syndrome" refers to metabolic disorders, particularly glucose and lipid regulatory disorders, including insulin resistance and defective secretion of insulin by pancreatic beta cells, and may further include conditions and states such as abdominal obesity, dyslipidemia, hypertension, glucose intolerance or a prothrombitic state, and which may further result in disorders such as hyperlipidemia, obesity, diabetes, insulin resistance, glucose intolerance, hyperglycemia, and hypertension.

"Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes erectile dysfunction in a male mammal and female sexual dysfunction in a female mammal.

"Erectile dysfunction" is a disorder involving the failure of a male mammal to achieve functional erection, ejaculation, or both. Erectile dysfunction is accordingly synonymous with impotence, and includes the inability to attain or sustain an erection of sufficient rigidity for coitus. Symptoms of erectile dysfunction include an inability to achieve or maintain an erection, ejaculatory failure, premature ejaculation, or inability to achieve an orgasm. An increase in erectile dysfunction is often associated with age or may be caused by a physical disease or as a side-effect of drug treatment.

"Female sexual dysfunction" is a disorder including sexual arousal disorder. The term "sexual arousal disorder" includes a persistent or recurrent failure to attain or maintain the lubrication-swelling response of sexual excitement until completion of sexual activity. Sexual dysfunction in females can also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, female sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be caused by boredom or unhappiness in a long-standing relationship, depression, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Female sexual arousal disorder can be caused by reduced estrogen, illness, treatment with diuretics, antihistamines, antidepressants, or antihypertensive agents, or can have other causes. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

Throughout the specification and claims, reference to "Asp . . . Lys" is to be understood to refer to cyclization of a peptide through the side chains of Asp and Lys, with the " . . . " representing the amino acid residues within the cyclic portion of the peptide, "Glu . . . Orn" is to be understood to refer to cyclization of a peptide through the side chains of Glu and Orn, and "Orn . . . Glu" is to be understood to refer to cyclization of a peptide through the side chains of Orn and Glu (in each instance conventionally orienting the peptide in an N-terminus to C-terminus sequence).

2.0 Clinical Indications and Utility

The compositions and methods disclosed herein can be used for both medical applications and animal husbandry or veterinary applications. Typically, the methods are used in humans, but may also be used in other mammals. The term "patient" is intended to denote a mammalian individual, and is so used throughout the specification and in the claims. The primary applications of the present invention involve human patients, but the present invention may be applied to laboratory, farm, zoo, wildlife, pet, sport or other animals. Clinical indications and specific utilities include the following:

2.1 Obesity and Related Metabolic Syndrome.

Peptides of formulas (I), (II), (III) and (IV) have been found to be ligands of the MC4 receptor. In particular, peptides of formulas (I), (II), (III) and (IV) are believed to be useful in treating diseases, disorders and/or conditions responsive to modulation of the MC4-R function, more particularly activation of the MC4-R, i.e. diseases, disorders and/or conditions which would benefit from agonism (including full or partial agonism) at the MC4-R, including energy homeostasis and metabolism related (such as diabetes, in particular type 2 diabetes; dyslipidemia; fatty liver; hypercholesterolemia; hypertriglyceridemia; hyperuricacidemia; impaired glucose tolerance; impaired fasting glucose; insulin resistance syndrome; and metabolic syndrome), food intake related (such as hyperphagia; binge eating; bulimia; and compulsive eating) and/or energy balance and body weight related diseases, disorders and/or conditions, more particularly such diseases, disorders and conditions characterized by excess body weight and/or excess food intake.

Peptides of formulas (I), (II), (III) and (IV) are believed to be useful for treatment of body weight related diseases, disorders and/or conditions characterized by excess body weight, including obesity and overweight (by promotion of weight loss, maintenance of weight loss, and/or prevention of weight gain, including medication-induced weight gain or weight gain subsequent to cessation of smoking), and diseases, disorders and/or conditions associated with obesity and/or overweight, such as insulin resistance; impaired glucose tolerance; type 2 diabetes; metabolic syndrome; dyslipidemia (including hyperlipidemia); hypertension; heart disorders (e.g. coronary heart disease, myocardial infarction); cardiovascular disorders; non-alcoholic fatty liver disease (including non-alcoholic steatohepatitis); joint disorders (including secondary osteoarthritis); gastroesophageal reflux; sleep apnea; atherosclerosis; stroke; macro and micro vascular diseases; steatosis (e.g. in the liver); gall stones; and gallbladder disorders.

2.2 Sexual Dysfunction.

Peptides, compositions and methods of the present invention may be employed for the treatment of sexual dysfunction, including both male erectile dysfunction and female sexual dysfunction. In one particular embodiment, the peptides, compositions and methods of the present invention are used in male patients to increase erectile function, including but not limiting to increasing erectile function so as to permit vaginal intercourse. In another particular embodiment, the peptides, compositions and methods of the present invention are used to treat female sexual dysfunction, including but not limited to an increase in arousal success rate, desire success rate, levels of arousal and desire. For female sexual dysfunction, endpoints may, but need not, be determined by any of a number of validated instruments, including but not limited to the Female Sexual Distress Scale, Female Sexual Encounter Profile, Female Sexual Function Index, and Global Assessment Questionnaire. Patients treated for female sexual dysfunction may be premenopausal women or postmenopausal women.

2.3 Other Indications

Peptides of the invention might also be useful for (i) prevention of organ or tissue damage caused by hypoperfusion due to vessel occlusion (e.g. caused by thrombosis), hemorrhage, trauma, surgery, hemorrhagic shock, cardiogenic shock, toxic shock or septic shock (ii) occlusive, hemorrhagic, traumatic or surgical organ and/or tissue damage, such as myocardial infarction and stroke, (iii) hemorrhagic or cardiogenic shock, or (iv) ocular indications including ureitis or dry eye, among other indications.

According to a further aspect of the invention, there is provided a peptide of formulas (I), (II), (III) and (IV) as previously defined for use as a medicament.

In another aspect, the invention provides the use of a peptide of formulas (I), (II), (III) and (IV) for treatment of diseases, disorders and/or conditions responsive to modulation of the MC4-R.

3.0 Combination Therapy for Certain Indications

The peptides, compositions and methods of the present invention may be used for treatment of any of the foregoing diseases, indications, conditions or syndromes, or any disease, indication, condition or syndrome which is melanocortin receptor mediated, by administration in combination with one or more other pharmaceutically active peptides. Such combination administration may be by means of a single dosage form which includes both a peptide of the present invention and one more other pharmaceutically active compound, such single dosage form including a tablet, capsule, spray, inhalation powder, injectable liquid or the like. Alternatively, combination administration may be by means of administration of two different dosage forms, with one dosage form containing a peptide of the present invention, and the other dosage form including another pharmaceutically active compound. In this instance, the dosage forms may be the same or different. Without meaning to limit combination therapies, the following exemplifies certain combination therapies which may be employed.

3.1 Combination Therapy for Obesity and Related Metabolic Syndrome.

One or more peptides of the invention may be combined with one or more other pharmacologically active agent(s) that is (are) useful in the treatment of various weight and feeding-related disorders, such as obesity and/or overweight, in particular other anti-obesity drugs that affect energy expenditure, glycolysis, gluconeogenesis, glucogenolysis, lipolysis, lipogenesis, fat absorption, fat storage, fat excretion, hunger and/or satiety and/or craving mechanisms, appetite/motivation, food intake, or gastrointestinal motility. Drugs that reduce energy intake include, in part, various pharmacological agents, referred to as anorectic drugs, which are used as adjuncts to behavioral therapy in weight reduction programs.

Generally, a total dosage of the below-described obesity control agents or medications, when used in combination with one or more peptides of the present invention can range from 0.1 to 3,000 mg/day, preferably from about 1 to 1,000 mg/day and more preferably from about 1 to 200 mg/day in single or 2-4 divided doses. The exact dose, however, is determined by the attending clinician and is dependent on such factors as the potency of the compound administered, the age, weight, condition and response of the patient.

One or more peptides of the invention may be combined with one or more other pharmacologically active agent(s) that is (are) useful in the treatment of diabetes, such as other anti-diabetic drugs. One or more peptides of the invention may in addition or alternatively further be combined with one or more other pharmacologically active agent(s) that is (are) useful in the treatment of diseaeses, disorders and/or conditions associated with obesity and/or overweight, such as insulin resistance; impaired glucose tolerance; type 2 diabetes; metabolic syndrome; dyslipidemia (including hyperlipidemia); hypertension; heart disorders (e.g. coronary heart disease, myocardial infarction); cardiovascular disorders; non-alcoholic fatty liver disease (including non-alcoholic steatohepatitis); joint disorders (including secondary osteoarthritis); gastroesophageal reflux; sleep apnea; atherosclerosis; stroke; macro and micro vascular diseases; steatosis (e.g. in the liver); gall stones; and gallbladder disorders.

According to a further aspect of the invention there is provided a combination treatment comprising the administration of a pharmacologically effective amount of a peptide according to the invention, or a pharmaceutically acceptable salt thereof, optionally together with a pharmaceutically acceptable diluent or carrier, with the simultaneous, sequential or separate administration one or more of the following agents selected from:

insulin and insulin analogues;
insulin secretagogues, including sulphonylureas (e.g. glipizide) and prandial glucose regulators (sometimes called "short-acting secretagogues"), such as meglitinides (e.g. repaglinide and nateglinide);

agents that improve incretin action, for example dipeptidyl peptidase IV (DPP-4) inhibitors (e.g. vildagliptin, saxagliptin, and sitagliptin), and glucagon-like peptide-1 (GLP-1) agonists (e.g. exenatide);

insulin sensitising agents including peroxisome proliferator activated receptor gamma (PPARγ) agonists, such as thiazolidinediones (e.g. pioglitazone and rosiglitazone), and agents with any combination of PPAR alpha, gamma and delta activity;

agents that modulate hepatic glucose balance, for example biguanides (e.g. metformin), fructose 1,6-bisphosphatase inhibitors, glycogen phopsphorylase inhibitors, glycogen synthase kinase inhibitors, and glucokinase activators;

agents designed to reduce/slow the absorption of glucose from the intestine, such as alpha-glucosidase inhibitors (e.g. miglitol and acarbose);

agents which antagonise the actions of or reduce secretion of glucagon, such as amylin analogues (e.g. pramlintide);

agents that prevent the reabsorption of glucose by the kidney, such as sodium-dependent glucose transporter 2 (SGLT-2) inhibitors (e.g. dapagliflozin);

agents designed to treat the complications of prolonged hyperglycaemia, such as aldose reductase inhibitors (e.g. epalrestat and ranirestat); and agents used to treat complications related to micro-angiopathies;

anti-dyslipidemia agents, such as HMG-CoA reductase inhibitors (statins, e.g. rosuvastatin) and other cholesterol-lowering agents; PPARα agonists (fibrates, e.g. gemfibrozil and fenofibrate); bile acid sequestrants (e.g. cholestyramine); cholesterol absorption inhibitors (e.g. plant sterols (i.e. phytosterols), synthetic inhibitors); cholesteryl ester transfer protein (CETP) inhibitors; inhibitors of the ileal bile acid transport system (IBAT inhibitors); bile acid binding resins; nicotinic acid (niacin) and analogues thereof; anti-oxidants, such as probucol; and omega-3 fatty acids;

antihypertensive agents, including adrenergic receptor antagonists, such as beta blockers (e.g. atenolol), alpha blockers (e.g. doxazosin), and mixed alpha/beta blockers (e.g. labetalol); adrenergic receptor agonists, including alpha-2 agonists (e.g. clonidine); angiotensin converting enzyme (ACE) inhibitors (e.g. lisinopril), calcium channel blockers, such as dihydropridines (e.g. nifedipine), phenylalkylamines (e.g. verapamil), and benzothiazepines (e.g. diltiazem); angiotensin II receptor antagonists (e.g. candesartan); aldosterone receptor antagonists (e.g. eplerenone); centrally acting adrenergic drugs, such as central alpha agonists (e.g. clonidine); and diuretic agents (e.g. furosemide);

haemostasis modulators, including antithrombotics, such as activators of fibrinolysis; thrombin antagonists; factor VIIa inhibitors; anticoagulants, such as vitamin K antagonists (e.g. warfarin), heparin and low molecular weight analogues thereof, factor Xa inhibitors, and direct thrombin inhibitors (e.g. argatroban); antiplatelet agents, such as cyclooxygenase inhibitors (e.g. aspirin), adenosine diphosphate (ADP) receptor inhibitors (e.g. clopidogrel), phosphodiesterase inhibitors (e.g. cilostazol), glycoprotein IIB/IIA inhibitors (e.g. tirofiban), and adenosine reuptake inhibitors (e.g. dipyridamole);

anti-obesity agents, such as appetite suppressant (e.g. ephedrine), including noradrenergic agents (e.g. phentermine) and serotonergic agents (e.g. sibutramine), pancreatic lipase inhibitors (e.g. orlistat), microsomal transfer protein (MTP) modulators, diacyl glycerolacyl-transferase (DGAT) inhibitors, and cannabinoid (CB1) receptor antagonists (e.g. rimonabant);

feeding behavior modifying agents, such as orexin receptor modulators and melanin-concentrating hormone (MCH) modulators;

glucagon like peptide-1 (GLP-1) receptor modulators;

neuropeptideY (NPY)/NPY receptor modulators;

pyruvate dehydrogenase kinase (PDK) modulators;

serotonin receptor modulators;

leptin/leptin receptor modulators;

ghrelin/ghrelin receptor modulators; or monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRI), triple monoamine reuptake blockers (e.g. tesofensine), and monoamine oxidase inhibitors (MAOI) (e.g. toloxatone and amiflamine), or a pharmaceutically acceptable salt, solvate, solvate of such a salt or a prodrug thereof, optionally together with a pharmaceutically acceptable carrier to a mammal, such as man, in need of such therapeutic treatment.

According to an additional further aspect of the present invention there is provided a combination treatment comprising the administration of a pharmacologically effective amount of a compound according to the invention, or a pharmaceutically acceptable salt thereof, optionally together with a pharmaceutically acceptable carrier, with the simultaneous, sequential or separate administration of very low calorie diets (VLCD) or low-calorie diets (LCD).

3.2 Combination Therapy for Sexual Dysfunction.

It is also possible and contemplated to use cyclic peptides of the present invention in combination with other drugs or agents, such as for treatment of sexual dysfunction. These other drugs and agents may include agents that induce erectile activity, including phosphodiesterase-5 (PDE-5) inhibitors, testosterone, prostaglandin and the like. In a preferred embodiment of the invention, cyclic peptides of the invention are used in combination with a therapeutically effective amount of a cyclic-GMP-specific phosphodiesterase inhibitor or an alpha-adrenergic receptor antagonist. The teachings and disclosure of U.S. Pat. No. 7,235,625 entitled "Multiple Agent Therapy for Sexual Dysfunction" are incorporated here by reference as if set forth in full.

The present invention thus provides methods of treating sexual dysfunction, the methods comprising the step of administering to the patient having or at risk of having sexual dysfunction a therapeutically effective amount of a cyclic peptide of the present invention in combination with a therapeutically effective amount of a second sexual dysfunction pharmaceutical agent. The cyclic peptide of the present invention may be administered simultaneously with, prior to or subsequent to administration with a therapeutically effective amount of a second sexual dysfunction pharmaceutical agent. Preferably the peptide of the present invention is administered within one hour, preferably within less than one-half hour, of administration of a therapeutically effective amount of a second sexual dysfunction pharmaceutical agent. However, for certain forms of combination therapy, such as for example in combination with a therapeutically effective amount of a hormone or hormone-related sexual dysfunction pharmaceutical agent, the hormone or hormone-related sexual dysfunction pharmaceutical agent may be administered on an independent schedule, such that there is no set or specific temporal relationship between administration of the peptide of the present invention and the hormone or hormone-related sexual dysfunction pharmaceutical agent. Thus, for example, the hormone or hormone-related sexual dysfunction pharmaceutical agent may be administered on a daily or other dose, or by means of patches or other continuous administration schedules, with administration of the peptide of the present invention when desired or needed by the patient.

The present invention thus provides methods of treating sexual dysfunction, the methods comprising the step of administering to a patient having or at risk of having sexual dysfunction a therapeutically effective amount of a cyclic peptide of the present invention in combination with another compound that is useful in the treatment of sexual dysfunction. In a preferred embodiment of combination therapy the sexual dysfunction is female sexual dysfunction. In an especially preferred embodiment of combination therapy the sexual dysfunction is erectile dysfunction.

The present invention also provides pharmaceutical compositions that comprise a cyclic peptide of the present invention and a second compound useful for the treatment of sexual dysfunction. In an embodiment of the composition, the additional compounds useful for the treatment of sexual dysfunction are preferably selected from but not limited to the group consisting of a phosphodiesterase inhibitor; a cyclic-GMP-specific phosphodiesterase inhibitor; prostaglandins; apomorphine; oxytocin modulators; α-adrenergic antagonists; androgens; selective androgen receptor modulators (SARMs); buproprion; vasoactive intestinal peptide (VIP); neutral endopeptidase inhibitors (NEP); and neuropeptide Y receptor antagonists (NPY).

In an embodiment of the method and composition, the second sexual dysfunction pharmaceutical agent is testosterone.

In another embodiment of combination therapy, the second sexual dysfunction pharmaceutical agent is a type V phosphodiesterase (PDE-5) inhibitor. For example, the PDE-5 inhibitor may be Viagra®, a brand of sildenafil, Levitra®, a brand of monohydrochloride salt of vardenafil, or Clalis®, a brand of tadalafil. Other PDE-5 inhibitors are disclosed in U.S. Pat. No. 7,235,625, issued Jun. 22, 2007, and entitled "Multiple Agent Therapy for Sexual Dysfunction", incorporated here by reference.

In another embodiment of the composition above, the compound useful for the treatment of sexual dysfunction is an estrogen agonist/antagonist. In one embodiment, the estrogen agonist/antagonist is (−)-cis-6-phenyl-5-[-4-(2-pyrrolidin-1-yl-ethoxy)-phenyl]-5,6,7,8-tetrahydro-napththalene-2-ol (also known as lasofoxifene) or an optical or geometric isomer thereof; a pharmaceutically acceptable salt, N-oxide, ester, quaternary ammonium salt; or a prodrug thereof. More preferably, the estrogen agonist/antagonist is in the form of a D-tartrate salt.

In yet another embodiment of the composition above, the estrogen agonist/antagonist is selected from the group consisting of tamoxifen, 4-hydroxy tamoxifen, raloxifene, droloxifene, toremifene, centchroman, idoxifene, 6-(4-hydroxy-phenyl)-5-[4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy-2-(4-hydroxy-phenyl)-benzo[b]thiopehn-3-yl]-methanone, EM-652, EM-800, GW 5368, GW 7604, TSE-424 and optical or geometric isomers thereof; and pharmaceutically acceptable salts, N-oxides, esters, quaternary ammonium salts, and prodrugs thereof.

In yet another embodiment, a cyclic peptide of the present invention may be used in combination with any known mechanical aids or devices.

4.0 Methods of Administration and Use

The method of administration and use varies depending upon the characteristic of specific peptides of the present invention, the disease, indication, condition or syndrome to be treated, and other factors known to those in the art. In general, any method of administration and use known in the art or hereafter developed may be employed with the peptides of the present invention. Without limiting the foregoing, the following methods of administration and use have specific application for the indicated indications.

4.1 Methods of Administration and Use for Obesity and Related Metabolic Syndrome.

Compositions including one or more peptides of the present invention may administered by any suitable means for therapy, including prophylactic therapy, of obesity and metabolic syndrome. In one aspect, the composition is formulated for subcutaneous injection, and a subcutaneous injection is given one or more times each day, preferably prior to a meal, more preferably between about one and about three hours prior to a meal. In another aspect, the composition is formulated as an injectable time release formulation, typically administered by means of a deep intramuscular injection, such as in the gluteal or deltoid muscle. In one embodiment, a peptide of the present invention is formulated with a polyethylene glycol, such as polyethylene glycol 3350, and optionally one or more additional excipients and preservatives, including but not limited to excipients such as salts, polysorbate 80, sodium hydroxide or hydrochloric acid to adjust pH, and the like. In another embodiment a peptide of the present invention is formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer (PLGA polymer) is employed, preferably a PLGA polymer with a hydrophilic end group, such as PLGA RG502H from Boehringer Ingelheim, Inc. (Ingelheim, Germany). Such formulations may be made, for example, by combining a peptide of the present invention in a suitable solvent, such as methanol, with a solution of PLGA in methylene chloride, and adding thereto a continuous phase solution of polyvinyl alcohol under suitable mixing conditions in a reactor. In general, any of a number of injectable and biodegradable polymers, which are preferably also adhesive polymers, may be employed in a time release injectable formulation. The teachings of U.S. Pat. Nos. 4,938,763, 6,432,438, and 6,673,767, and the biodegradable polymers and methods of formulation disclosed therein, are incorporated here by reference. The formulation may be such that an injection is required on a weekly, monthly or other periodic basis, depending on the concentration and amount of peptide, the biodegradation rate of the polymer, and other factors known to those of skill in the art.

Compositions including one or more peptides of the present invention may be administered orally in an individual dosage form such as a tablet or capsule. In one preferred aspect, the individual dosage form includes an enteric coating, and optionally one or more agents to increase uptake, decrease protease degradation, increase cellular permeability, and the like.

4.2 Methods of Administration and Use for Sexual Dysfunction.

For sexual dysfunction, in one aspect one or more peptides of the present invention is formulated such that it may be administered on demand, such as about less than one hour, less than two hours or less than about four hours prior to anticipated sexual activity. In one embodiment the composition is formulated for subcutaneous injection. In another embodiment, the composition is formulated for any of a variety of transdermal routes of administration, including buccal administration, nasal administration, inhalation administration and the like, including embodiments wherein the composition is formulated for nasal administration, such as by means of a metered spray device delivering a volume of from about 20 to about 200 μL of an aqueous composition including any of a variety of other agents, including permeability enhancing agents.

5.0 Methods of Making

In general, the peptides of the present invention may be synthesized by solid-phase synthesis and purified according to methods known in the art. Any of a number of well-known procedures utilizing a variety of resins and reagents may be used to prepare the peptides of the present invention.

The cyclic peptides of the present invention may be readily synthesized by known conventional procedures for the formation of a peptide linkage between amino acids. Such conventional procedures include, for example, any solution phase procedure permitting a condensation between the free alpha amino group of an amino acid residue having its carboxyl group and other reactive groups protected and the free primary carboxyl group of another amino acid residue having its amino group or other reactive groups protected. In a preferred conventional procedure, the cyclic peptides of the present invention may be synthesized by solid-phase synthesis and purified according to methods known in the art. Any of a number of well-known procedures utilizing a variety of resins and reagents may be used to prepare the peptides of the present invention.

The process for synthesizing the cyclic peptides may be carried out by a procedure whereby each amino acid residue in the desired sequence is added one at a time in succession to another amino acid residue or by a procedure whereby peptide fragments with the desired amino acid sequence are first synthesized conventionally and then condensed to provide the desired peptide. The resulting peptide is then cyclized to yield a cyclic peptide of the invention.

Solid phase peptide synthesis methods are well known and practiced in the art. In such methods the synthesis of peptides of the invention can be carried out by sequentially incorporating the desired amino acid residues one at a time into the growing peptide chain according to the general principles of solid phase methods. These methods are disclosed in numerous references, including Merrifield, R. B., Solid phase synthesis (Nobel lecture). *Angew Chem* 24:799-810 (1985) and Barany et al. *The Peptides, Analysis, Synthesis and Biology*, Vol. 2, Gross, E. and Meienhofer, J., Eds. Academic Press 1-284 (1980).

In chemical syntheses of peptides, reactive side chain groups of the various amino acid residues are protected with suitable protecting groups, which prevent a chemical reaction from occurring at that site until the protecting group is removed. Also common is the protection of the alpha amino group of an amino acid residue or fragment while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods.

Alpha amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz) and aliphatic urethane-type protecting groups, such as t-butyloxycarbonyl (Boc), diisopropylmethoxycarbonyl, isopropoxycarbonyl, and allyloxycarbonyl (Alloc). Fmoc is preferred for alpha amino protection.

Guanidino groups may be protected by a suitable protecting group, such as nitro, p-toluenesulfonyl (Tos), Z, pentamethylchromanesulfonyl (Pmc), adamantyloxycarbonyl, pentamethyldihydrobenzofuran-5-sulfonyl (Pbf) and Boc. Pbf and Pmc are preferred protecting groups for Arg.

The peptides of the invention described herein were prepared using solid phase synthesis, such as by means of a Symphony Multiplex Peptide Synthesizer (Rainin Instrument Company/Protein Technologies Inc.) automated peptide synthesizer, using programming modules as provided by the manufacturer and following the protocols set forth in the manufacturer's manual.

Solid phase synthesis is commenced from the C-terminal end of the peptide by coupling a protected alpha amino acid to a suitable resin. Such starting material is prepared by attaching an alpha amino-protected amino acid by an ester linkage to a p-benzyloxybenzyl alcohol (Wang) resin, a 2-chlorotrityl chloride resin or an oxime resin, by an amide bond between an Fmoc-Linker, such as p-[(R,S)-α-[1-(9H-fluor-en-9-yl)-methoxyformamido]-2,4-dimethyloxybenzyl]-phenoxyacetic acid (Rink linker) to a benzhydrylamine (BHA) resin, or by other means well known in the art. Fmoc-Linker-BHA resin supports are commercially available and generally used when feasible. The resins are carried through repetitive cycles as necessary to add amino acids sequentially. The alpha amino Fmoc protecting groups are removed under basic conditions. Piperidine, piperazine, diethylamine, or morpholine (20-40% v/v) in N,N-dimethylformamide (DMF) may be used for this purpose.

Following removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. After the peptide is synthesized, if desired, the orthogonally protected side chain protecting groups may be removed using methods well known in the art for further derivatization of the peptide.

Typically, orthogonal protecting groups are used as appropriate. For example, the peptides of the invention contain multiple amino acids with an amino group-containing side chain. In one aspect, an Allyl-Alloc protection scheme is employed with the amino acids forming a lactam bridge through their side chains, and orthogonal protecting groups, cleavable under different reactive conditions, used for other amino acids with amino group-containing side chains. Thus, for example, Fmoc-Orn(Alloc)-OH and Fmoc-Glu(OAll)-OH amino acids (Glu(OAll) refers to glutamic acid 5-allyl ester) can be employed for the positions forming a lactam bridge upon cyclization, while other amino acids with amino group-containing side chains have a different and orthogonal protecting group, such as with Fmoc-Arg(Pbf)-OH, Fmoc-Lys(Pbf)-OH, Fmoc-Dab(Pbf)-OH or the like. Other protecting groups may be similarly employed; by way of example and not limitation, Mtt/OPp (4-methyltrityl/2-phenylisopropyl) can be employed with the side chains forming a lactam bridge upon cyclization, with orthogonal protecting groups being utilized for other positions that are not cleavable using conditions suitable for cleavage of Mtt/OPp.

Reactive groups in a peptide can be selectively modified, either during solid phase synthesis or after removal from the resin. For example, peptides can be modified to obtain N-terminus modifications, such as acetylation, while on resin, or may be removed from the resin by use of a cleaving reagent and then modified. Similarly, methods for modifying side chains of amino acids are well known to those skilled in the art of peptide synthesis. The choice of modifications made to reactive groups present on the peptide will be determined, in part, by the characteristics that are desired in the peptide.

In the peptides of the present invention, in one embodiment the N-terminus group is modified by introduction of an N-acetyl group. In one aspect, a method is employed wherein after removal of the protecting group at the N-terminal, the resin-bound peptide is reacted with acetic anhydride in dichloromethane in the presence of an organic base, such as diisopropylethylamine. Other methods of N-terminus acetylation are known in the art, including solution phase acetylation, and may be employed.

The peptide can, in one embodiment, be cyclized prior to cleavage from the peptide resin. For cyclization through reactive side chain moieties, the desired side chains are deprotected, and the peptide suspended in a suitable solvent and a cyclic coupling agent added. Suitable solvents include, for example DMF, dichloromethane (DCM) or 1-methyl-2-pyrrolidone (NMP). Suitable cyclic coupling reagents include, for example, 2-(1H-benzotriazol-1-yl)-1,1,3,3-tetramethyluronium tetrafluoroborate (TBTU), 2-(1H-benzotriazol-1-yl)-1,1,3,3-tetramethyluronium hexafluorophosphate (HBTU), benzotriazole-1-yl-oxy-tris(dimethylamino)phosphonium-hexafluorophosphate (BOP), benzotriazole-1-yl-oxy-tris(pyrrolidino)phosphoniumhexafluorophosphate (PyBOP), 2-(7-aza-1H-benzotriazol-1-yl)-1,1,3,3-tetramethyluronium tetrafluoroborate (TATU), 2-(2-oxo-1(2H)-pyridyl)-1,1,3,3-tetramethyluronium tetrafluoroborate (TPTU) or N,N'-dicyclohexylcarbodiimide/1-hydroxybenzotriazole (DCCl/HOBt). Coupling is conventionally initiated by use of a suitable base, such as N,N-diisopropylethylamine (DIPEA), sym-collidine or N-methylmorpholine (NMM).

The cyclized peptides can then be cleaved from solid phase, using any suitable reagent, such as ethylamine in DCM or various combinations of agents, such as trifluoroacetic acid (TFA), tri-isopropylsilane (TIS), dimethoxybenezene (DMB), water and the like. The resulting crude peptide is dried and remaining amino acid side chain protecting groups, if any, are cleaved using any suitable reagent, such as TFA in the presence of water, TIS, 2-mercaptoethane (ME), and/or 1,2-ethanedithiol (EDT). The final product may be precipitated by adding cold ether and collected by filtration. Final purification is by reverse phase high performance liquid chromatography (RP-HPLC), using a suitable column, such as a $C_{18}$ column, or other methods of separation or purification, such as methods based on the size or charge of the peptide, may also be employed. Once purified, the peptide can be characterized by any number of methods, such as high performance liquid chromatography (HPLC), amino acid analysis, mass spectrometry, and the like.

For peptides of the present invention which have a C-terminus substituted amide derivative or N-alkyl group, synthesis may proceed by solid phase synthesis commenced from the C-terminal end of the peptide by coupling a protected alpha amino acid to a suitable resin. Such methods for preparing substituted amide derivatives on solid-phase have been described in the art. See, for example, Barn D. R. et al., Synthesis of an array of amides by aluminum chloride assisted cleavage on resin bound esters. *Tetrahedron Letters*, 37:3213-3216 (1996); DeGrado W. F. and Kaiser E. T., Solid-phase synthesis of protected peptides on a polymer bound oxime: Preparation of segments comprising the sequences of a cytotoxic 26-peptide analogue. *J. Org. Chem.*, 47:3258-3261 (1982). Such a starting material can be prepared by attaching an alpha amino-protected amino acid by an ester linkage to a p-benzyloxybenzyl alcohol (Wang) resin, by amide linkage to a 4-(2',4'-dimethoxylphenyl-aminomethyl-phenoxy (Rink Amide) resin, or an oxime resin, by well known means. The peptide chain is grown with the desired sequence of amino acids. Before cleavage, the peptide is cyclized on the solid phase, and the peptide-resin treated with a solution of appropriate amine (such as methyl amine, dimethyl amine, ethylamine, and so on). Peptides employing a p-benzyloxybenzyl alcohol (Wang) resin may be cleaved from resin by aluminum chloride in DCM, peptides employing a Rink Amide resin may be cleaved by mixture of TFA, TIS and water, and peptides employing an oxime resin may be cleaved by DCM.

While synthesis has been described primarily with reference to solid phase Fmoc chemistry, it is to be understood that other chemistries and synthetic methods may be employed to make the cyclic peptides of the invention, such as by way of example and not limitation, methods employing Boc chemistry, solution chemistry, and other chemistries and synthetic methods.

6.0 Formulations

Depending on the desired route of administration, the formulation of a composition including one or more cyclic peptides of the present invention may be varied. Thus the formulation may be suitable for subcutaneous injection, or intravenous injection, for nasal spray applications, for inhalation applications, for other transdermal applications and the like.

6.1 Salt Form of Cyclic Peptides of the Present Invention.

The cyclic peptides of the present invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the cyclic peptide of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the peptides of the present invention are prepared in a suitable solvent from the peptide and an excess of an acid, such as hydrochloric, hydrobromic, sulfuric, phosphoric, acetic, trifluoroacetic, citric, tartaric, maleic, succinic or methanesulfonic acid. The acetate, ammonium acetate and trifluoroacetic acid salt forms are especially useful. Where the peptides of the present invention include an acidic moiety, suitable pharmaceutically acceptable salts may include alkali metal salts, such as sodium or potassium salts, or alkaline earth metal salts, such as calcium or magnesium salts. It is also to be understood that certain peptides of formulas (I), (II), (III) and (IV) can exist in solvated forms, including solvates of the free peptide or solvates of a salt of the compound, as well as unsolvated forms. The term "solvate" is used herein to describe a molecular complex comprising the compound of the invention and one or more pharmaceutically acceptable solvent molecules, for example, ethanol. The term "hydrate" is employed when said solvent is water. It is to be understood that all polymorphs, including mixtures of different polymorphs, are included within the scope of the claimed peptides.

6.2 Pharmaceutical Compositions.

The invention provides a pharmaceutical composition that includes a cyclic peptide of the present invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The cyclic peptide compositions of the present invention may be formulated or compounded into pharmaceutical compositions that include at least one cyclic peptide of the present invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy propyl cellulose, acacia, polyethylene glycol, mannitol, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, cellulose derivatives, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or sustained-release formulations and additives may be employed, so that the dosage may be formulated so as to provide delivery of a peptide of the present invention over a period of time.

In general, the actual quantity of cyclic peptides of the present invention administered to a patient will vary between fairly wide ranges depending on the mode of administration, the formulation used, and the response desired.

In practical use, the cyclic peptides of the invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, tablets may be coated by standard aqueous or non-aqueous techniques. The amount of active peptide in such therapeutically useful compositions is such that an effective dosage will be obtained. In another advantageous dosage unit form, sublingual constructs may be employed, such as sheets, wafers, tablets or the like.

The tablets, pills, capsules, and the like may also contain binders such as povidone, gum tragacanth, acacia, corn starch or gelatin; diluents; fillers such as microcrystalline cellulose; excipients such as dicalcium phosphate; disintegrating agents such as corn starch, potato starch or alginic acid; preservatives; colorants; lubricants such as magnesium stearate; and sweetening agents such as sucrose, lactose or saccharin. When a dosage unit form is a capsule, it may contain, in addition to materials of the above type, a liquid carrier such as fatty oil. Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

If formulated for oral delivery, the peptide may be formulated and made such that it is encased in an enteric protectant, more preferably such that it is not released until the tablet or capsule has transited the stomach, and optionally has further transited a portion of the small intestine. In the context of this application it will be understood that the term enteric coating or material refers to a coating or material that will pass through the stomach essentially intact but will disintegrate after passing through the stomach to release the active drug substance. Materials that may be used includes cellulose acetate phthalate, hydroxypropylmethyl-ethylcellulose succinate, hydroxypropylmethylcellulose phthalate, polyvinyl acetate phthalate, and methacrylic acid-methyl methacrylate copolymer. The enteric coating employed promotes dissolution of the dosage form primarily at a site outside the stomach, and may be selected such that the enteric coating dissolves at a pH of approximately at least 5.5, more preferable at a pH of from about 6.0 to about 8.0.

Any of a variety of permeation enhancers may be employed, to increase uptake in the intestines upon dissolution of the enteric coating. In one aspect, permeation enhancers increase either paracellular or transcellular transport systems. Representative, non-limiting examples of such permeation enhancers include calcium chelators, bile salts (such as sodium cholate), and fatty acids. In some embodiments, peptides or polypeptides that act as substrates for intestinal proteases are further added.

Cyclic peptides may also be administered parenterally. Solutions or suspensions of these active peptides can be prepared in water suitably mixed with a surfactant such as hydroxy-propylcellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

The cyclic peptides of the present invention may be therapeutically applied by means of nasal administration. By "nasal administration" is meant any form of intranasal administration of any of the cyclic peptides of the present invention. The peptides may be in an aqueous solution, such as a solution including saline, citrate or other common excipients or preservatives. The peptides may also be in a dry or powder formulation.

The cyclic peptides of the present invention may be formulated with any of a variety of agents that increase effective nasal absorption of drugs, including peptide drugs. These agents may increase nasal absorption without unacceptable damage to the mucosal membrane. U.S. Pat. Nos. 5,693,608, 5,977,070 and 5,908,825, among others, teach a number of pharmaceutical compositions that may be employed, including absorption enhancers, and the teachings of each of the foregoing, and all references and patents cited therein, are incorporated by reference.

If in an aqueous solution, the cyclic peptides may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, and the like, a 50 mM solution may be employed. In addition to buffering agents, a suitable preservative may be employed, to prevent or limit bacteria and other microbial growth. One such preservative that may be employed is 0.05% benzalkonium chloride.

In an alternative embodiment, cyclic peptides of the present invention may be administered directly into the lung. Intrapulmonary administration may be performed by means of a metered dose inhaler, a device allowing self-administration of a metered bolus of a peptide of the present invention when actuated by a patient during inspiration. In one aspect of this embodiment, the cyclic peptide may be in a dried and particulate form, for example particles between about 0.5 and 6.0 µm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With micro-particles, the peptides may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multi-dose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 µm.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

The cyclic peptides of the present invention may be therapeutically administered by means of an injection of a sustained release formulation. In one embodiment, a cyclic peptide of the present invention is formulated for a deep intramuscular injection, such as in the gluteal or deltoid muscle, of a formulation with a polyethylene glycol, such as polyethylene glycol 3350, and optionally one or more additional excipients and preservatives, including but not limited to excipients such as salts, polysorbate 80, sodium hydroxide or hydrochloric acid to adjust pH, and the like. In another embodiment a cyclic peptide of the present invention is formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer is employed. In general, any of a number of injectable and bioerodible polymers, which are preferably also adhesive polymers, may be employed in a sustained release injectable formulation. Alternatively other sustained release formulations may be employed, including formulations permitting subcutaneous injection, which other formulations may include one or more of nano/microspheres (such as compositions including PLGA polymers), liposomes, emulsions (such as water-in-oil emulstions), gels, insoluble salts or suspensions in oil. The formulation may be such that an injection is required on a daily, weekly, monthly or other periodic basis, depending on the concentration and amount of cyclic peptide, the sustained release rate of the materials employed, and other factors known to those of skill in the art.

6.3 Routes of Administration.

If a composition including one or more peptides of the present invention is administered by injection, the injection may be intravenous, subcutaneous, intramuscular, intraperitoneal or other means known in the art. The peptides of the present invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the peptides of invention are introduced across an epidermal layer of cells may be employed. Administration means may thus include administration through mucous membranes, buccal administration, oral administration, dermal administration, inhalation administration, nasal administration, urethral administration, vaginal administration, and the like.

6.4 Therapeutically Effective Amount.

In general, the actual quantity of cyclic peptide of the present invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. The cyclic peptides of the present invention are highly active. For example, the cyclic peptide can be administered at about 0.1, 0.5, 1, 5, 50, 100, 500, 1000 or 5000 μg/kg body weight, depending on the specific peptide selected, the desired therapeutic response, the route of administration, the formulation and other factors known to those of skill in the art.

7.0 Tests and Assays Employed in Evaluation of the Peptides of the Present Invention The melanocortin receptor-specific peptides of the present invention of this invention may be tested by a variety of assay systems and animal models to determine binding, functional status and efficacy.

7.1 Competitive Inhibition Assay using [$I^{125}$]-NDP-α-MSH.

A competitive inhibition binding assay was performed using membrane homogenates prepared from HEK-293 cells that express recombinant hMC4-R, hMC3-R, or hMC5-R, and from B-16 mouse melanoma cells (containing endogenous MC1-R). In some instances, HEK-293 cells that express recombinant hMC1-R were employed. In the examples that follow, all MC3-R, MC4-R and MC5-R values are for human recombinant receptors. MC1-R values are for B-16 mouse melanoma cells, unless the heading is "hMC1-R", in which case the value is for human recombinant MC1-R. Assays were performed in 96 well GF/B Millipore multi-screen filtration plates (MAFB NOB10) pre-coated with 0.5% bovine serum albumin (Fraction V). Membrane homogenates were incubated with 0.2 nM (for hMC4-R) 0.4 nM (for MC3-R and MC5-R) or 0.1 nM (for mouse B16 MC1-R or hMC1-R) [$I^{125}$]-NDP-α-MSH (Perkin Elmer) and increasing concentrations of test peptides of the present invention in buffer containing 25 mM HEPES buffer (pH 7.5) with 100 mM NaCl, 2 mM $CaCl_2$, 2 mM $MgCl_2$, 0.3 mM 1,10-phenanthroline, and 0.2% bovine serum albumin. After incubation for 60 minutes at 37° C., the assay mixture was filtered and the membranes washed three times with ice-cold buffer. Filters were dried and counted in a gamma counter for bound radioactivity. Non-specific binding was measured by inhibition of binding of [$I^{125}$]-NDP-α-MSH in the presence of 1 μM NDP-α-MSH. Maximal specific binding (100%) was defined as the difference in radioactivity (cpm) bound to cell membranes in the absence and presence of 1 μM NDP-α-MSH. Radioactivity (cpm) obtained in the presence of test peptides was normalized with respect to 100% specific binding to determine the percent inhibition of [$I^{125}$]-NDP-α-MSH binding. Ki values for test peptides of the present invention were determined using Graph-Pad Prism® curve-fitting software.

7.2 Competitive Binding Assay Using Eu-NDP-α-MSH

Alternatively, a competitive inhibition binding assay was performed employing Eu-NDP-α-MSH (PerkinElmer Life Sciences catalog No. AD0225) with determination by time-resolved fluorometry (TRF) of the lanthanide chelate. In comparison studies with [$I^{125}$]-NDP-α-MSH, the same values, within experimental error ranges, were obtained for percent inhibition and Ki. Typically competition experiments to determine Ki values were conducted by incubating membrane homogenates prepared from HEK-293 cells that express recombinant hMC4-R with 9 different concentrations of test peptides of interest and 1 nM of Eu-NDP-α-MSH in a solution containing 25 mM HEPES buffer with 100 mM NaCl, 2 mM $CaCl_2$, 2 mM $MgCl_2$, 0.1% BSA and 0.3 mM 1,10-phenanthroline. After incubation for 90 minutes at 37° C., the reaction was stopped by filtration over AcroWell 96-well filter plates (Pall Life Sciences). The filter plates were washed 4 times with 200 μL of ice-cold phosphate-buffered saline. DELFIA Enhancement solution (PerkinElmer Life Sciences) was added to each well. The plates were incubated on a shaker for 15 minutes and read at 340 nm excitation and 615 nm emission wavelengths. Each assay was conducted in duplicate and mean values were utilized. Ki values were determined by curve-fitting with Graph-Pad Prism® software using a one-site fixed-slope competition binding model.

7.3 Assay for Agonist Activity.

Accumulation of intracellular cAMP was examined as a measure of the ability of the peptides of the present invention to elicit a functional response in HEK-293 cells that express MC4-R. Confluent HEK-293 cells that express recombinant hMC4-R were detached from culture plates by incubation in enzyme-free cell dissociation buffer. Dispersed cells were suspended in Earle's Balanced Salt Solution containing 10 mM HEPES (pH 7.5), 1 mM $MgCl_2$, 1 mM glutamine, 0.5% albumin and 0.3 mM 3-isobutyl-1-methyl-xanthine (IBMX), a phosphodiesterase inhibitor. The cells were plated in 96-well plates at a density of $0.5 \times 10^5$ cells per well and pre-incubated for 10 minutes. Cells were exposed for 15 minutes at 37° C. to peptides of the present invention dissolved in DMSO (final DMSO concentration of 1%) at a concentration range of 0.05-5000 nM in a total assay volume of 200 μL. NDP-α-MSH was used as the reference agonist. cAMP levels were determined by an HTRF® cAMP cell-based assay system from Cisbio Bioassays utilizing cryptate-labeled anti-cAMP and d2-labeled cAMP, with plates read on a Perkin-Elmer Victor plate reader at 665 and 620 nM. Data analysis was performed by nonlinear regression analysis with Graph-Pad Prism® software. The maximum efficacies of the test peptides of the present invention were compared to that achieved by the reference melanocortin agonist NDP-α-MSH.

7.4 High and Low Density hMC4-R Functional Assay.

A HEK293 cell line transfected with human MC4-R (from Palatin Technologies, US, with license from the University of Michigan) was used. The human MC4-R was introduced to HEK293 by using the T-REx™ System, Invitrogen. The T-REx™ System employs a tetracycline-regulated mammalian expression system that uses regulatory elements from the *E. coli* Tn10-encoded tetracycline (Tet) resistance operon. By use of the T-REx™ System, expression of the gene of interest, the human MC4-R gene, is repressed in the absence of tetracycline or doxycycline and induced in the presence of tetracycline or doxycycline (see T-REx™ System Manual, published by Invitrogen).

HEK293-T-REx-MC4-R cells were cultured in DMEM (Gibco 11965), supplemented with L-Glutamine (Gibco 25030), 10% fetal bovine serum (FBS), 200 μg/mL Zeocin (Invitrogen 46-0072) and 6 mg/mL Blasticidin (Invitrogen 46-1120) in 5% $CO_2$ and 95% humidity at 37° C. T-150 flasks of cells at 75% confluence were incubated with two concentrations of doxycycline (0.1 ng/mL to provide a low density hMC4-R system and 10 ng/mL to provide a high density hMC4-R system) in 5% $CO_2$ at 37° C. for 16-18 hours to induce MC4-R expression. On the day of the assay, the cells were washed with PBS (Gibco 14190) and harvested using cell dissociation buffer (Gibco 13150-016), then centrifuged and resuspended in Hanks' Balanced Salt Solution (+Ca, +Mg) (Gibco 14025), 10 mM 4-(2-hydroxyethyl)-1-piperazineethanesulfonic acid (HEPES) (pH 7.4) (Sigma H0887), 1 mM L-Glutamine (Gibco 25030), 1 mg/mL bovine serum albumin (BSA) (Sigma A3311) and 0.3 mM 3-isobutyl-1-methyl-xanthine (IBMX). Cells were then counted and volume was adjusted to $5\times10^4$ cells per 200 µL.

The cells were then dispensed into 96-well plates (BD 353916) in 198 µL (about $5\times10^4$) cells/well and incubated for 10 minutes at 37° C. The compound to be tested was diluted with DMSO to a final concentration of 1 mM. Serial dilution was prepared in polypropylene removable 12-well library tube strips (VWR cat #83009-682). 120 µL of the 1 mM compound stock was pipetted in the second column on the plate. Using the Janus liquid handler the compound was serially diluted 1:10 (25 µL compound+225 µL DMSO) to a total of 10 concentrations (ranging from $10^{-5}$ to $10^{-13}$ M).

2 µL of the standard, [Nle$^4$, D-Phe$^7$]alpha-Melanocyte Stimulating Hormone (NDP-α-MSH), or compound was added to the 96-well plate using the Janus robotic system. All assay samples were run in duplicate (i.e. each sample was in two low dox and two high dox plates, respectively). The plates were gently shaken and incubated for 15 minutes at 37° C. The reaction was stopped by adding 15 µL of lysis buffer per well and the plates were shakened for 30 minutes at room temperature.

Agonist stimulation of the MC4-R activates adenylate cyclase, which is an enzyme that catalyses the formation 3',5'-cyclic adenosine monophosphate (cAMP) from adenosine triphosphate (ATP). Thus, agonist stimulation of the MC4-R increases the levels of cAMP. cAMP-levels were measured with the cAMP dynamic 2 HTRF kit (CisBio cat #62AM4PEC; see manual published by CisBio). cAMP levels were normalised against plate controls (2% DMSO for 0%, 400 nM NDP-α-MSH for 100%) and a calibration curve ranging from 712 nM to 0.04 nM cAMP (as described in the CisBio HTRF kit). The plates were incubated on a shaker at room temperature for 1 hour and read on the Perkin-Elmer Victor plate reader at 665 and 620 nm. Fluoresence ratios were then calculated as described in the CisBio HTRF kit, with GraphPad Prism software used to plot the change in fluorescence percent values versus cAMP concentration using the variable slope dose response curve and, based on calculated cAMP concentrations, to determine $EC_{50}$ and $E_{max}$ values.

7.5 Food Intake and Body Weight Change.

Change in food intake and body weight is evaluated for selected peptides administered by intravenous (IV) or subcutaneous injection routes. Male Sprague-Dawley rats are obtained from Hilltop Lab Animals, Inc. (Scottsdale, Pa.) or other vendors. Animals are individually housed in conventional polystyrene hanging cages and maintained on a controlled 12 hour on/off light cycle. Water and pelleted food was provided ad libitum. The rats are dosed IV with vehicle or selected peptides (0.3 to 1.0 mg/kg), or dosed subcutaneously with vehicle or selected peptides (doses up to 30 mg/kg). The changes in body weight and food intake for the 24 hour period after dosing is determined. The changes in body weight and food intake for the 48 hour and 72 hour periods after dosing can also be measured to determine reversal of changes in body weight and food intake effects back to baseline levels.

7.6 Induction of Penile Erection.

The ability of peptides of the present invention to induce penile erection (PE) in male rats are evaluated. Male Sprague-Dawley rats weighing 250-300 g are kept on a 12 hour on/off light cycle with food and water ad libitum. All behavioral studies are performed between 9 a.m. and 4 p.m. Groups of 6-8 rats are administered peptides at a variety of doses via an IV or subcutaneous injection route. Immediately after treatment, rats are placed into individual polystyrene cages (27 cm long, 16 cm wide, and 25 cm high) for behavioral observation, typically by remote video monitoring. Rats are observed for one hour, and the number of yawns, grooming bouts and PEs are recorded in 10-minute bins.

8.0 Peptides of the Present Invention

In one aspect, the invention provides a cyclic peptide which contains a core sequence derived from or a modification of the sequence His-Phe-Arg-Trp within the cyclic portion, which peptide is cyclized through a Glu adjacent the His (or derivative, modification of or substitute for His) and an Orn adjacent the Trp (or derivative, modification of or substitute for Trp), or alternatively an Orn adjacent the His (or derivative, modification of or substitute for His) and a Glu adjacent the Trp (or derivative, modification of or substitute for Trp). The cyclic peptide is at least a cyclic hexapeptide, containing six amino acids including both Glu and Orn within the cyclic portion, and optionally is a cyclic heptapeptide or larger cyclic peptide, with one or more additional amino acid residues outside the cyclic portion on either or both the N-terminus or C-terminus ends.

The core sequence derived from His-Phe-Arg-Trp typically will include unsubstituted or substituted Phe in the Phe position, such as substituted or subsubstituted D-Phe, but a variety of amino acids may be utilitized for the remaining amino acids in the core sequence. In general, the His position may be a substituted or unsubstituted Pro, or may be an amino acid with a side chain including at least one primary amine, secondary amine, alkyl, cycloalkyl, cycloheteroalkyl, aryl, heteroaryl, alcohol, ether, sulfide, sulfone, sufoxide, carbamoyl or carboxyl. The Arg position may be a substituted or unsubstituted Pro, or may be an amino acid with a side chain including at least one primary amine, secondary amine, guanidine, urea, alkyl, cycloalkyl, cycloheteroalkyl, aryl, heteroaryl, or ether. The Trp position may be an amino acid with a side chain including at least one substituted or unsubstituted aryl or heteroaryl.

In another aspect, it has been found that a lactam bridge wherein the amide bond is positioned by means of the side chain of Glu or Orn (at the N-terminus of the cyclic portion) and the side chain of Orn or Glu (at the C-terminus end of the cyclic portion) has superior efficacy, such as efficacy determined by $EC_{50}$ or $E_{max}$ values, compared to peptides wherein the lactam bridge amide bond is positioned by means of the side chains of Asp and Lys, but which are otherwise identical. Such peptides do not necessarily show increased binding affinity, such as measured by Ki values, compared to peptides wherein the lactam bridge amide bond is positioned by means of the side chains of Asp and Lys, but which are otherwise identical. However, for many diagnostic and medical applications the functional efficacy, such as efficacy determined by $EC_{50}$ or $E_{max}$ values, is critical for desired biological and/or pharmacological activities. This discovery is contrary to assertions in the prior art that the location and direction of an amide bond in the lactam bridge of melanocortin receptor-specific peptides is of little importance for activity, and does not interact with receptors. See, for example, Bednarek M A et al., Potent and selective peptide agonists of α-melanotropin action at human melanocortin receptor 4: their systhesis and biological evaluation in vitro. *Biochem. Biophys. Res. Comm.* 286:641-645 (2001).

Cyclic peptides of the invention accordingly include those wherein the side chains of the amino acids forming a cyclic lactam bridge have the structure —(CH$_2$)$_2$—C(=O)—NH—

$(CH_2)_3$— or —$(CH_2)_3$—NH—C(=O)—$(CH_2)_2$. Such compounds may, but need not, include peptides where an amino acid in the first position outside the cyclic portion has a side chain including at least one primary amine, guanidine or urea group. Alternatively, the amino acid in the first position outside the cyclic portion may be any amino acid, including without limitation amino acids with a side chain including a $C_1$ to $C_4$ linear or branched alkyl. It may readily be seen by reference to the peptides actually made as set forth in section 8.1 hereof that diverse and multiple substitutions may be made to the peptides, and still be within the scope and intent of this aspect of the invention.

The lactam bridge wherein the amide bond is positioned by means of the side chain of Glu or Orn (at the N-terminus of the cyclic portion) and the side chain of Orn or Glu (at the C-terminus end of the cyclic portion) was designed on the basis of an in-house MC4-R agonist pharmacophore model with three key interactions in the MC4-R receptor-ligand binding site: a hydrophobic binding region surrounded by the $Trp^{258}$ on helix 6 and adjacent residues to which the phenyl ring of D-Phe ring or an equivalent ring binds, a positive-charged group binding region to directly interact with negative-charged $Asp^{126}$ on helix 3 of the receptor, and a polar group binding region to form a hydrogen bond interaction with $His^{264}$ on helix 6. This three-point pharmacophore model, illustrated in FIG. 1, suggests that $Asp^{126}$ on helix 3 acts as an anchor for an agonist to bind strongly with MC4-R while the other two interaction sites on helix 6 can be used as leverage points to adjust the pose of helix 6, which is believed to be critical for triggering MC4-R agonism. Compared with other reported MC4-R pharmacophore models, the model of FIG. 1 emphasizes the hypothesized role of $His^{264}$ in controlling the molecular mechanism of MC4-R agonism.

Figure 2:
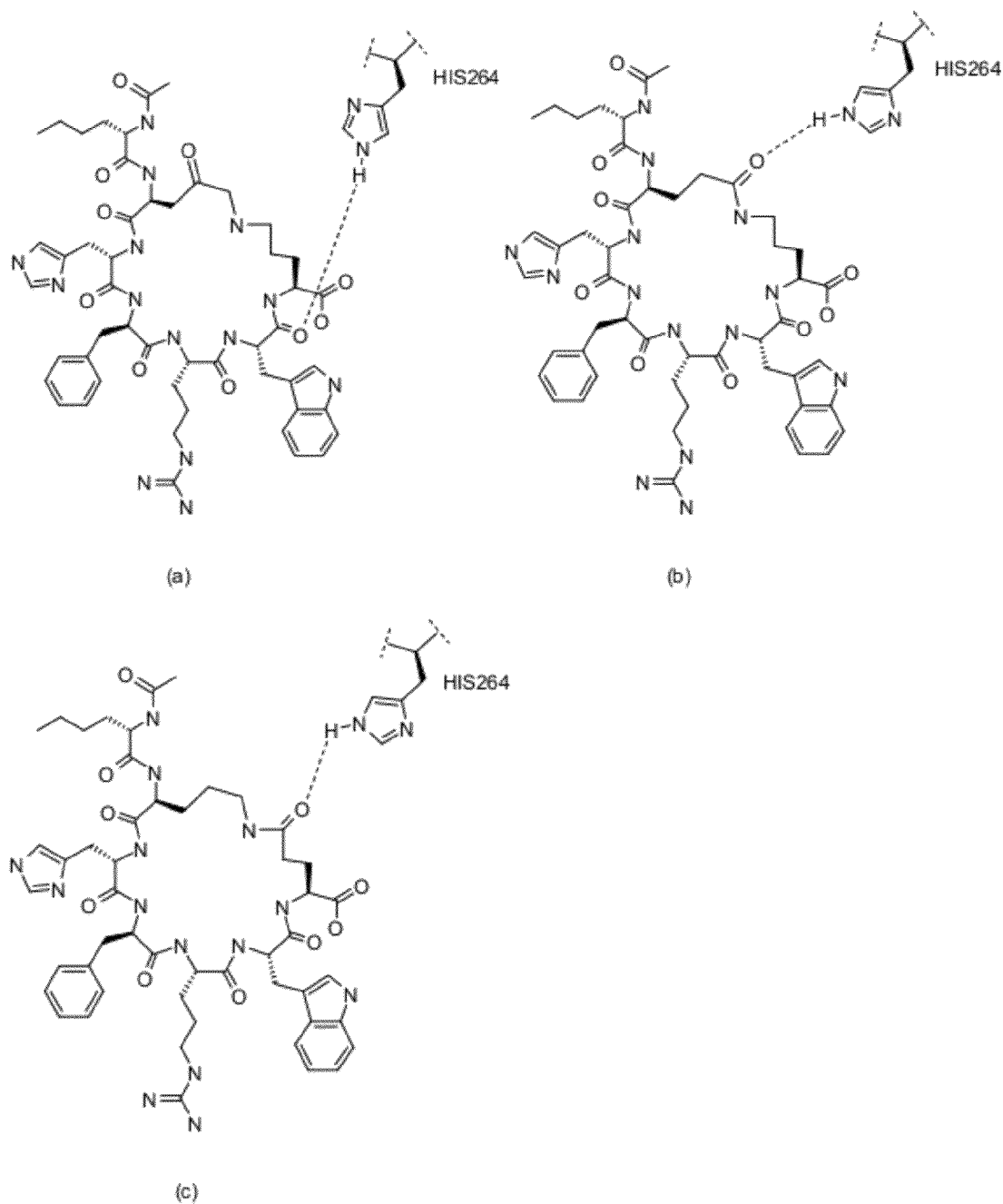
FIG. 2 is a model illustration of proposed binding modes of the prior art peptide Ac-Nle-cyclo(Asp-His-D-Phe-Arg-Trp-Lys)-OH (shown in (a)), peptide No. 1 of the invention of the sequence Ac-Nle-cyclo(Glu-His-D-Phe-Arg-Trp-Orn)-OH (shown in (b)) and peptide No. 34 of the invention of the sequence Ac-Nle-cyclo(Orn-His-D-Phe-Arg-Trp-Glu)-OH (shown in (c)) in the MC4-R binding site as suggested by molecular modeling studies. Hypothesized intermolecular hydrogen bonds between $His^{264}$ of the receptor and each peptide are indicated by dashed lines.

The assumption behind this pharmacophore model is that helix 6 plays a critical role in MC4-R agonism and further that it is possible to effectively influence the degree of MC4-R agonism response by adjusting the pose of helix 6. $His^{264}$ was previously identified in mutagenesis studies (Pogozheva I. D. et al., Interactions of human melanocortin 4 receptor with nonpeptide and peptide agonists. *Biochemistry* 44:11329-11341 (2005)), and is located near the extracellular end of helix 6 and faces to the inside of the ligand binding pocket in our MC4-R homology models. The MC4-R docking model of certain cyclic peptides of this invention shows that the side chain lactam linkage group is presumptively located close to $His^{264}$, and that by adjusting the lactam group position a direct hydrogen bond interaction with $His^{264}$ is possible. This is graphically illustrated by FIG. 2, which illustrates proposed binding modes of the prior art peptide Ac-Nle-cyclo(Asp-His-D-Phe-Arg-Trp-Lys)-OH (shown in (a)), peptide No. 1 of the invention of the sequence Ac-Nle-cyclo(Glu-His-D-Phe-Arg-Trp-Orn)-OH (shown in (b)) and peptide No. 34 of the invention of the sequence Ac-Nle-cyclo(Orn-His-D-Phe-Arg-Trp-Glu)-OH (shown in (c)), all in the MC4-R binding site as suggested by molecular modeling studies. Proposed intermolecular hydrogen bonds between $His^{264}$ of the receptor and the prior art peptide and each of peptides No. 1 and 34 are indicated by dashed lines. The prior art peptide, shown in (a) in FIG. 2, is disclosed in U.S. Pat. Nos. 6,579,968 and 6,794,489. Peptide No. 1, a peptide of this invention shown in (b) in FIG. 2, is an analog peptide with a lactam shift by one atom, such that Asp is replaced with Glu and Lys is replaced with Orn. Peptide No. 34, a peptide of this invention shown in (c) in FIG. 2, is an analog peptide with a lactam shift by three atoms, such that Asp is replaced with Orn and Lys is replaced with Glu. It is hypothesized, based in part upon computational docking models, and without wishing to be bound by theory, that $His^{264}$ forms a lateral hydrogen bond interaction with the backbone carbonyl group of $Trp^9$ on the prior art peptide cyclized through Asp . . . Lys, with obvious consequences with respect to the position of helix 3. A constrained conformational analysis inside the binding pocket revealed that a simple position shift of the side-chain linkage lactam group by one atom may be enough to re-position this polar group to form a hydrogen bond interaction with $His^{264}$ from the front, as shown in FIG. 2 (b) with peptide No. 2. Further analysis also indicated that a position shift of this lactam group by three atoms may point this polar group to the same direction to form a hydrogen bond interaction with $His^{264}$ as well, as shown in FIG. 2 (c) with peptide No. 34. It is further hypothesized, again without being bound by theory, that these changes of the direction of a highly critical hydrogen bond for MC4-R agonism, resulting from the lactam shifts by employing a cyclic lactam bridge having either the structure —$(CH_2)_2$—C(=O)—NH—$(CH_2)_3$— or —$(CH_2)_3$—NH—C(=O)—$(CH_2)_2$, have a profound influence on its agonist activity.

The peptides encompassed within formulas (I) and (III) contain one or more asymmetric elements such as stereogenic centers, stereogenic axes and the like, so that the peptides encompassed within formulas (I) and (III) can exist in different stereoisomeric forms. For both specific and generically described peptides, including the peptides encompassed within formulas (I) and (III), all forms of isomers at all chiral or other isomeric centers, including enantiomers and diastereomers, are intended to be covered herein. The peptides of the invention each include multiple chiral centers, and may be used as a racemic mixture or an enantiomerically enriched mixture, in addition to use of the peptides of the invention in enantiopure preparations. Typically, the peptides of the invention will be synthesized with the use of chirally pure reagents, such as specified L- or D-amino acids, using reagents, conditions and methods such that enantiomeric purity is maintained, but it is possible and contemplated that racemic mixtures may be made. Such racemic mixtures may optionally be separated using well-known techniques and an individual enantiomer may be used alone. In cases and under specific conditions of temperature, solvents and pH wherein peptides may exist in tautomeric forms, each tautomeric form is contemplated as being included within this invention whether existing in equilibrium or predominantly in one form. Thus a single enantiomer of a peptide of formulas (I) and (III), which is an optically active form, can be obtained by asymmetric synthesis, synthesis from optically pure precursors, or by resolution of the racemates.

The peptides of formula (II) is a specific stereoisomeric form of the peptides of formula (I), but the invention should not be construed as being limited to the stereoisomeric forms encompassed by formula (II).

The invention is further intended to include prodrugs of the present peptides, which on administration undergo chemical conversion by metabolic processes before becoming active pharmacological peptides. In general, such prodrugs will be functional derivatives of the present peptides, which are readily convertible in vivo into a peptide of formulas (I) and (III). Prodrugs are any covalently bonded compounds, which release the active parent peptide drug of formulas (I) and (III) in vivo. Conventional procedures for the selection and preparation of suitable prodrug derivatives are described, for example, in "Design of Prodrugs", ed. H. Bundgaard, Elsevier, 1985. Typical examples of prodrugs have biologically labile protecting groups on a functional moiety, such as for example by esterification of hydroxyl, carboxyl or amino functions. Thus by way of example and not limitation, a prodrug includes peptides of formula (I) wherein an ester prodrug form is employed, such as, for example, lower alkyl esters of an R group of formula (I), such as where R is —OH, which lower alkyl esters may include from 1-8 carbons in an alkyl radical or aralkyl esters which have 6-12 carbons in an aralkyl radical. Broadly speaking, prodrugs include compounds that can be oxidized, reduced, aminated, deaminated, hydroxylated, dehydroxylated, hydrolyzed, dehydrolyzed, alkylated, dealkylated, acylated, deacylated, phosphorylated or dephosphorylated to produce an active parent peptide drug of formula (I) in vivo.

The subject invention also includes peptides which are identical to those recited in formula (I), but for the fact that one or more atoms depicted in formula (I) are replaced by an atom having an atomic mass or mass number different from the atomic mass or mass number usually found in nature. Examples of isotopes that can be incorporated into peptides of the invention include isotopes of hydrogen, carbon, nitrogen and oxygen, such as $^2H$, $^3H$, $^{13}C$, $^{14}C$, $^{15}N$, $^{18}O$ and $^{17}O$, respectively. Peptides of the present invention and pharmaceutically acceptable salts or solvates of said peptides which contain the aforementioned isotopes and/or other isotopes of other atoms are within the scope of this invention. Certain isotopically-labeled peptides of the present invention, for example those into which radioactive isotopes such as $^3H$ and $^{14}C$ are incorporated, may have use in a variety of assays, such as in drug and/or substrate tissue distribution assays. Substitution with heavier isotopes, such as substitution of one or more hydrogen atoms with deuterium ($^2H$), can provide pharmacological advantages in some instances, including increased metabolic stability. Isotopically labeled peptides of formula (I) can generally be prepared by substituting an isotopically labeled reagent for a non-isotopically labeled reagent.

8.1 Specific Peptides.

Peptides of the following structures were synthesized by the general methods described above. In brief, the peptides were prepared by solid-phase synthesis method with Fmoc chemistry. Peptide amides were synthesized using Rink amide resin (EMD Biosciences, Inc. San Diego, Calif.). Peptide acids were prepared using Fmoc-Lys(Mtt)-p-alkoxy benzyl alcohol resin (0.55 mmol/g, Bachem California Inc, Torrance, Calif.) or 4-Methoxybenzhydryl bromide resin (1.7 mmol/g, CBL Patras, Greece). The protecting groups for side chains were Arg(Pbf), Asp(OAll), Glu(OAll), His(Trt), Lys (Aloc), Orn(Aloc), Boc-4-amino-Pyrrolidine-2-carboxylic acid and Trp(Boc). Single coupling of each residue was performed using TBTU and diisopropylethylamine (DIEA) as coupling reagents, with a 3-fold excess of amino acid and 30-45 minute coupling times. Acetylation of the α-amino group of the N-terminal residue was normally carried out with 10 eq. acetic anhydride and 20 eq. pyridine in DMF for 30 minutes. The side chain lactam bridge was formed on resin after completion of peptidyl chain elongation, using 2 eq. TBTU and 4 eq. DIEA. Peptide was cleaved from resin by a mixture of trifluoroacetic acid (TFA), triisopropylsilane (TIS) and water (v/v/v=92.5/2.5/5.0) for 2-3 hours at room temperature. Crude preparation was precipitated from anhydrous ethyl ether. After centrifugation, and washing twice with ethyl ether, the resulting solid was dissolved in 50% acetic acid in water and stored overnight at room temperature to decarboxylate the N-carboxy group from the indole group of tryptophan residue. After removal of solvents by drying, the crude was purified by HPLC using a reverse phase preparative C-18 column. Pure fractions were pooled and lyophilized.

Peptides of the present invention, which are peptides cyclized through Glu . . . Orn side chains such that the lactam bridge has the structure —$(CH_2)_2$—C(=O)—NH—$(CH_2)_3$— from backbone carbon to backbone carbon, are set forth below in Table 1. Peptides of the present invention, which are peptides cyclized through Orn . . . Glu side chains such that the lactam bridge has the structure —$(CH_2)_3$—NH—C(=O)—$(CH_2)_2$ from backbone carbon to backbone carbon, are set forth below in Table 2.

TABLE 1

| No. | Structure | Primary Sequence |
| --- | --- | --- |
| 1 | 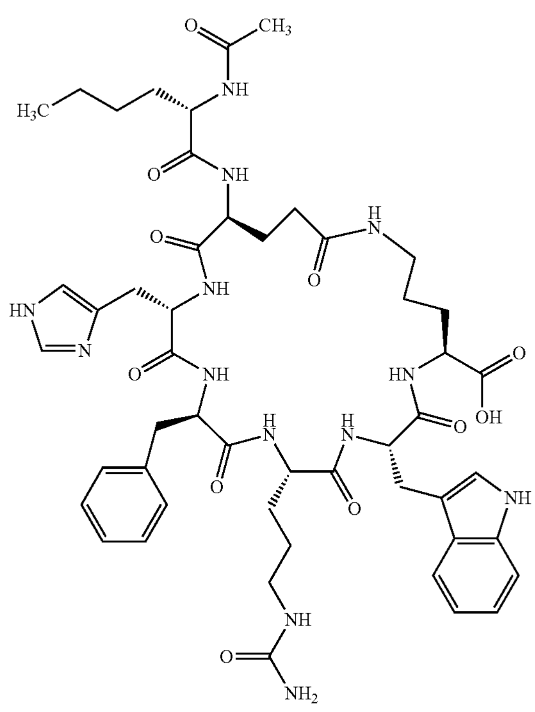 [SMILES: CCCC[C@H](NC(C)=O)C(=O)N[C@H]1CCC(=O)NCCC[C@@H](C(=O)O)NC(=O)[C@H](Cc2c[nH]c3ccccc23)NC(=O)[C@H](CCCNC(N)=O)NC(=O)[C@@H](Cc2ccccc2)NC(=O)[C@H](Cc2c[nH]cn2)NC1=O] | Ac-Nle-cyclo(Glu-His-D-Phe-Arg-Trp-Orn)-OH |

TABLE 1-continued
| No. | Structure | Primary Sequence |
|---|---|---|
| 2 | 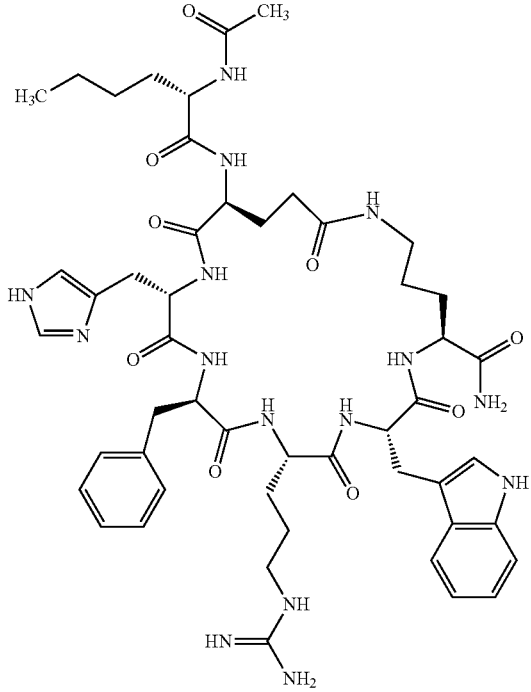 [SMILES: CCCC[C@H](NC(C)=O)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-Nle-cyclo(Glu-His-D-Phe-Arg-Trp-Orn)-NH₂ |
| 3 | 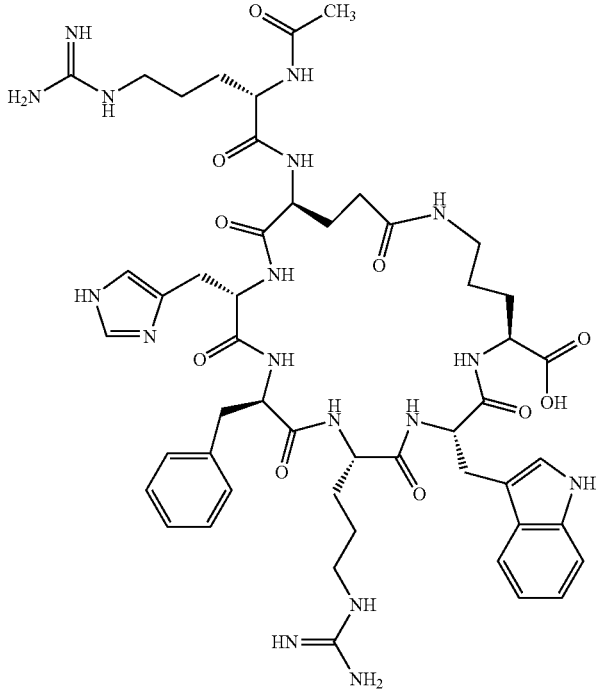 | Ac-Arg-cyclo(Glu-His-D-Phe-Arg-Trp-Orn)-OH |

TABLE 1-continued

| No. | Structure | Primary Sequence |
|---|---|---|
| 4 | 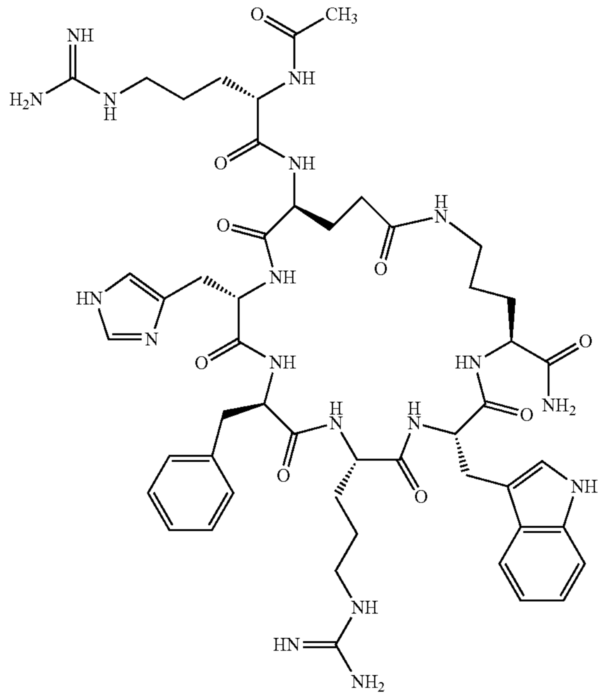 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-Arg-cyclo(Glu-His-D-Phe-Arg-Trp-Orn)-NH$_2$ |
| 5 | 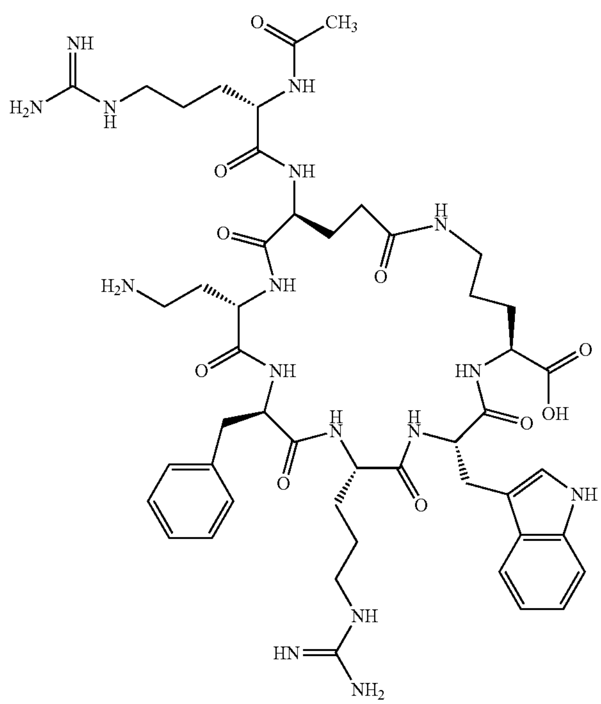 [SMILES: CC(=O)N[C@@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Ac-Arg-cyclo(Glu-Dab-D-Phe-Arg-Trp-Orn)-OH |

TABLE 1-continued

| No. | Structure | Primary Sequence |
|---|---|---|
| 6 | 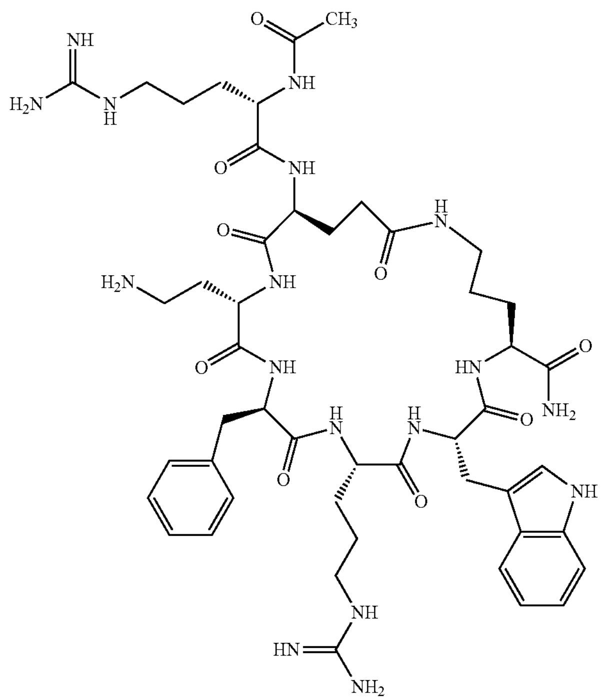 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Ac-Arg-cyclo(Glu-Dab-D-Phe-Arg-Trp-Orn)-NH₂ |
| 7 | 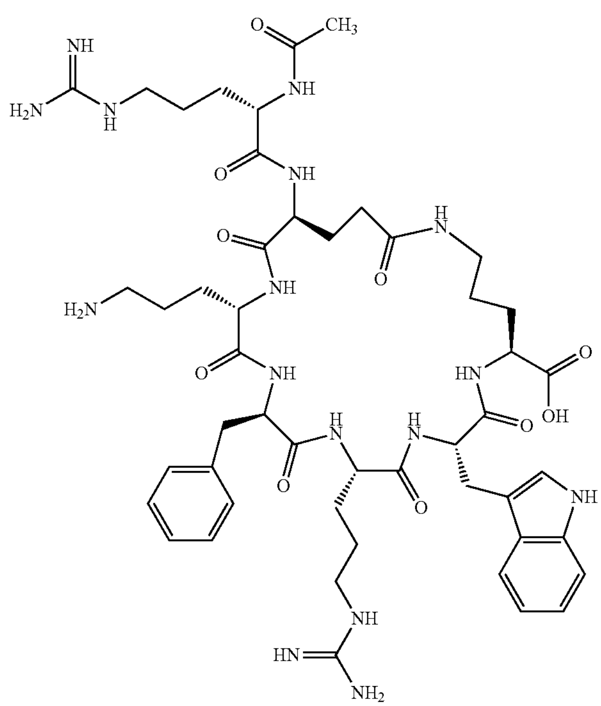 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCCN)NC1=O] | Ac-Arg-cyclo(Glu-Orn-D-Phe-Arg-Trp-Orn)-OH |

TABLE 1-continued

| No. | Structure | Primary Sequence |
|---|---|---|
| 8 | 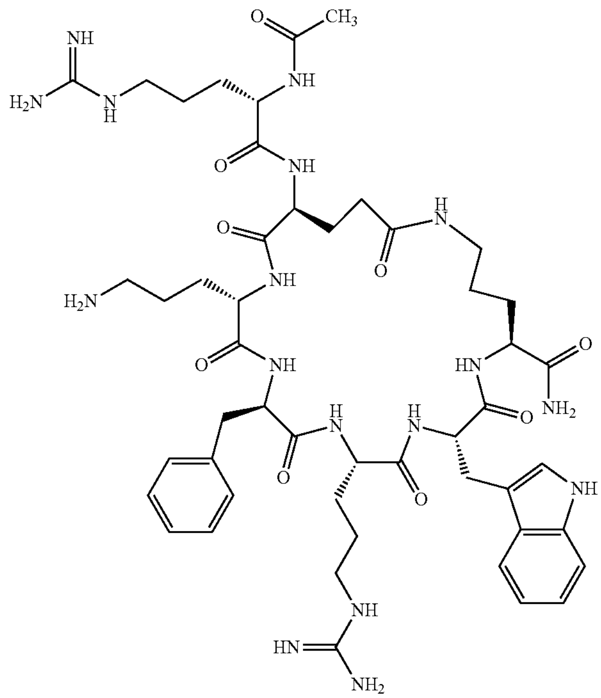 | Ac-Arg-cyclo(Glu-Orn-D-Phe-Arg-Trp-Orn)-NH$_2$ |
| 9 | 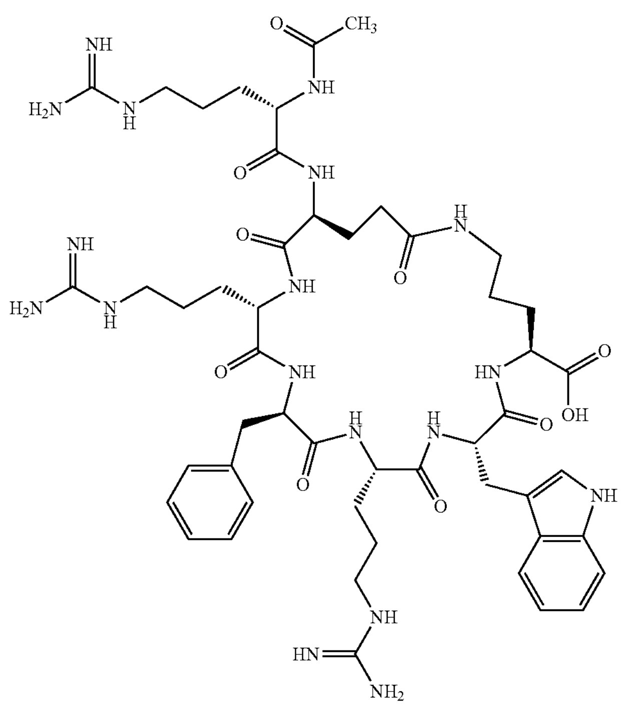 | Ac-Arg-cyclo(Glu-Arg-D-Phe-Arg-Trp-Orn)-OH |

| No. | Structure | Primary Sequence |
|---|---|---|
| 10 | 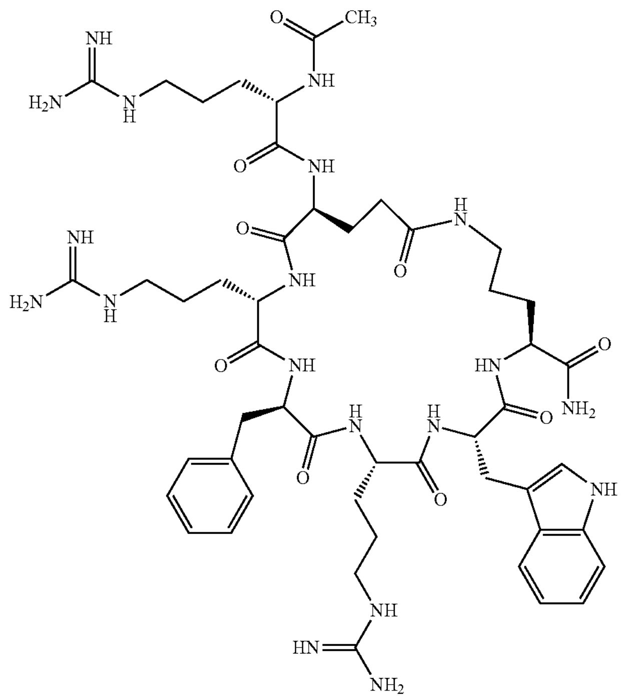 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCCNC(=N)N)NC1=O] | Ac-Arg-cyclo(Glu-Arg-D-Phe-Arg-Trp-Orn)-NH$_2$ |
| 11 | 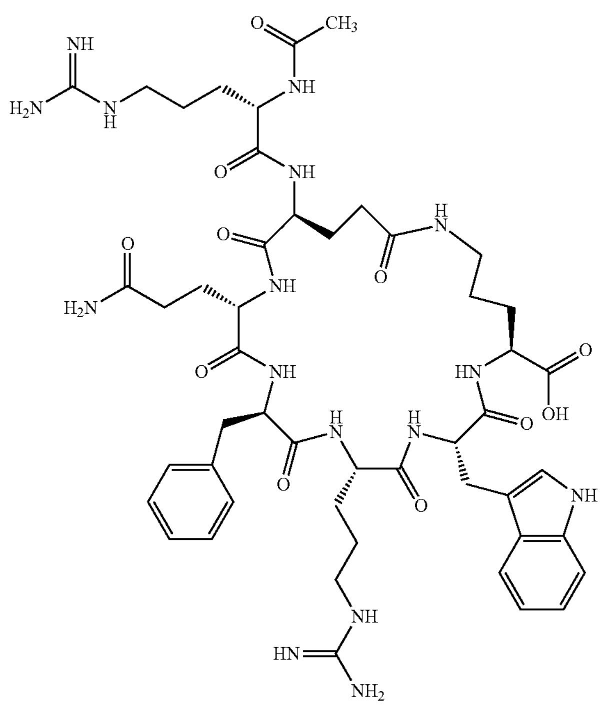 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCC(N)=O)NC1=O] | Ac-Arg-cyclo(Glu-Gln-D-Phe-Arg-Trp-Orn)-OH |

TABLE 1-continued

| No. | Structure | Primary Sequence |
|-----|-----------|------------------|
| 12 | 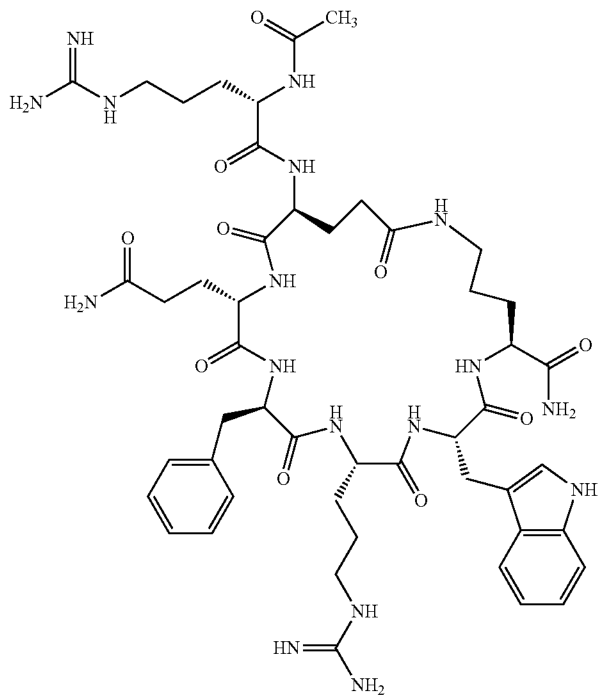 | Ac-Arg-cyclo(Glu-Gln-D-Phe-Arg-Trp-Orn)-NH$_2$ |
| 13 | 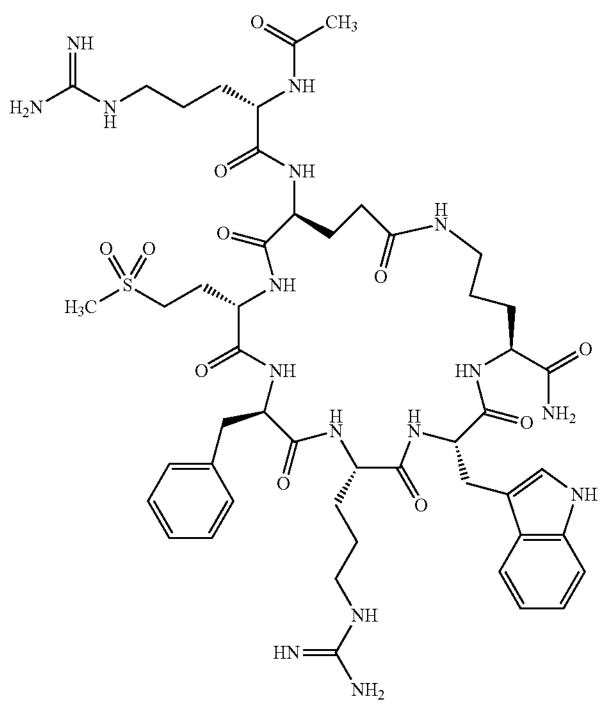 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCS(C)(=O)=O)NC1=O] | Ac-Arg-cyclo(Glu-Met(O$_2$)-D-Phe-Arg-Trp-Orn)-NH$_2$ |

| No. | Structure | Primary Sequence |
|---|---|---|
| 14 | 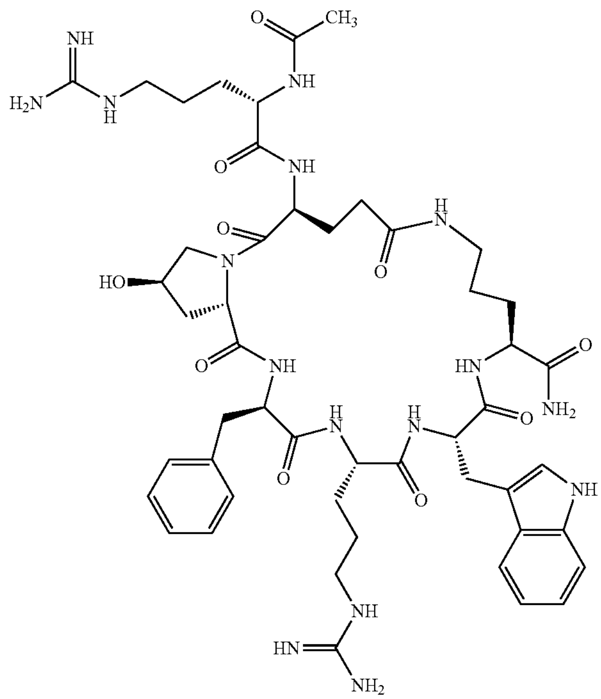 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H]2C[C@@H](O)CN2C1=O] | Ac-Arg-cyclo(Glu-Hyp-D-Phe-Arg-Trp-Orn)-NH$_2$ |
| 15 | 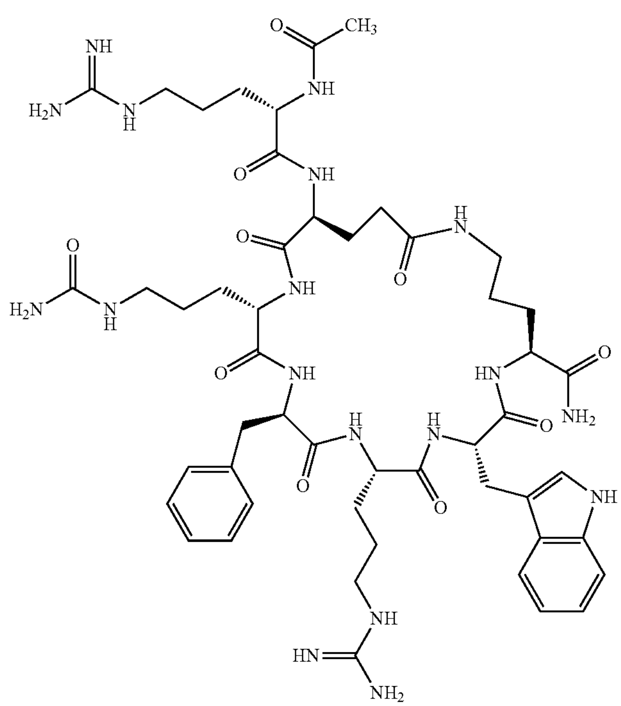 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCCNC(N)=O)NC1=O] | Ac-Arg-cyclo(Glu-Cit-D-Phe-Arg-Trp-Orn)-NH$_2$ |

TABLE 1-continued

| No. | Structure | Primary Sequence |
|---|---|---|
| 16 | 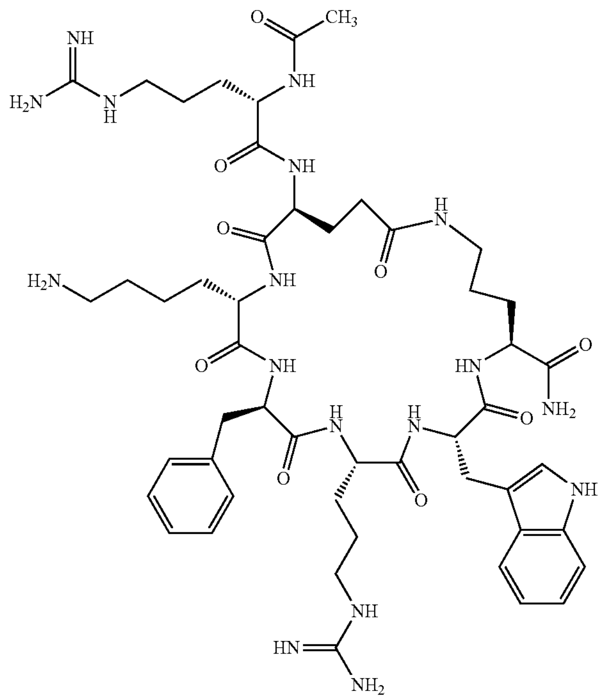 | Ac-Arg-cyclo(Glu-Lys-D-Phe-Arg-Trp-Orn)-NH$_2$ |
| 17 | 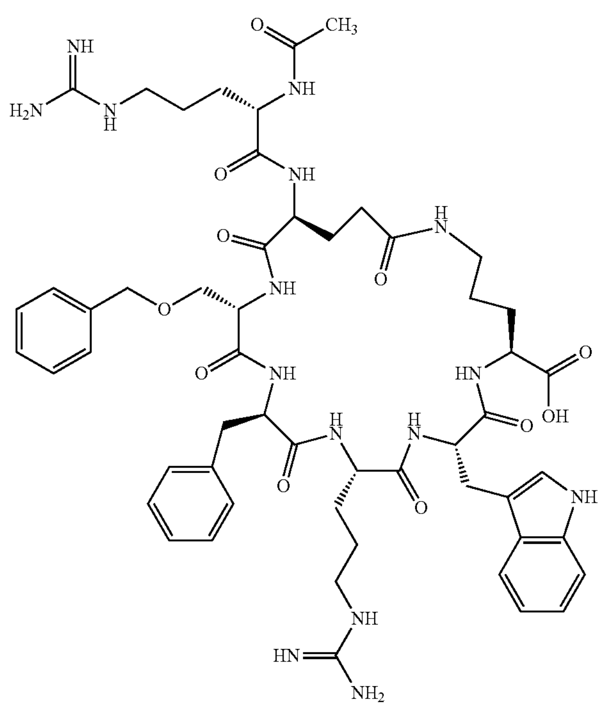 [SMILES: CC(=O)N[C@@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](COCc2ccccc2)NC1=O] | Ac-Arg-cyclo(Glu-Ser(Bzl)-D-Phe-Arg-Trp-Orn)-OH |

TABLE 1-continued

| No. | Structure | Primary Sequence |
|---|---|---|
| 18 | 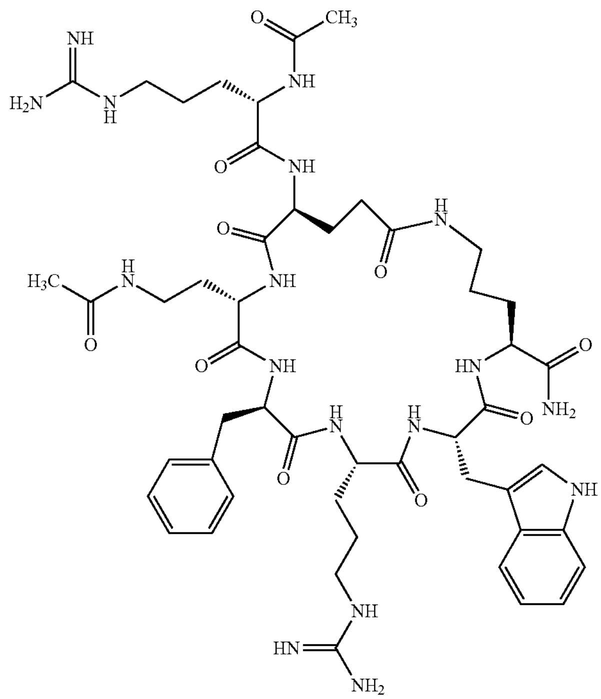 [SMILES: CC(=O)NCC[C@@H]1NC(=O)[C@@H](NC(=O)[C@H](CCCNC(=N)N)NC(C)=O)CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC1=O] | Ac-Arg-cyclo(Glu-Dab(Acetyl)-D-Phe-Arg-Trp-Orn)-NH$_2$ |
| 19 | 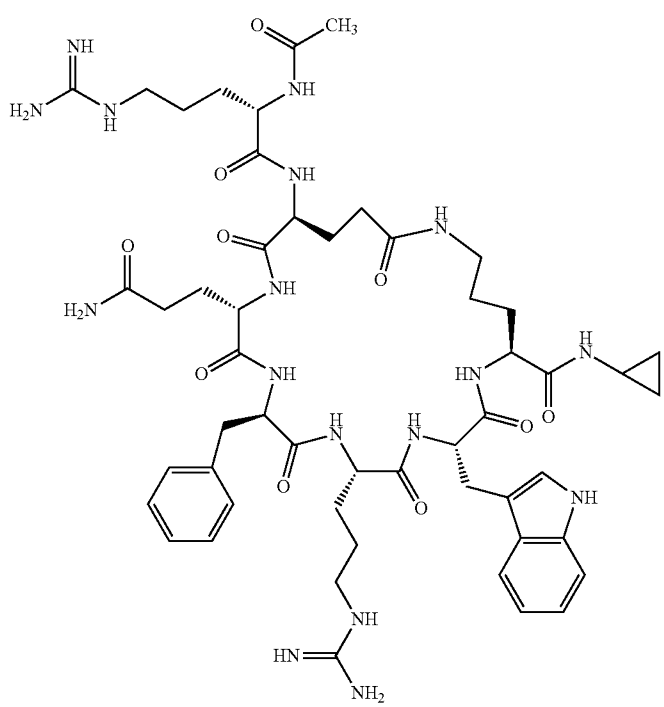 [SMILES: CC(=O)N[C@@H](CCCNC(=N)N)C(=O)N[C@H]1CCC(=O)NCCC[C@@H](C(=O)NC2CC2)NC(=O)[C@H](Cc2c[nH]c3ccccc23)NC(=O)[C@H](CCCNC(=N)N)NC(=O)[C@@H](Cc2ccccc2)NC(=O)[C@H](CCC(N)=O)NC1=O] | Ac-Arg-cyclo(Glu-Gln-D-Phe-Arg-Trp-Orn)-NH-cycProp |

TABLE 1-continued

| No. | Structure | Primary Sequence |
|---|---|---|
| 20 | 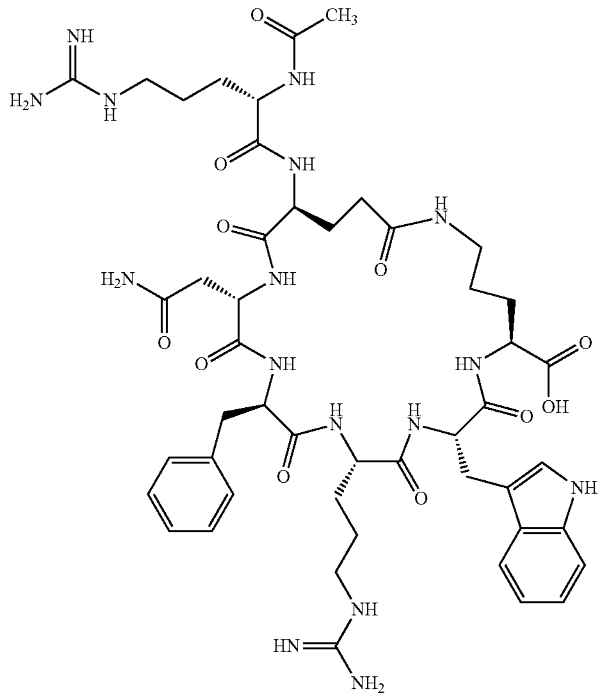 [SMILES: CC(=O)N[C@@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CC(N)=O)NC1=O] | Ac-Arg-cyclo(Glu-Asn-D-Phe-Arg-Trp-Orn)-OH |
| 21 | 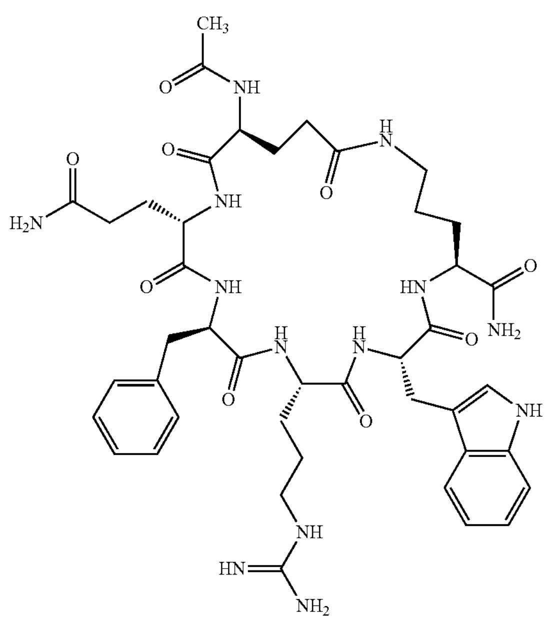 [SMILES: CC(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCC(N)=O)NC1=O] | Ac-cyclo(Glu-Gln-D-Phe-Arg-Trp-Orn)-NH$_2$ |

| No. | Structure | Primary Sequence |
|---|---|---|
| 22 | 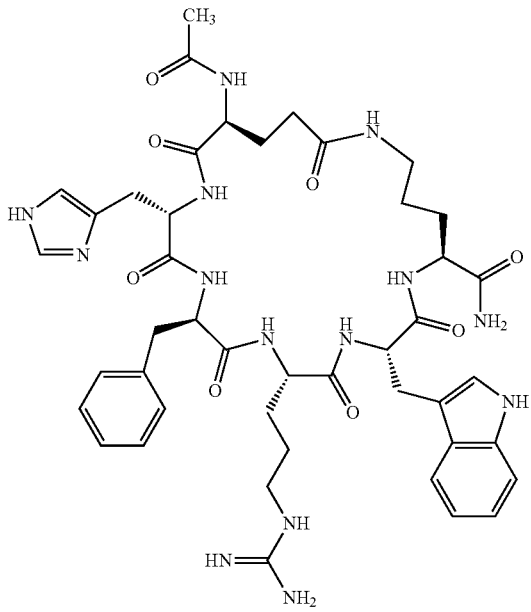 [SMILES: CC(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-cyclo(Glu-His-D-Phe-Arg-Trp-Orn)-NH$_2$ |
| 23 | 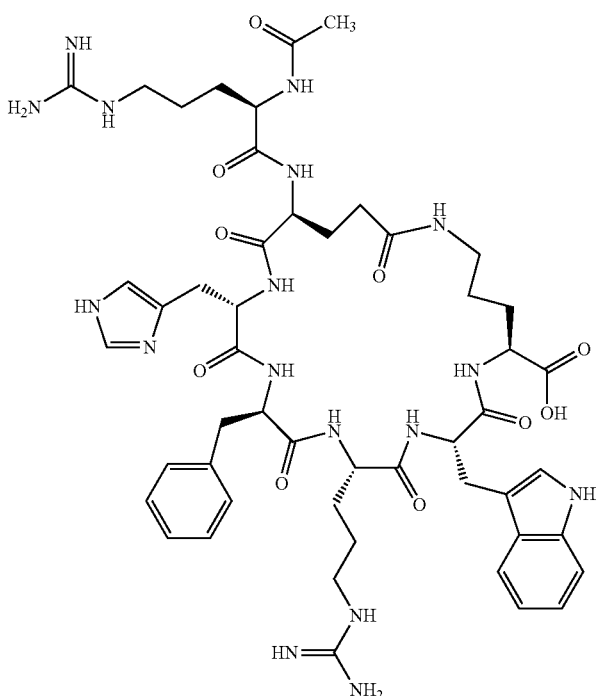 | Ac-D-Arg-cyclo(Glu-His-D-Phe-Arg-Trp-Orn)-OH |

TABLE 1-continued

| No. | Structure | Primary Sequence |
|---|---|---|
| 24 | 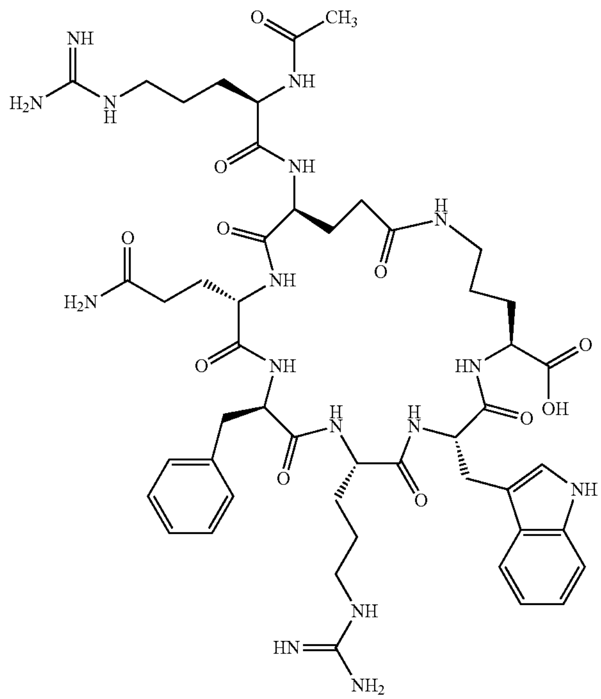 [SMILES: CC(=O)N[C@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CCC(N)=O)NC1=O] | Ac-D-Arg-cyclo(Glu-Gln-D-Phe-Arg-Trp-Orn)-OH |
| 25 | 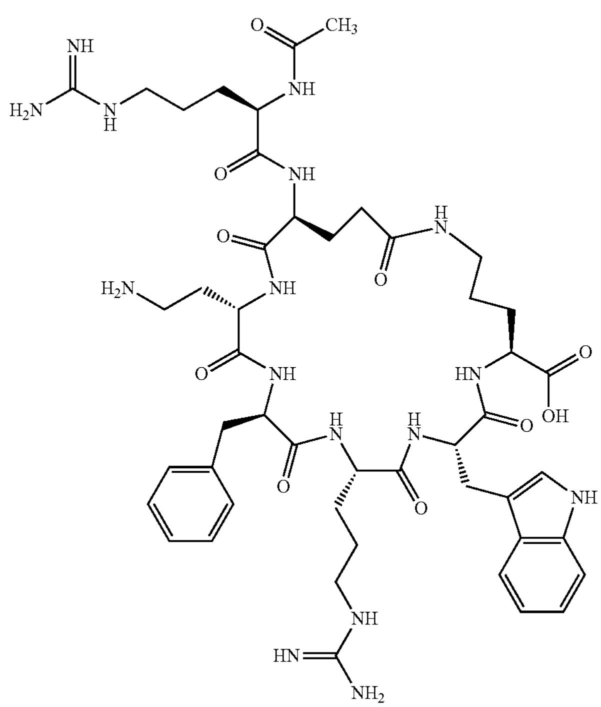 [SMILES: CC(=O)N[C@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Ac-D-Arg-cyclo(Glu-Dab-D-Phe-Arg-Trp-Orn)-OH |

TABLE 1-continued

| No. | Structure | Primary Sequence |
|---|---|---|
| 26 | 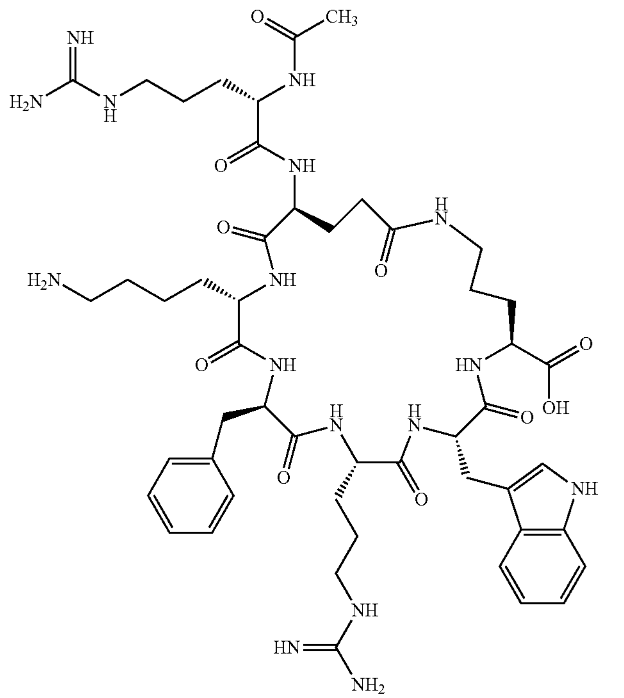 [SMILES: CC(=O)N[C@@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CCCCN)NC1=O] | Ac-Arg-cyclo(Glu-Lys-D-Phe-Arg-Trp-Orn)-OH |
| 27 | 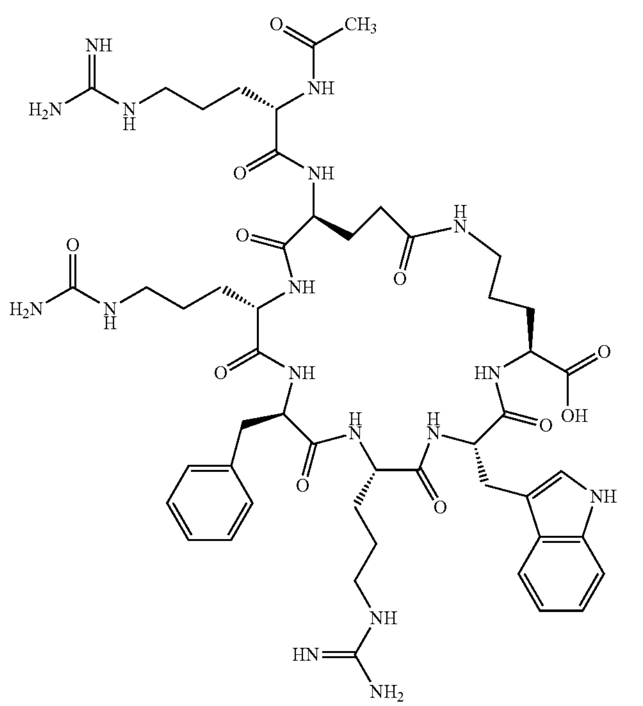 [SMILES: CC(=O)N[C@@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CCCNC(N)=O)NC1=O] | Ac-Arg-cyclo(Glu-Cit-D-Phe-Arg-Trp-Orn)-OH |

TABLE 1-continued

| No. | Structure | Primary Sequence |
|---|---|---|
| 28 | 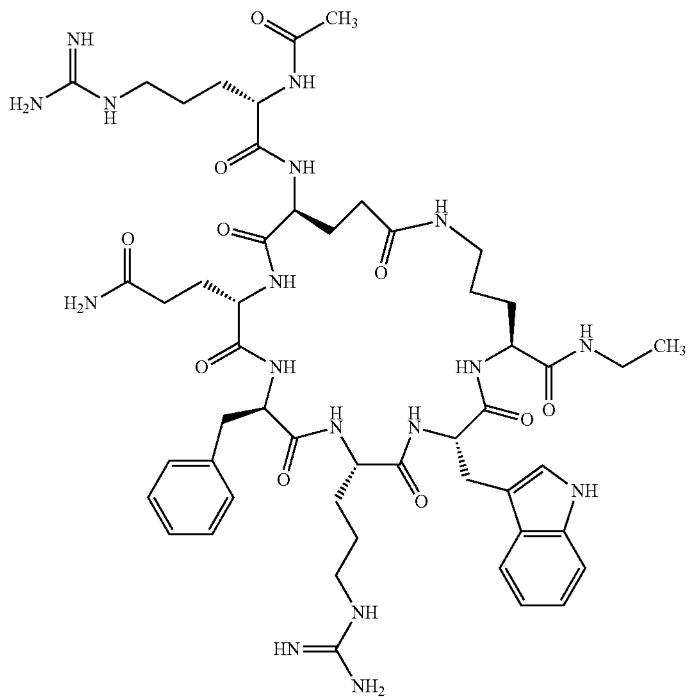 [SMILES: CCNC(=O)[C@@H]1CCCNC(=O)CC[C@H](NC(=O)[C@H](CCCNC(=N)N)NC(C)=O)C(=O)N[C@@H](CCC(N)=O)C(=O)N[C@H](Cc2ccccc2)C(=O)N[C@@H](CCCNC(=N)N)C(=O)N[C@@H](Cc2c[nH]c3ccccc23)C(=O)N1] | Ac-Arg-cyclo(Glu-Gln-D-Phe-Arg-Trp-Orn)-NHEt |
| 29 | 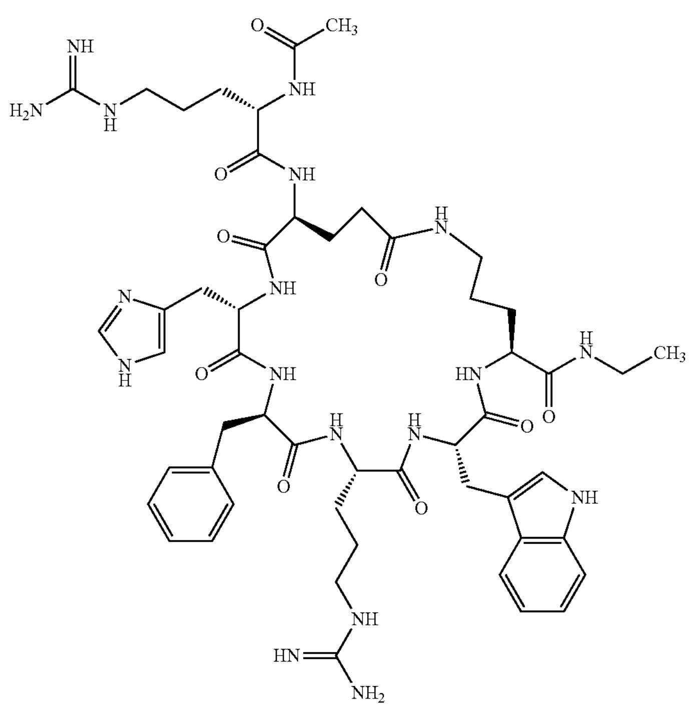 [SMILES: CCNC(=O)[C@@H]1CCCNC(=O)CC[C@H](NC(=O)[C@H](CCCNC(=N)N)NC(C)=O)C(=O)N[C@@H](Cc2c[nH]cn2)C(=O)N[C@H](Cc2ccccc2)C(=O)N[C@@H](CCCNC(=N)N)C(=O)N[C@@H](Cc2c[nH]c3ccccc23)C(=O)N1] | Ac-Arg-cyclo(Glu-His-D-Phe-Arg-Trp-Orn)-NHEt |

TABLE 1-continued

| No. | Structure | Primary Sequence |
|---|---|---|
| 30 | 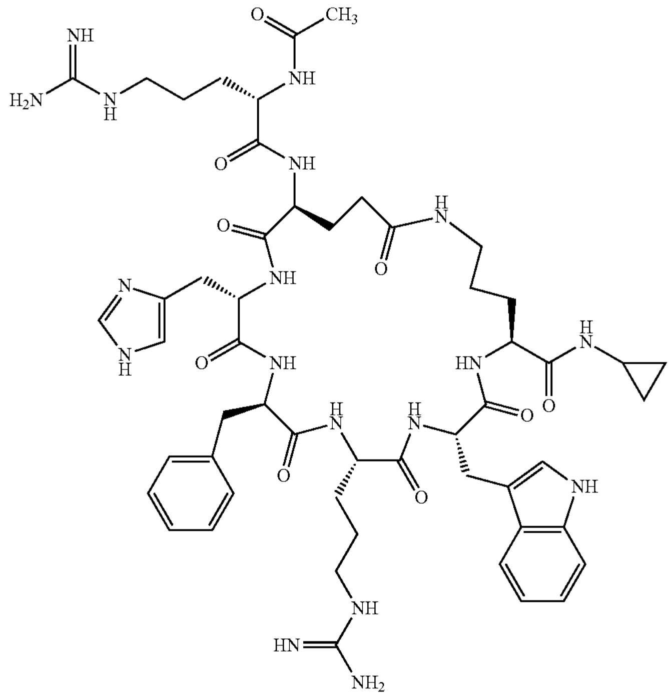 [SMILES: CC(=O)N[C@@H](CCCNC(=N)N)C(=O)N[C@H]1CCC(=O)NCCC[C@@H](C(=O)NC2CC2)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-Arg-cyclo(Glu-His-D-Phe-Arg-Trp-Orn)-NH-cycProp |
| 31 | 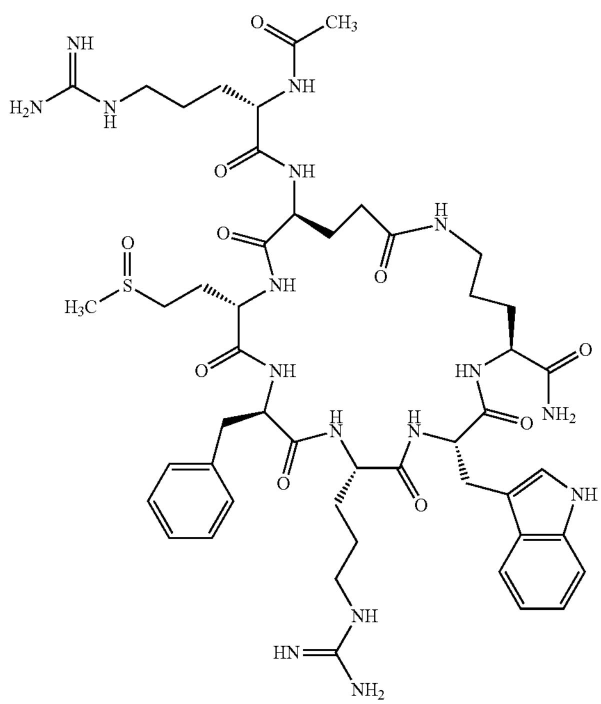 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCS(C)=O)NC1=O] | Ac-Arg-cyclo(Glu-Met(O)-His-D-Phe-Arg-Trp-Orn)-NH₂ |

TABLE 1-continued

| No. | Structure | Primary Sequence |
|---|---|---|
| 32 | 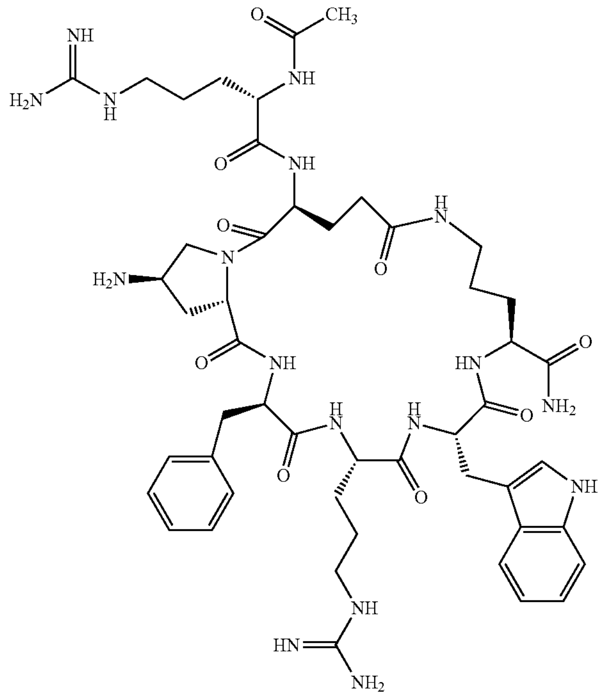 | Ac-Arg-cyclo(Glu-Pro(4R-NH$_2$)-D-Phe-Arg-Trp-Orn)-NH$_2$ |
| 33 | 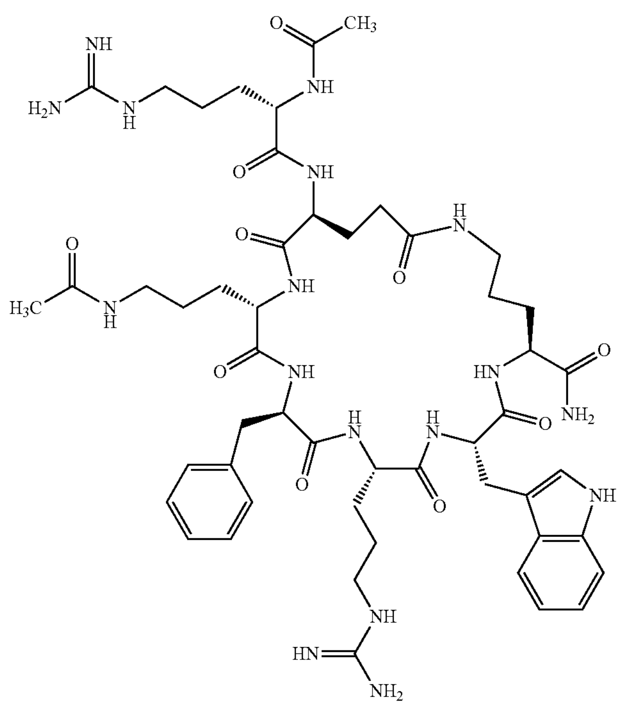 | Ac-Arg-cyclo(Glu-Orn(Acetyl)-D-Phe-Arg-Trp-Orn)-NH$_2$ |

TABLE 1-continued

| No. | Structure | Primary Sequence |
|---|---|---|
| 34 | 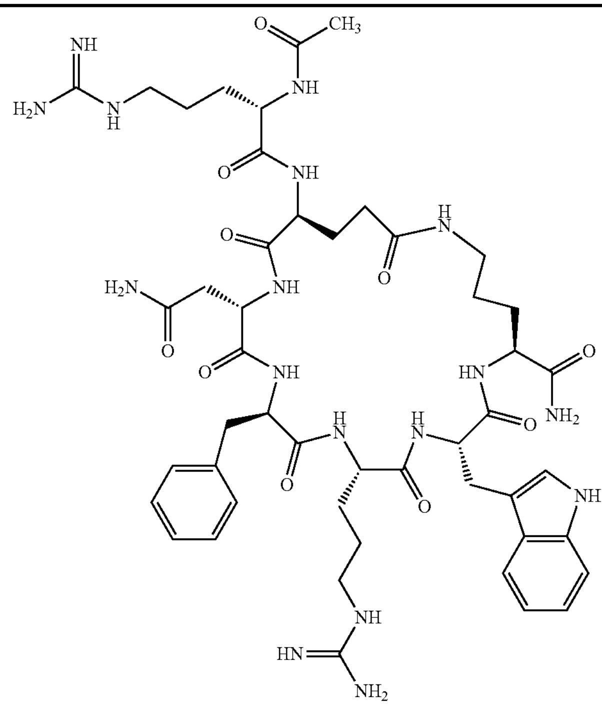 | Ac-Arg-cyclo(Glu-Asn-D-Phe-Arg-Trp-Orn)-NH$_2$ |

TABLE 2

| No. | Structure | Primary Sequence |
|---|---|---|
| 35 | 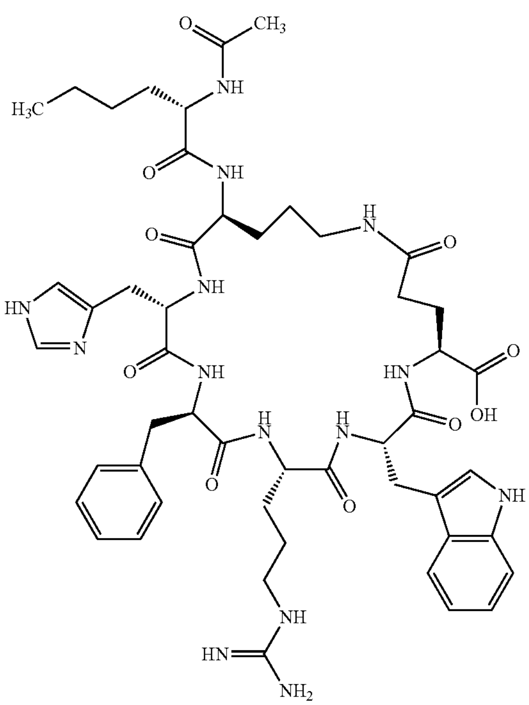 [SMILES: CCCC[C@H](NC(C)=O)C(=O)N[C@H]1CCCNC(=O)CC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-Nle-cyclo(Orn-His-D-Phe-Arg-Trp-Glu)-OH |

TABLE 2-continued

| No. | Structure | Primary Sequence |
|---|---|---|
| 36 | 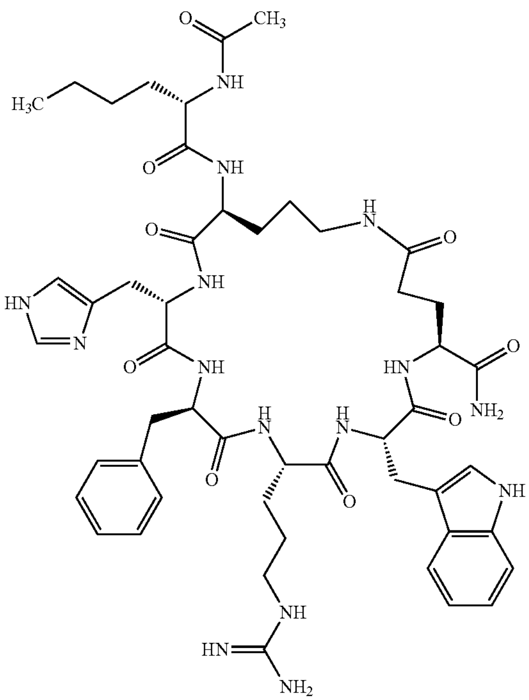 | Ac-Nle-cyclo(Orn-His-D-Phe-Arg-Trp-Glu)-NH$_2$ |
| 37 | 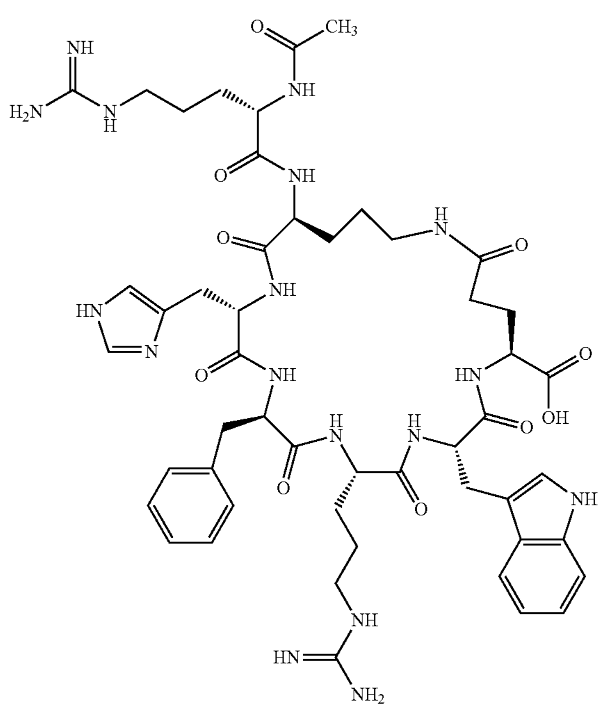 [SMILES: CC(=O)N[C@@H](CCCNC(=N)N)C(=O)N[C@H]1CCCNC(=O)CC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-Arg-cyclo(Orn-His-D-Phe-Arg-Trp-Glu)-OH |

TABLE 2-continued

| No. | Structure | Primary Sequence |
|-----|-----------|------------------|
| 38 | 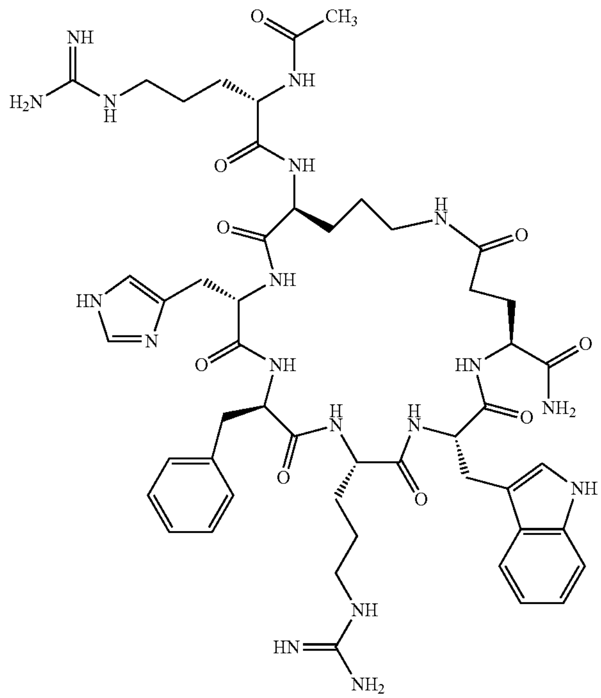 | Ac-Arg-cyclo(Orn-His-D-Phe-Arg-Trp-Glu)-NH$_2$ |
| 39 | 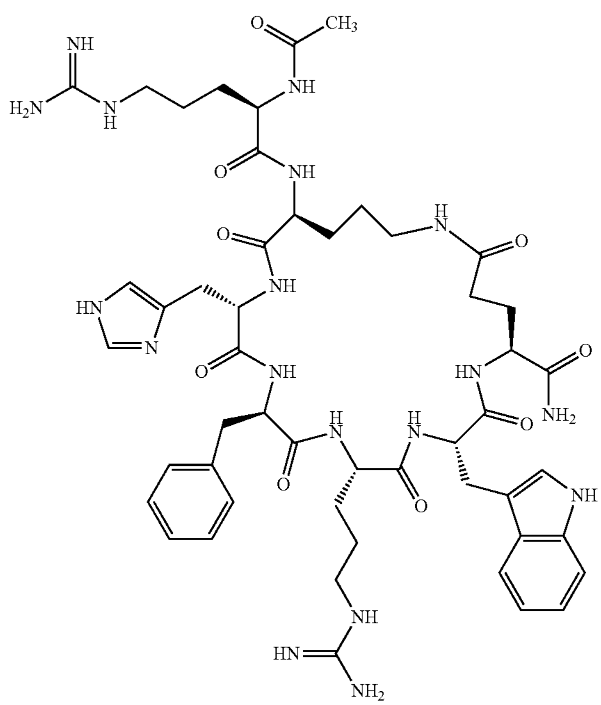 [SMILES: CC(=O)N[C@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-D-Arg-cyclo(Orn-His-D-Phe-Arg-Trp-Glu)-NH$_2$ |

TABLE 2-continued

| No. | Structure | Primary Sequence |
|---|---|---|
| 40 | 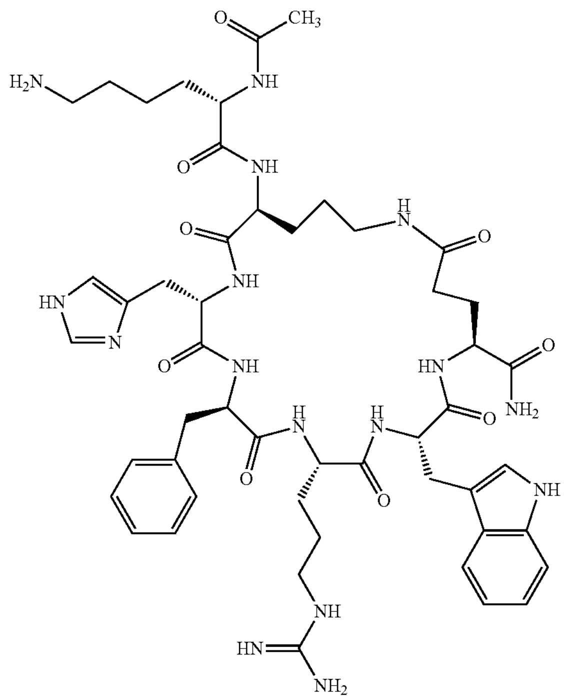 [SMILES: CC(=O)N[C@@H](CCCCN)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-Lys-cyclo(Orn-His-D-Phe-Arg-Trp-Glu)-NH$_2$ |
| 41 | 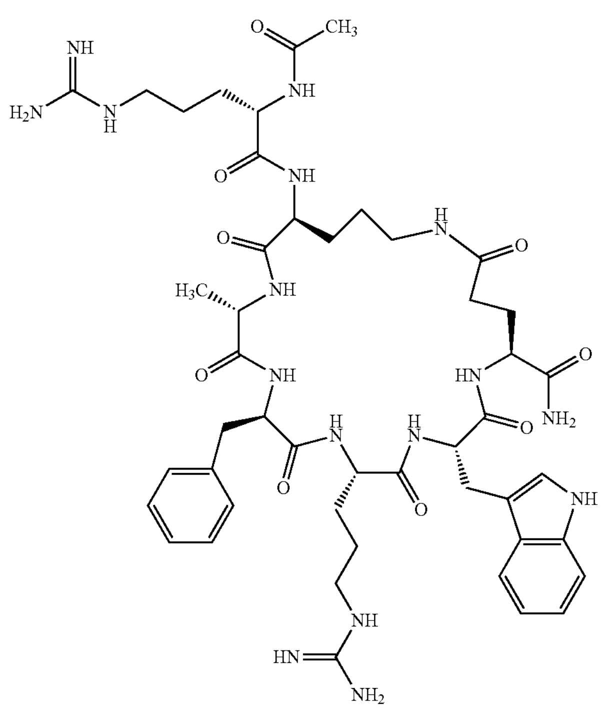 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](C)NC1=O] | Ac-Arg-cyclo(Orn-Ala-D-Phe-Arg-Trp-Glu)-NH$_2$ |

TABLE 2-continued

| No. | Structure | Primary Sequence |
|---|---|---|
| 42 | 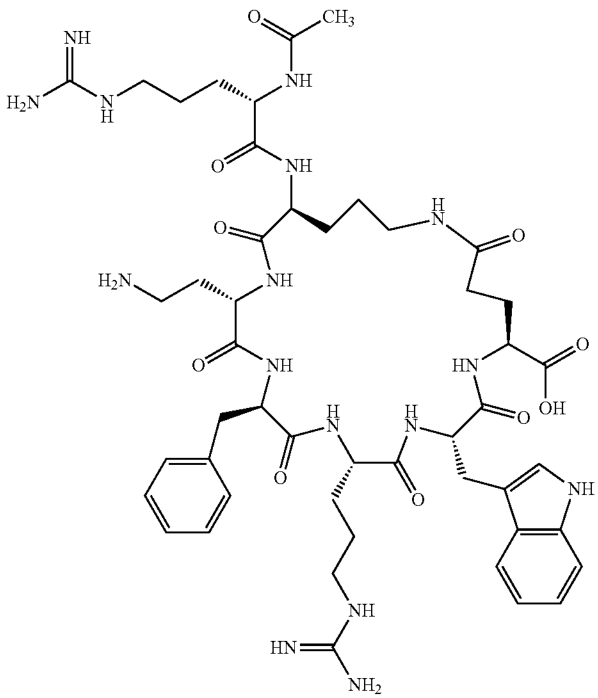 [SMILES: CC(=O)N[C@@H](CCCNC(=N)N)C(=O)N[C@H]1CCCNC(=O)CC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Ac-Arg-cyclo(Orn-Dab-D-Phe-Arg-Trp-Glu)-OH |
| 43 | 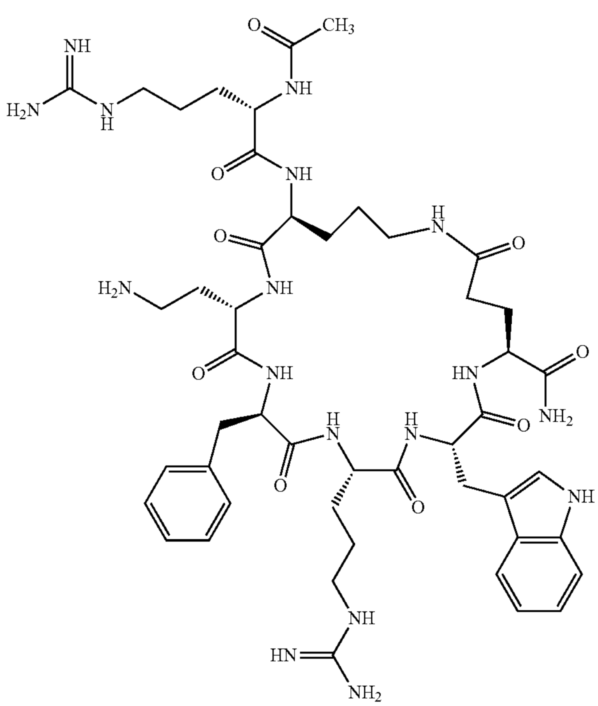 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Ac-Arg-cyclo(Orn-Dab-D-Phe-Arg-Trp-Glu)-NH$_2$ |

| No. | Structure | Primary Sequence |
|-----|-----------|------------------|
| 44 | 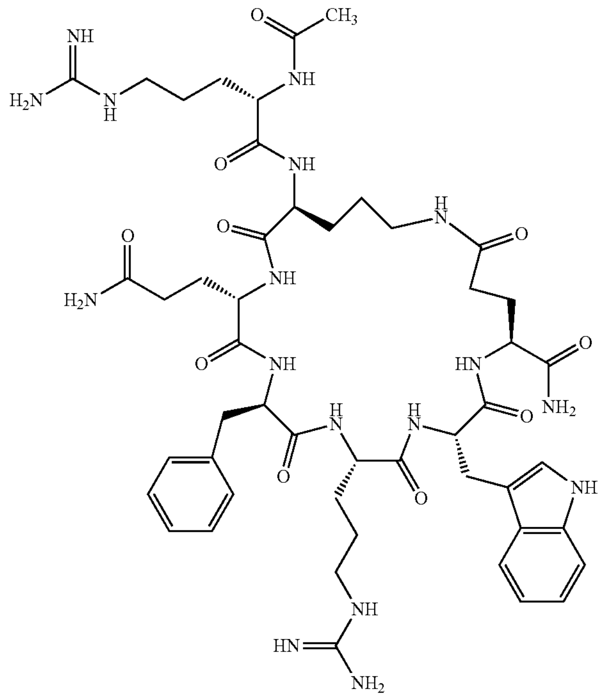 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCC(N)=O)NC1=O] | Ac-Arg-cyclo(Orn-Gln-D-Phe-Arg-Trp-Glu)-NH$_2$ |
| 45 | 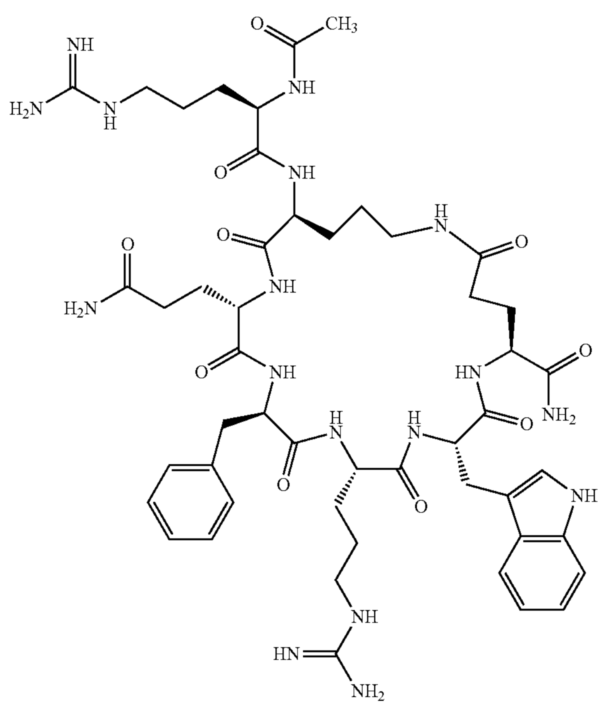 [SMILES: CC(=O)N[C@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCC(N)=O)NC1=O] | Ac-D-Arg-cyclo(Orn-Gln-D-Phe-Arg-Trp-Glu)-NH$_2$ |

TABLE 2-continued

| No. | Structure | Primary Sequence |
|---|---|---|
| 46 | 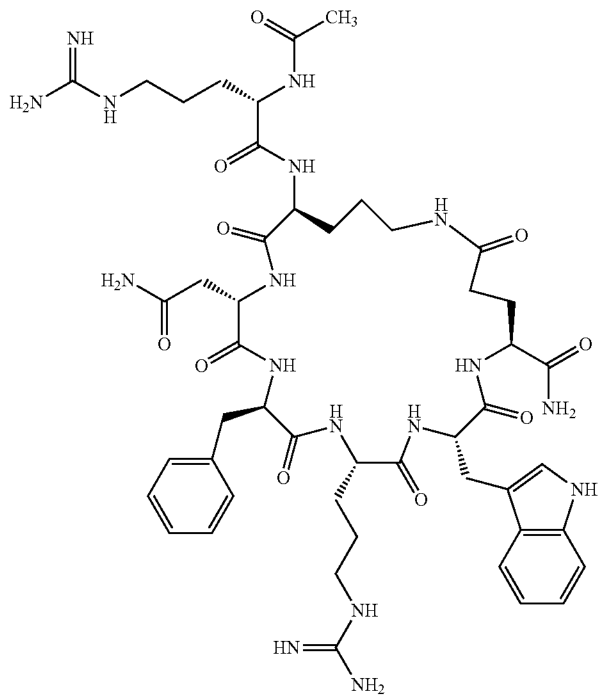 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CC(N)=O)NC1=O] | Ac-Arg-cyclo(Orn-Asn-D-Phe-Arg-Trp-Glu)-NH$_2$ |
| 47 | 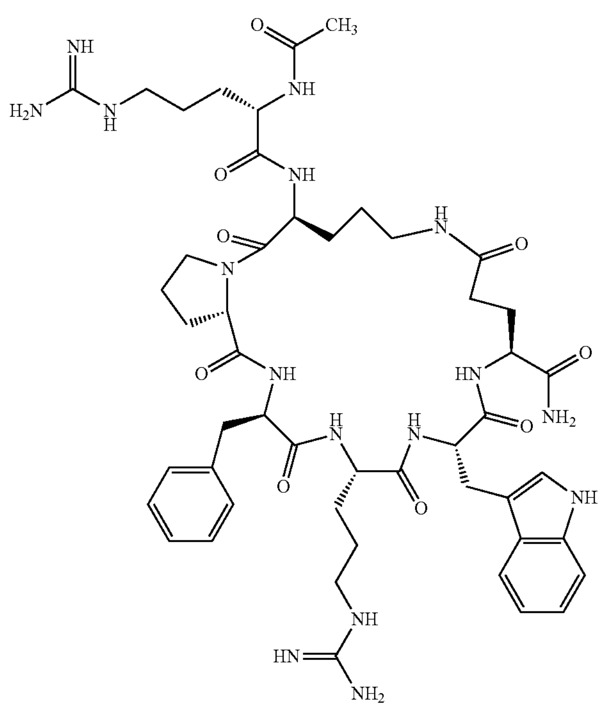 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H]2CCCN2C1=O] | Ac-Arg-cyclo(Orn-Pro-D-Phe-Arg-Trp-Glu)-NH$_2$ |

TABLE 2-continued

| No. | Structure | Primary Sequence |
|-----|-----------|------------------|
| 48 | (structure) | Ac-Arg-cyclo(Orn-Ser(Bzl)-D-Phe-Arg-Trp-Glu)-OH |

9.0 Comparison of Peptides of the Present Invention

Peptides of the present invention as shown in Tables 1 and 2 above were compared against analogs otherwise identical but which utilize an art conventional cyclization through Asp and Lys side chains such that the lactam bridge has the structure —$CH_2$—C(=O)—NH—$(CH_2)_4$— from backbone carbon to backbone carbon.

9.1 Assay Systems Employed.

Peptides were tested for Ki values at human MC4-R using [$I^{125}$]-NDP-α-MSH as described in section 7.1 above or Eu-NDP-α-MSH as described in section 7.2 above. $EC_{50}$ and $E_{max}$ values were determined as generally described in sections 7.3 and 7.4 above, with functional activity at human MC4-R measured by a cAMP assay in HEK-293 cells constructed using the T-REx™ System and induced with doxycycline at a concentration of 0.1 ng/mL to produce a functional response similar to that with endogenous cell lines such as GT1-7.

9.2 Binding and Functional Data

Table 3 below shows binding affinities (Ki) and functional activities ($EC_{50}$ and $E_{max}$) for certain peptides of the invention ("Peptide Structure Glu . . . Orn") together with corresponding data for analogs cyclized through Asp and Lys side chains ("Peptide structure Asp . . . Lys"). The reported values are averages of all comparable assays.

Table 4 below shows binding affinities (Ki) and functional activities ($EC_{50}$ and $E_{max}$) for certain peptides of the invention ("Peptide Structure Orn . . . Glu") together with corresponding data for analogs cyclized through Asp and Lys side chains ("Peptide structure Asp . . . Lys"). The reported values are averages of all comparable assays.

TABLE 3

| Peptide Structure (Asp . . . Lys) | $K_i$ (nM) | $Ec_{50}$ (nM) | $E_{max}$ (%) | No. |
|---|---|---|---|---|
| Ac-Nle-Asp-His-DPhe-Arg-Trp-Lys-OH | 4 | 2 | 81 | 1 |
| Ac-Nle-Asp-His-DPhe-Arg-Trp-Lys-$NH_2$ | 0.4 | 2 | 78 | 2 |
| Ac-Arg-Asp-His-DPhe-Arg-Trp-Lys-OH | 22 | 4 | 91 | 3 |
| Ac-Arg-Asp-His-DPhe-Arg-Trp-Lys-$NH_2$ | 2 | 1 | 83 | 4 |
| Ac-Arg-Asp-Dab-DPhe-Arg-Trp-Lys-OH | 56 | 4 | 91 | 5 |

TABLE 3-continued

| Peptide Structure | | | | |
|---|---|---|---|---|
| Ac-Arg-Asp-Dab-DPhe-Arg-Trp-Lys-NH$_2$ (cyclized Asp-Lys) | 4 | 0.3 | 91 | 6 |
| Ac-Arg-Asp-Orn-DPhe-Arg-Trp-Lys-OH (cyclized Asp-Lys) | 18 | 12 | 84 | 7 |
| Ac-Arg-Asp-Orn-DPhe-Arg-Trp-Lys-NH$_2$ (cyclized Asp-Lys) | 7 | 0.8 | 79 | 8 |
| Ac-Arg-Asp-Arg-DPhe-Arg-Trp-Lys-OH (cyclized Asp-Lys) | 60 | 28 | 75 | 9 |
| Ac-Arg-Asp-Arg-DPhe-Arg-Trp-Lys-NH$_2$ (cyclized Asp-Lys) | 4 | 3 | 68 | 10 |
| Ac-Arg-Asp-Gln-DPhe-Arg-Trp-Lys-OH (cyclized Asp-Lys) | 115 | 19 | 80 | 11 |
| Ac-Arg-Asp-Gln-DPhe-Arg-Trp-Lys-NH$_2$ (cyclized Asp-Lys) | 13 | 17 | 85 | 12 |
| Ac-Arg-Asp-Asn-DPhe-Arg-Trp-Lys-OH (cyclized Asp-Lys) | 100 | 81 | 73 | 20 |
| Ac-Arg-Asp-Asn-DPhe-Arg-Trp-Lys-NH$_2$ (cyclized Asp-Lys) | 32 | 42 | 91 | 34 |
| Ac-Arg-Asp-Met(O$_2$)-DPhe-Arg-Trp-Lys-NH$_2$ (cyclized Asp-Lys) | 7 | 35 | 29 | 13 |
| Ac-Arg-Asp-Hyp-DPhe-Arg-Trp-Lys-NH$_2$ (cyclized Asp-Lys) | 4 | 27 | 39 | 14 |
| Ac-Arg-Asp-Cit-DPhe-Arg-Trp-Lys-NH$_2$ (cyclized Asp-Lys) | 14 | 28 | 69 | 15 |
| Ac-Arg-Asp-Lys-DPhe-Arg-Trp-Lys-NH$_2$ (cyclized Asp-Lys) | 30 | 8 | 97 | 16 |
| Ac-Arg-Asp-Pro(4R-NH$_2$)-DPhe-Arg-Trp-Lys-NH$_2$ (cyclized Asp-Lys) | 5 | 8 | 61 | 32 |
| Ac-Arg-Asp-Orn(Acetyl)-DPhe-Arg-Trp-Lys-NH$_2$ (cyclized Asp-Lys) | 573 | 532 | 62 | 33 |
| Ac-Arg-Asp-Ser(Bzl)-DPhe-Arg-Trp-Lys-OH (cyclized Asp-Lys) | 9 | 5 | 38 | 17 |
| Ac-Arg-Asp-Dab(Acetyl)-DPhe-Arg-Trp-Lys-NH$_2$ (cyclized Asp-Lys) | 33 | 28 | 69 | 18 |
| Ac-Arg-Asp-Gln-DPhe-Arg-Trp-Lys-NH-cycProp (cyclized Asp-Lys) | 64 | 9 | 79 | 19 |
| Ac-Asp-Gln-DPhe-Arg-Trp-Lys-NH$_2$ (cyclized Asp-Lys) | 99 | 148 | 35 | 21 |

| Peptide Structure (Glu . . . Orn) | K$_i$ (nM) | Ec$_{50}$ (nM) | E$_{max}$ (%) |
|---|---|---|---|
| Ac-Nle-Glu-His-DPhe-Arg-Trp-Orn-OH (cyclized Glu-Orn) | 2 | 0.5 | 97 |
| Ac-Nle-Glu-His-DPhe-Arg-Trp-Orn-NH$_2$ (cyclized Glu-Orn) | 0.1 | 0.1 | 93 |
| Ac-Arg-Glu-His-DPhe-Arg-Trp-Orn-OH (cyclized Glu-Orn) | 24 | 0.7 | 83 |

TABLE 3-continued

| Sequence | | | |
|---|---|---|---|
| Ac-Arg-Glu-His-DPhe-Arg-Trp-Orn-NH₂ (cyclic) | 1 | 0.2 | 83 |
| Ac-Arg-Glu-Dab-DPhe-Arg-Trp-Orn-OH (cyclic) | 48 | 2 | 94 |
| Ac-Arg-Glu-Dab-DPhe-Arg-Trp-Orn-NH₂ (cyclic) | 4 | 0.3 | 94 |
| Ac-Arg-Glu-Orn-DPhe-Arg-Trp-Orn-OH (cyclic) | 51 | 4 | 92 |
| Ac-Arg-Glu-Orn-DPhe-Arg-Trp-Orn-NH₂ (cyclic) | 9 | 0.4 | 95 |
| Ac-Arg-Glu-Arg-DPhe-Arg-Trp-Orn-OH (cyclic) | 37 | 2 | 82 |
| Ac-Arg-Glu-Arg-DPhe-Arg-Trp-Orn-NH₂ (cyclic) | 4 | 0.7 | 98 |
| Ac-Arg-Glu-Gln-DPhe-Arg-Trp-Orn-OH (cyclic) | 43 | 5 | 81 |
| Ac-Arg-Glu-Gln-DPhe-Arg-Trp-Orn-NH₂ (cyclic) | 3 | 6 | 96 |
| Ac-Arg-Glu-Asn-DPhe-Arg-Trp-Orn-OH (cyclic) | 167 | 12 | 76 |
| Ac-Arg-Glu-Asn-DPhe-Arg-Trp-Orn-NH₂ (cyclic) | 6 | 0.4 | 91 |
| Ac-Arg-Glu-Met(O₂)-DPhe-Arg-Trp-Orn-NH₂ (cyclic) | 8 | 5 | 71 |
| Ac-Arg-Glu-Hyp-DPhe-Arg-Trp-Orn-NH₂ (cyclic) | 3 | 3 | 104 |
| Ac-Arg-Glu-Cit-DPhe-Arg-Trp-Orn-NH₂ (cyclic) | 6 | 2 | 87 |
| Ac-Arg-Glu-Lys-DPhe-Arg-Trp-Orn-NH₂ (cyclic) | 15 | 2 | 104 |
| Ac-Arg-Glu-Pro(4R-NH₂)-DPhe-Arg-Trp-Orn-NH₂ (cyclic) | 6 | 8 | 55 |
| Ac-Arg-Glu-Orn(Acetyl)-DPhe-Arg-Trp-Orn-NH₂ (cyclic) | 7 | 3 | 90 |
| Ac-Arg-Glu-Ser(Bzl)-DPhe-Arg-Trp-Orn-OH (cyclic) | 6 | 2 | 55 |
| Ac-Arg-Glu-Dab(Acetyl)-DPhe-Arg-Trp-Orn-NH₂ (cyclic) | 13 | 4 | 75 |
| Ac-Arg-Glu-Gln-DPhe-Arg-Trp-Orn-NH-cycProp (cyclic) | 26 | 1 | 91 |
| Ac-Glu-Gln-DPhe-Arg-Trp-Orn-NH₂ (cyclic) | 74 | 26 | 49 |

TABLE 4

| Peptide Structure (Asp . . . Lys) | $K_i$ (nM) | $Ec_{50}$ (nM) | $E_{max}$ (%) | No. |
|---|---|---|---|---|
| Ac-Nle-Asp-His-DPhe-Arg-Trp-Lys-OH | 4 | 2 | 81 | 35 |
| Ac-Nle-Asp-His-DPhe-Arg-Trp-Lys-NH$_2$ | 0.4 | 2 | 78 | 36 |
| Ac-Arg-Asp-His-DPhe-Arg-Trp-Lys-OH | 22 | 4 | 91 | 37 |
| Ac-Arg-Asp-His-DPhe-Arg-Trp-Lys-NH$_2$ | 2 | 1 | 83 | 38 |
| Ac-DArg-Asp-His-DPhe-Arg-Trp-Lys-NH$_2$ | 8 | 0.6 | 89 | 39 |
| Ac-Lys-Asp-His-DPhe-Arg-Trp-Lys-NH$_2$ | 9 | 5 | 85 | 40 |
| Ac-Arg-Asp-Ala-DPhe-Arg-Trp-Lys-NH$_2$ | 19 | 37 | 74 | 41 |
| Ac-Arg-Asp-Dab-DPhe-Arg-Trp-Lys-OH | 56 | 4 | 91 | 42 |
| Ac-Arg-Asp-Dab-DPhe-Arg-Trp-Lys-NH$_2$ | 4 | 0.3 | 91 | 43 |
| Ac-Arg-Asp-Gln-DPhe-Arg-Trp-Lys-NH$_2$ | 13 | 17 | 85 | 44 |
| Ac-DArg-Asp-Gln-DPhe-Arg-Trp-Lys-NH$_2$ | 45 | 2 | 89 | 45 |
| Ac-Arg-Asp-Asn-DPhe-Arg-Trp-Lys-NH$_2$ | 32 | 42 | 91 | 46 |
| Ac-Arg-Asp-Pro-DPhe-Arg-Trp-Lys-NH$_2$ | 17 | 9 | 43 | 47 |
| Ac-Arg-Asp-Ser(Bzl)-DPhe-Arg-Trp-Lys-OH | 9 | 5 | 38 | 48 |

| Peptide Structure (Glu . . . Orn) | $K_i$ (nM) | $Ec_{50}$ (nM) | $E_{max}$ (%) |
|---|---|---|---|
| Ac-Nle-Orn-His-DPhe-Arg-Trp-Glu-OH | 1 | 2 | 97 |
| Ac-Nle-Orn-His-DPhe-Arg-Trp-Glu-NH | 0.2 | 0.2 | 85 |
| Ac-Arg-Orn-His-DPhe-Arg-Trp-Glu-OH | 12 | 0.6 | 88 |
| Ac-Arg-Orn-His-DPhe-Arg-Trp-Glu-NH$_2$ | 1 | 1 | 84 |
| Ac-DArg-Orn-His-DPhe-Arg-Trp-Glu-NH$_2$ | 4 | 0.2 | 103 |
| Ac-Lys-Orn-His-DPhe-Arg-Trp-Glu-NH$_2$ | 3 | 0.2 | 114 |
| Ac-Arg-Orn-Ala-DPhe-Arg-Trp-Glu-NH$_2$ | 19 | 7 | 52 |
| Ac-Arg-Orn-Dab-DPhe-Arg-Trp-Glu-OH | 6 | 11 | 100 |

TABLE 4-continued

| | | | |
|---|---|---|---|
| Ac-Arg-Orn-Dab-DPhe-Arg-Trp-Glu-NH₂ (cyclized Orn–Glu) | 3 | 0.1 | 103 |
| Ac-Arg-Orn-Gln-DPhe-Arg-Trp-Glu-NH₂ (cyclized Orn–Glu) | 5 | 0.3 | 87 |
| Ac-DArg-Orn-Gln-DPhe-Arg-Trp-Glu-NH₂ (cyclized Orn–Glu) | 6 | 0.5 | 89 |
| Ac-Arg-Orn-Asn-DPhe-Arg-Trp-Glu-NH₂ (cyclized Orn–Glu) | 15 | 0.7 | 88 |
| Ac-Arg-Orn-Pro-DPhe-Arg-Trp-Glu-NH₂ (cyclized Orn–Glu) | 5 | 6 | 54 |
| Ac-Arg-Orn-Ser(Bzl)-DPhe-Arg-Trp-Glu-OH (cyclized Orn–Glu) | 5 | 3 | 50 |

Figure 3:
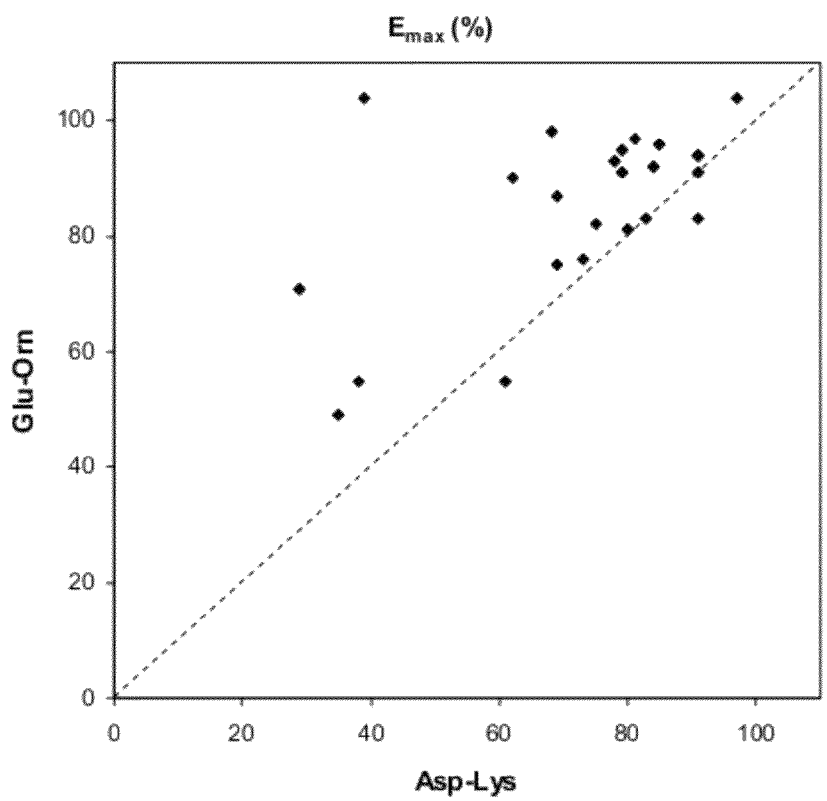
FIG. 3 is a plot of $E_{max}$ values of paired cyclic peptides of Table 3 before and after the side-chain lactam shift resulting from cyclization via Glu . . . Orn.

FIG. 3 shows the change of functional efficacy ($E_{max}$) due to the side-chain Glu . . . Orn lactam shift, utilizing data as reported in Table 3. In all instances but two, functional efficacies were improved or maintained utilizing cyclization through Glu . . . Orn, as compared to otherwise identical analogs cyclized through Asp . . . Lys. The improvement was most dramatic at the low end, with weak partial agonists demonstrating more significant improvement in functional efficacy than strong full agonists.

Figure 4:
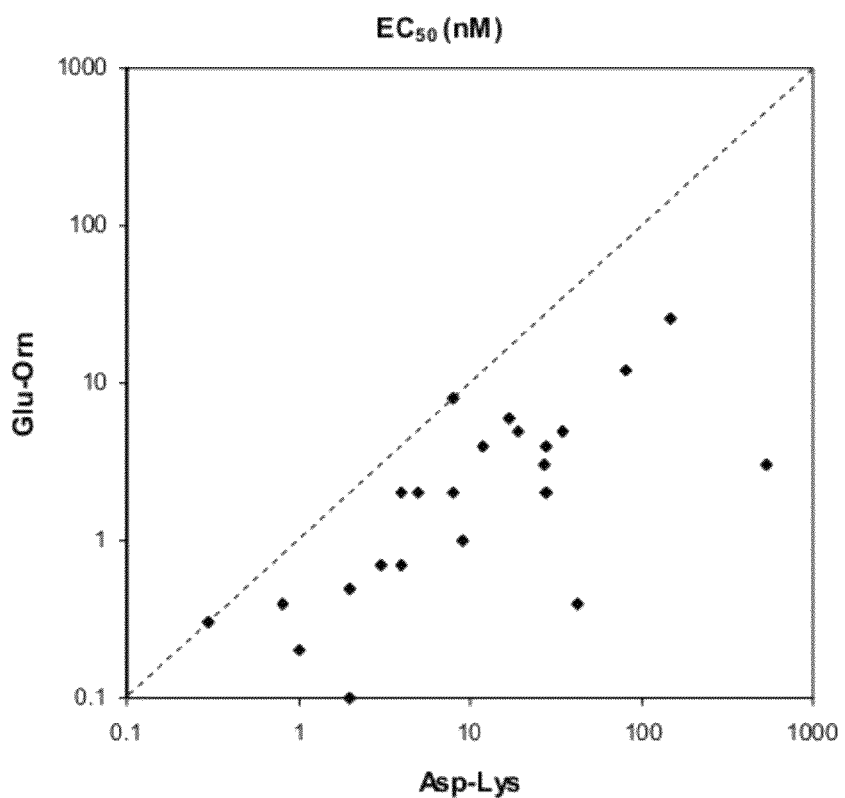
FIG. 4 is a plot of $EC_{50}$ values of paired cyclic peptides of Table 3 before and after the side-chain lactam shift resulting from cyclization via Glu . . . Orn.

FIG. 4 shows the change of functional potency ($EC_{50}$) caused by the side-chain Glu . . . Orn lactam shift, utilizing data as reported in Table 3. All the cyclic peptides demonstrate an improvement in or maintenance of functional potency after this shift.

Figure 5:
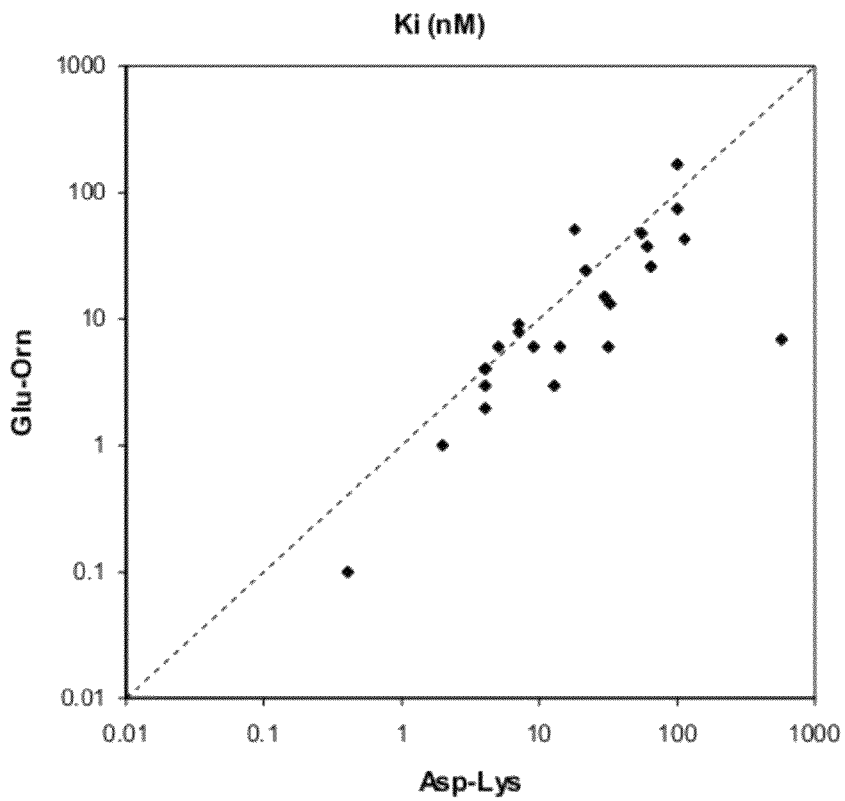
FIG. 5 is a plot of Ki values of paired cyclic peptides of Table 3 before and after the side-chain lactam shift resulting from cyclization via Glu . . . Orn.

As shown in FIG. 5, by contrast Ki values, representing binding affinity, did not show a consistent significant change after side-chain Glu . . . Orn lactam shift. Thus the observed improvement of MC4-R functional agonist activity, as shown in FIGS. 3 and 4 and Table 3, is not caused by an increase of binding affinity. This result supports the hypothesis that the shifted lactam group results in modified hydrogen bond interaction with His$^{264}$ which affects functional efficacy and potency without significantly or consistently increasing binding affinity.

As shown in Table 3, some peptides that were partial agonists with cyclization through Asp and Lys were converted to full agonists by cyclization through Glu and Orn. Accordingly, it may be that certain MC4-R neutral agonists or antagonists can be converted into full or partial agonists by utilizing cyclization through Glu and Orn.

Figure 6:
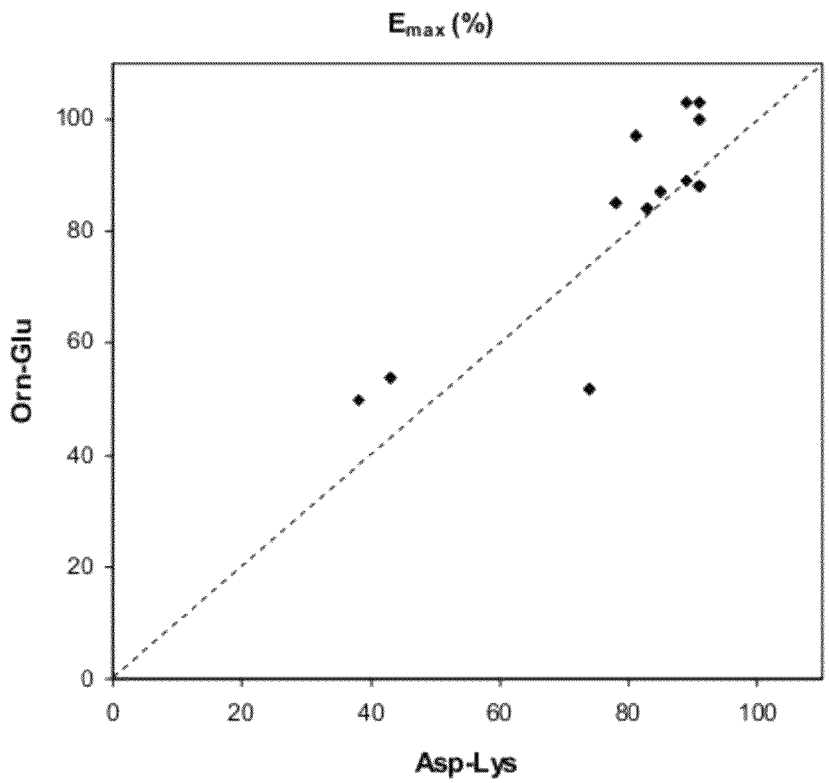
FIG. 6 is a plot of $E_{max}$ values of paired cyclic peptides of Table 4 before and after the side-chain lactam shift resulting from cyclization via Orn . . . Glu.

FIG. 6 shows the change of functional efficacy ($E_{max}$) due to the side-chain Orn . . . Glu lactam shift, utilizing data as reported in Table 4. In all instances but two, functional efficacies were improved or maintained utilizing cyclization through Orn . . . Glu, as compared to otherwise identical analogs cyclized through Asp . . . Lys. The improvement was most dramatic at the low end, with weak partial agonists demonstrating more significant improvement in functional efficacy than strong full agonists.

Figure 7:
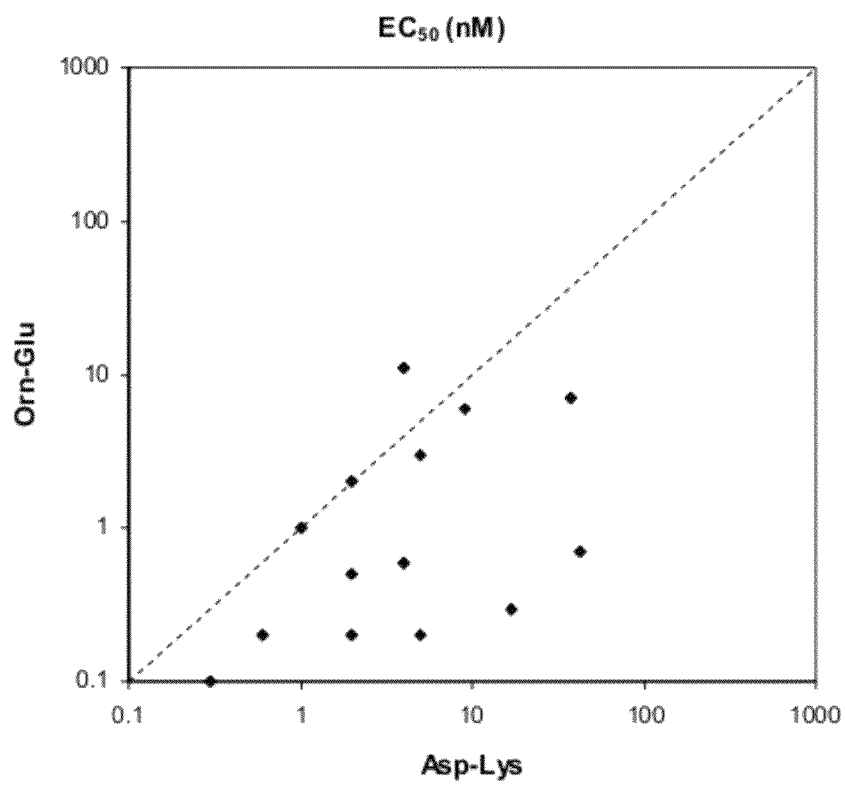
FIG. 7 is a plot of $EC_{50}$ values of paired cyclic peptides of Table 4 before and after the side-chain lactam shift resulting from cyclization via Orn . . . Glu.

FIG. 7 shows the change of functional potency ($EC_{50}$) caused by the side-chain Orn . . . Glu lactam shift, utilizing data as reported in Table 4. All but one cyclic peptide demonstrated an improvement in functional potency after this shift.

Figure 8:
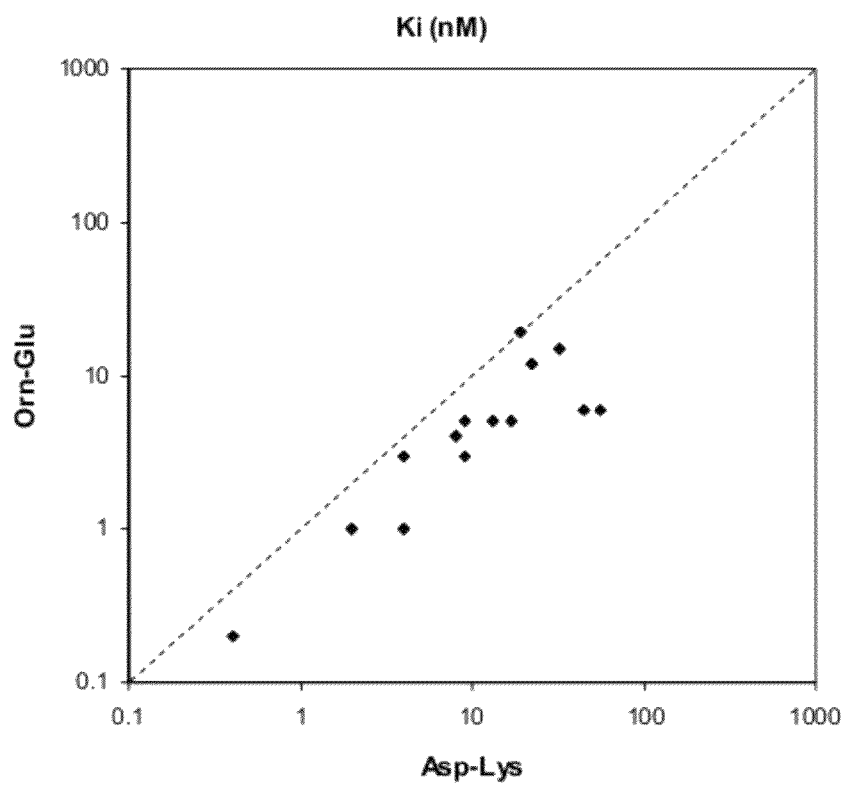
FIG. 8 is a plot of Ki values of paired cyclic peptides of Table 4 before and after the side-chain lactam shift resulting from cyclization via Orn . . . Glu.

As shown in FIG. 8, Ki values, representing binding affinity, also showed a slight but consistent change after the side-chain Orn . . . Glu lactam shift. Thus the observed improvement of MC4-R functional agonist activity, as shown in FIGS. 6 and 7 and Table 5, may also relate in part to an increase in binding affinity with Orn . . . Glu cyclized peptides compared to paired Asp . . . Lys peptides.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above are hereby incorporated by reference.

We claim:

1. A cyclic peptide of formula (I):

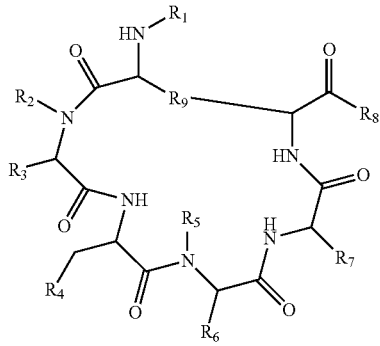

(I)

including all enantiomers, stereoisomers or diastereoisomers thereof, or a pharmaceutically acceptable salt of any of the foregoing, wherein:

$R_1$ is —$R_{10}$-$R_{11}$;

$R_2$ is —H, —$CH_3$ or —$CH_2$—, and if it is —$CH_2$— forms with $R_3$ a ring of the general structure

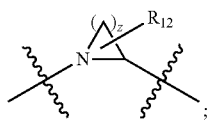

$R_3$ is —H, —$(CH_2)_z$— if $R_2$ is —$CH_2$—, and if it is —$(CH_2)_z$— forms the ring with $R_2$, or $R_3$ is —$(CH_2)_w$—$R_{13}$—$(CH_2)_w$—$R_{14}$, wherein any H in either $(CH_2)_w$ is optionally substituted with —$(CH_2)_w$—$CH_3$, $R_4$ is substituted or unsubstituted phenyl, but excluding substituted phenyl where —$R_{10}$-$R_{11}$ is Ac-Arg-;

$R_5$ is —H, —$CH_3$ or —$CH_2$—, and if it is —$CH_2$— forms with $R_6$ a ring of the general structure

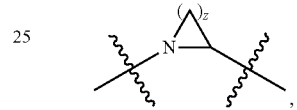

wherein the ring is optionally substituted;

$R_6$ is —$(CH_2)_z$— if $R_5$ is —$CH_2$—, and if it is —$(CH_2)_z$— forms the ring with $R_5$, or $R_6$ is —$(CH_2)_w$—$R_{15}$;

$R_7$ is —$(CH_2)_z$—$R_{16}$;

$R_8$ is —$R_{17}$—$R_{18}$;

$R_9$ is —$(CH_2)_2$—C(=O)—NH—$(CH_2)_3$— or —$(CH_2)_3$—$(CH_2)_3$—NH—C(=O)—$(CH_2)_2$—;

$R_{10}$ is optionally present, and if present, is from one to three L- or D-isomer amino acids, or a combination thereof;

$R_{11}$ is H or a $C_1$ to $C_7$ acyl group comprising a linear or branched alkyl, cycloalkyl, alkyl cycloalkyl, aryl or aralkyl;

$R_{12}$ is —H or —$R_{13}$—$(CH_2)_w$—$R_{14}$;

$R_{13}$ is optionally present, and if present is
—O—,
—S—,
—NH—,
—S(=O)$_2$—,
—S(=O)—,
—S(=O)$_2$—NH—,
—NH—S(=O)$_2$—,
—C(=O)—,
—C(=O)—O—,
—O—C(=O)—,
—NH—C(=O)—O—,
—O—C(=O)—NH—,
—NH—C(=O)—, or
—C(=O)—NH—;

$R_{14}$ is
—H,
—$CH_3$,
—N($R_{19a}$)($R_{19b}$),
—NH—$(CH_2)_z$—N($R_{19a}$)($R_{19b}$),
—NH—CH(=NH)—N($R_{19a}$)($R_{19b}$),
—NH—CH(=O)—N($R_{19a}$)($R_{19b}$),
—O($R_{19a}$),
—($R_{19a}$)($R_{19b}$),

—S(=O)$_2$(R$_{19a}$),
—C(=O)—O(R$_{19a}$),

[structures: pyrrole, imidazole, phenyl, cyclohexyl, cyclopentyl, pyrrolidine, indole, naphthalene, isoquinoline, quinoline, tetrahydronaphthalene, or —CH(R$_{19a}$)—O—R$_{19b}$]

wherein any ring in R$_{14}$ is optionally substituted with one or more ring substituents, and when one or more are present, are the same or different and independently hydroxyl, halogen, sulfonamide, alkyl, —O-alkyl, aryl, —O-aryl, C(=O)—OH, or C(=O)—N(R$_{19a}$)(R$_{19b}$);

R$_{15}$ is
—H,
—N(R$_{19a}$)(R$_{19b}$),
—NH—(CH$_2$)—N(R$_{19a}$)(R$_{19b}$),
—NH—CH(=NH)—N(R$_{19a}$)(R$_{19b}$),
—NH—CH(=O)—N(R$_{19a}$)(R$_{19b}$),
—O(R$_{19a}$),
—C$_1$ to C$_{17}$ linear, branched or cyclic alkyl chain,
—C(=O)—N(R$_{19a}$)(R$_{19b}$),
—S(=O)$_2$(R$_{19a}$),

[structures: —CH(R$_{19a}$)—O—R$_{19b}$, cyclopentadiene, pyrrole, imidazole, phenyl, or indole]

wherein any ring is optionally substituted with one or more optional ring substituents, and when one or more are present, are the same or different and independently hydroxyl, halogen, sulfonamide, alkyl, —O-alkyl, aryl, aralkyl, O-aralkyl, or —O-aryl;

R$_{16}$ is [structures: pyrrole, imidazole, phenyl, indole, naphthalene, isoquinoline, quinoline, or tetrahydronaphthalene], optionally substituted with one or more ring substituents, and when one or more are present, are the same or different and independently hydroxyl, halogen, sulfonamide, alkyl, —O-alkyl, aryl, or —O-aryl;

R$_{17}$ is optionally present, and if present, is from one to three L- or D-isomer amino acids, or a combination thereof;

R$_{18}$ is —OH, —N(R$_{19a}$)(R$_{19b}$) or —(CH$_2$)$_w$-cycloalkyl;

R$_{19a}$ and R$_{19b}$ are each independently H or a C$_1$ to C$_4$ linear, branched or cyclic alkyl chain;

w is in each instance independent 0 to 5; and z is in each instance independently 1 to 5;

but excluding cyclic peptides wherein R$_{10}$ is L- or D-Arg, R$_{11}$ is Ac, R$_2$ and R$_3$ together form unsubstituted pyrrolidine or R$_3$ is —(CH$_2$)$_2$—NH$_2$ or —CH$_2$—O—CH$_2$-phenyl, R$_4$ is unsubstituted phenyl, R$_5$ is H, R$_6$ is —(CH$_2$)$_3$—NH—C(=NH)—NH$_2$, R$_7$ is —CH$_2$-indole, R$_{17}$ is not present and R$_{18}$ is —OH or NH$_2$.

2. The cyclic peptide of claim 1 wherein R$_4$ is unsubstituted phenyl.

3. The cyclic peptide of claim 1 wherein R$_4$ is substituted phenyl with between one and three ring substituents wherein the substituents are the same or different, and are each independently halo, (C$_1$-C$_{10}$)alkyl-halo, (C$_1$-C$_{10}$)alkyl, (C$_1$-C$_{10}$) alkoxy, (C$_1$-C$_{10}$)alkylthio, aryl, (C$_1$-C$_{10}$)alkylaryl, aryloxy, nitro, nitrile, sulfonamide, amino, monosubstituted amino, disubstituted amino, hydroxy, carbamoyl, carboxy, carbamoyl, aryloxy-carbonyl, alkoxy-carbonyl, or aryloxy-carbonyl.

4. The cyclic peptide of claim 1 wherein at least one of R$_{10}$ and R$_{17}$ comprise at least one L- or D-isomer amino acid.

5. The cyclic peptide of claim 1 wherein R$_{10}$ is a single L- or D-isomer amino acid with an aliphatic side chain and R$_{17}$ is not present.

6. The cyclic peptide of claim 5 wherein the aliphatic side chain is —(CH$_2$)$_3$—CH$_3$.

7. The cyclic peptide of claim 1 wherein R$_{10}$ is a single L- or D-isomer amino acid with a side chain comprising at least one nitrogen atom.

8. The cyclic peptide of claim 7 wherein R$_{10}$ is an L- or D-isomer of Arg, Lys, Orn, Dab, Dap or Cit.

9. The cyclic peptide of claim 1 wherein R$_{10}$ and R$_{17}$ each comprise at least one L- or D-isomer amino acid.

10. The cyclic peptide of claim 1 wherein R$_9$ is —(CH$_2$)$_2$—C(=O)—NH—(CH$_2$)$_3$—.

11. The cyclic peptide of claim 1 wherein R$_9$ is —(CH$_2$)$_3$—NH—C(=O)—(CH$_2$)$_2$—.

12. The cyclic peptide of claim 1 which is of formula (II):

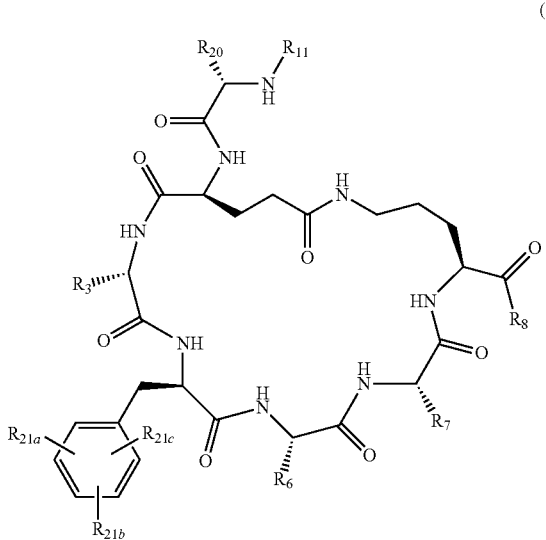

(II)

or a pharmaceutically acceptable salt thereof, wherein $R_{20}$ is linear or branched $(C_1-C_{10})$alkyl, $(C_1-C_{10})$alkyl-$N(R_{19a})(R_{19b})$, $(C_1-C_{10})$alky-NH—$(CH_2)_z$—$N(R_{19a})(R_{19b})$, $(C_1-C_{10})$alkyl-NH—C(=NH)—$N(R_{19a})(R_{19b})$ or $(C_1-C_{10})$alkyl-NH—C(=O)—$N(R_{19a})(R_{19b})$, wherein any $(C_1-C_{10})$alkyl carbon atom may be optionally substituted with oxo or replaced by oxygen; and $R_{21a}$, $R_{21b}$ and $R_{21c}$ are the same or different, and are each independently hydrogen, halo, $(C_1-C_{10})$alkyl-halo, $(C_1-C_{10})$alkyl, $(C_1-C_{10})$alkoxy, $(C_1-C_{10})$alkylthio, aryl, $(C_1-C_{10})$alkylaryl, aryloxy, nitro, nitrile, sulfonamide, amino, monosubstituted amino, disubstituted amino, hydroxy, carboxy, or alkoxy-carbonyl.

13. A cyclic peptide of formula (III) or (IV):

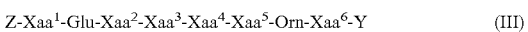

(III)

or

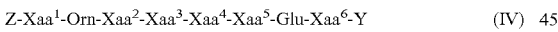

(IV)

or a pharmaceutically acceptable salt thereof, wherein

Z is H or a $C_1$ to $C_7$ acyl group comprising a linear or branched alkyl, cycloalkyl, alkyl cycloalkyl, aryl or aralkyl;

$Xaa^1$ is optionally present, and if present is from one to three amino acids;

$Xaa^2$ is Pro, optionally substituted with hydroxyl, halogen, sulfonamide, alkyl, —O-alkyl, aryl, alkyl-aryl, alkyl-O-aryl, alkyl-O-alkyl-aryl, or —O-aryl, or $Xaa^3$ is an amino acid with a side chain comprising at least one primary amine, secondary amine, alkyl, cycloalkyl, cycloheteroalkyl, aryl, heteroaryl, ether, sulfide, or carboxyl;

$Xaa^3$ is an amino acid with a side chain comprising substituted or unsubstituted aryl, but excluding L- or D-isomers of substituted Phe wherein Z is $CH_3$—C(=O)— and $Xaa^1$ is Arg;

$Xaa^4$ is Pro or $Xaa^4$ is an amino acid with a side chain comprising at least one primary amine, secondary amine, guanidine, urea, alkyl, cycloalkyl, cycloheteroalkyl, aryl, heteroaryl, or ether;

$Xaa^5$ is an amino acid with a side chain comprising at least one aryl or heteroaryl, optionally substituted with one or more ring substituents, and when one or more are present, are the same or different and independently hydroxyl, halogen, sulfonamide, alkyl, —O-alkyl, aryl, or —O-aryl, but excluding substituted D-Phe where Z-$Xaa^1$- is Ac-Arg, $Xaa^6$ is not present and Y is hydroxyl or amide;

$Xaa^6$ is optionally present, and if present is from one to three amino acids; and Y is a C-terminal group selected from the group consisting of —C(=O)—OH and —C(=O)—$N(R_a)(R_b)$ where $R_a$ and $R_b$ are each independently H or a $C_1$ to $C_4$ linear, branched or cyclic alkyl chain;

wherein the cyclic peptide of formula (III) or (IV) is cyclized through the side chains of Glu and Orn;

but excluding cyclic peptides of formula (III) wherein Z is Ac, $Xaa^1$ is Arg, $Xaa^2$ is Pro or Ser(Bzl), $Xaa^3$ is unsubstituted D-Phe, $Xaa^4$ is Arg, $Xaa^5$ is Trp, $Xaa^6$ is not present and Y is —OH or —$NH_2$.

14. The cyclic peptide of claim 13 wherein $Xaa^1$ is a single amino acid with a side chain including at least one primary amine, guanidine or urea group.

15. The cyclic peptide of claim 14 wherein $Xaa^1$ is an L- or D-isomer of Arg, Lys, Orn, Dab, Dap or Cit.

16. The cyclic peptide of claim 13 wherein $Xaa^3$ is D-Phe, optionally substituted with from one to three ring substituents.

17. The cyclic peptide of claim 16 wherein the ring substituents are the same or different, and are each independently halo, $(C_1-C_{10})$alkyl-halo, $(C_1-C_{10})$alkyl, $(C_1-C_{10})$alkoxy, $(C_1-C_{10})$alkylthio, aryl, $(C_1-C_{10})$alkylaryl, aryloxy, nitro, nitrile, sulfonamide, amino, monosubstituted amino, disubstituted amino, hydroxy, carboxy, or alkoxy-carbonyl.

18. The cyclic peptide of claim 13 of formula IV wherein

Z is the N-terminal group acetyl (Ac);

$Xaa^1$ is a single amino acid selected from the group consisting of Nle, Lys, Arg and D-Arg;

$Xaa^2$ is selected from the group consisting of His, Ala, Dab, Gln, Asn, Pro and Ser (Bzl);

$Xaa^3$ is D-Phe;

$Xaa^4$ is Arg;

$Xaa^5$ is Trp;

$Xaa^6$ is absent; and

Y is a C-terminal group selected from the group consisting of —$NH_2$ and —OH.

19. The cyclic peptide of claim 18 wherein $Xaa^2$ is Asn; and

Y is —$NH_2$.

20. The cyclic peptide of claim 18 wherein $Xaa^1$ is a single amino acid selected from the group consisting of Lys, Arg and D-Arg;

$Xaa^2$ is Asn; and

Y is —$NH_2$.

* * * * *

UNITED STATES PATENT AND TRADEMARK OFFICE
CERTIFICATE OF CORRECTION

PATENT NO. : 9,273,098 B2
APPLICATION NO. : 13/311817
DATED : March 1, 2016
INVENTOR(S) : Xin Chen and Wei Yang It is certified that error appears in the above-identified patent and that said Letters Patent is hereby corrected as shown below:

In the Claims

Claim 1, Column 98, line 36, replace "-$(CH_2)_3$-$(CH_2)_3$-NH-C(=O)-$(CH_2)_2$-;" with -- -$(CH_2)_3$-NH-C(=O)-$(CH_2)_2$-; --.

Signed and Sealed this
Sixteenth Day of August, 2016

Michelle K. Lee
*Director of the United States Patent and Trademark Office*